US011338057B2

(12) United States Patent
Francis et al.

(10) Patent No.: US 11,338,057 B2
(45) Date of Patent: *May 24, 2022

(54) MICROFLUIDIC EXTRUSION

(71) Applicant: Embody, Inc., Norfolk, VA (US)

(72) Inventors: Michael P. Francis, Norfolk, VA (US); Stella Petrova, Blacksburg, VA (US); Nicholas Thayer, Morrisville, NC (US)

(73) Assignee: Embody, LLC, Norfolk, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/328,854

(22) Filed: May 24, 2021

(65) Prior Publication Data
US 2021/0283305 A1 Sep. 16, 2021

Related U.S. Application Data

(62) Division of application No. 16/779,196, filed on Jan. 31, 2020, now Pat. No. 11,020,509.

(Continued)

(51) Int. Cl.
A61L 27/24 (2006.01)
A61L 27/38 (2006.01)
(Continued)

(52) U.S. Cl.
CPC ........... A61L 27/24 (2013.01); A61L 17/105 (2013.01); A61L 17/14 (2013.01);
(Continued)

(58) Field of Classification Search
None
See application file for complete search history.

(56) References Cited

U.S. PATENT DOCUMENTS 5,171,273 A 12/1992 Silver et al.
5,679,372 A * 10/1997 Shimuzu ............... A61L 15/325
424/443
(Continued)

FOREIGN PATENT DOCUMENTS

CN 1596996 A 3/2005
CN 107261210 A 10/2017
(Continued)

OTHER PUBLICATIONS

Fathima et al., "Interaction of aldehydes with collagen: effect on thermal, enzymatic and conformational stability," International Journal of Biological Macromolecules 34 (2004) 241-247 (Year: 2004).*
(Continued)

Primary Examiner — Aradhana Sasan
(74) Attorney, Agent, or Firm — Plumsea Law Group, LLC

(57) ABSTRACT

Implantable scaffolds made from biopolymer fibers. Biopolymer is dissolved in acid in a closed container made of materials inert to the acid and to the collagen to form a biopolymer solution. The solution is stirred, then centrifuged to degas it. The degassed solution is put into syringes on a holder. The number of syringes equals the number of fibers in the bundle. The syringes are mounted in a rotatable holder. Essentially equal quantities of degassed solution are extruded from the syringes to produce fibers, which are gathered and fed into a formation buffer bath. The fibers are kept taught after extrusion and dehydrated in a dehydrating solution in a dehydrating bath. The fibers are wound a collector to collect the bundle. Scaffolds then are made.

30 Claims, 46 Drawing Sheets

Related U.S. Application Data

(60) Provisional application No. 62/800,317, filed on Feb. 1, 2019.

(51) Int. Cl.
| | |
|---|---|
| *A61L 17/10* | (2006.01) |
| *A61L 17/14* | (2006.01) |
| *D01D 5/06* | (2006.01) |
| *D01D 5/02* | (2006.01) |
| *D01D 5/38* | (2006.01) |
| *D01D 7/00* | (2006.01) |
| *D01F 4/00* | (2006.01) |

(52) U.S. Cl.
CPC ......... *A61L 27/3804* (2013.01); *A61L 27/386* (2013.01); *D01D 5/02* (2013.01); *D01D 5/06* (2013.01); *D01D 5/38* (2013.01); *D01D 7/00* (2013.01); *D01F 4/00* (2013.01); *A61L 2430/10* (2013.01)

(56) References Cited

U.S. PATENT DOCUMENTS

| | | | |
|---|---|---|---|
| 7,862,831 | B2 | 1/2011 | Wang et al. |
| 7,878,786 | B2 | 2/2011 | Yost et al. |
| 8,048,361 | B2 | 11/2011 | Wang et al. |
| 8,491,457 | B2 | 7/2013 | Atala et al. |
| 8,585,753 | B2 | 11/2013 | Scanlon et al. |
| 8,586,345 | B2 | 11/2013 | Simpson et al. |
| 8,697,044 | B2 | 4/2014 | Schroeder et al. |
| 9,034,239 | B2 | 5/2015 | Yun et al. |
| 9,198,750 | B2 | 12/2015 | Van Kampen et al. |
| 9,393,104 | B2 | 7/2016 | Kampen et al. |
| 9,421,305 | B2 | 8/2016 | Lee et al. |
| 9,597,430 | B2 | 3/2017 | Ratcliffe et al. |
| 9,683,011 | B2 | 6/2017 | Wnek et al. |
| 9,757,132 | B2 | 9/2017 | Laurencin et al. |
| 11,020,509 | B2 * | 6/2021 | Francis ............... A61L 17/14 |
| 2002/0090725 | A1 | 7/2002 | Simpson et al. |
| 2002/0100725 | A1 | 8/2002 | Lee et al. |
| 2003/0105528 | A1 | 6/2003 | Shimp et al. |
| 2003/0114937 | A1 | 6/2003 | Leatherbury et al. |
| 2005/0008675 | A1 | 1/2005 | Bhatia et al. |
| 2005/0113938 | A1 | 5/2005 | Jamiolkowski et al. |
| 2006/0154063 | A1 | 7/2006 | Fujihara et al. |
| 2006/0204539 | A1 | 9/2006 | Atala et al. |
| 2007/0269481 | A1 | 11/2007 | Li et al. |
| 2008/0051888 | A1 | 2/2008 | Ratcliffe et al. |
| 2008/0188936 | A1 | 8/2008 | Ball et al. |
| 2008/0260794 | A1 * | 10/2008 | Lauritzen ............... A61L 15/32 424/423 |
| 2009/0098175 | A1 | 4/2009 | Buehrer et al. |
| 2009/0202430 | A1 | 8/2009 | Hoemann et al. |
| 2009/0202616 | A1 | 8/2009 | Chong et al. |
| 2009/0240342 | A1 | 9/2009 | Lindh, Sr. et al. |
| 2010/0063599 | A1 | 3/2010 | Brunelle et al. |
| 2010/0145367 | A1 | 6/2010 | Ratcliffe |
| 2010/0191332 | A1 | 7/2010 | Euteneuer et al. |
| 2010/0233233 | A1 * | 9/2010 | Zheng ............... A61L 27/3804 424/423 |
| 2010/0291058 | A1 | 11/2010 | Bowlin et al. |
| 2010/0292791 | A1 | 11/2010 | Lu et al. |
| 2010/0331980 | A1 | 12/2010 | Lee et al. |
| 2011/0224702 | A1 | 9/2011 | Van Kampen et al. |
| 2011/0238178 | A1 | 9/2011 | Downes et al. |
| 2011/0293685 | A1 | 12/2011 | Kuo et al. |
| 2012/0271416 | A1 * | 10/2012 | Mackay ............ A61B 17/0401 623/13.14 |
| 2012/0273993 | A1 | 11/2012 | Shoseyov et al. |
| 2013/0095167 | A1 | 4/2013 | Warnke |
| 2013/0149532 | A1 | 6/2013 | Yun et al. |
| 2014/0011416 | A1 | 1/2014 | Yang et al. |
| 2014/0051169 | A1 | 2/2014 | Ganey et al. |
| 2014/0112973 | A1 | 4/2014 | Steinberg et al. |
| 2014/0288271 | A1 * | 9/2014 | Zheng ............... A61L 27/3604 530/356 |
| 2015/0045454 | A1 | 2/2015 | Kong et al. |
| 2015/0081000 | A1 | 3/2015 | Hossainy et al. |
| 2015/0086607 | A1 | 3/2015 | Johnson et al. |
| 2015/0230918 | A1 | 8/2015 | Detamore et al. |
| 2015/0367030 | A1 | 12/2015 | Murray |
| 2016/0015852 | A1 | 1/2016 | Liou et al. |
| 2016/0022865 | A1 | 1/2016 | Francis et al. |
| 2016/0068654 | A1 | 3/2016 | Huh et al. |
| 2016/0106548 | A1 | 4/2016 | Li et al. |
| 2016/0130558 | A1 | 5/2016 | Baer |
| 2016/0136895 | A1 | 5/2016 | Beyer et al. |
| 2016/0263280 | A1 | 9/2016 | Harrell |
| 2016/0279219 | A1 | 9/2016 | Mooney et al. |
| 2016/0279301 | A1 | 9/2016 | He et al. |
| 2016/0287374 | A1 | 10/2016 | Soletti et al. |
| 2016/0296627 | A1 | 10/2016 | Garcia et al. |
| 2016/0317281 | A1 | 11/2016 | Van Kampen et al. |
| 2016/0325013 | A1 | 11/2016 | Li et al. |
| 2016/0325022 | A1 | 11/2016 | Liu et al. |
| 2017/0233834 | A1 | 8/2017 | Purcell et al. |
| 2017/0273775 | A1 | 9/2017 | Rocco et al. |
| 2018/0193524 | A1 | 7/2018 | Shoseyov et al. |
| 2018/0368982 | A1 | 12/2018 | Ball |
| 2021/0252190 | A1 * | 8/2021 | Francis ............... A61L 17/08 |

FOREIGN PATENT DOCUMENTS

| | | | |
|---|---|---|---|
| EP | 2322234 | B1 | 9/2005 |
| EP | 1216296 | B1 | 4/2009 |
| EP | 1863547 | B1 | 5/2016 |
| GB | 1058472 | * | 5/1964 |
| GB | 1103715 | * | 8/1965 |
| WO | 98/30252 | A1 | 7/1998 |
| WO | 99/39724 | A1 | 8/1999 |
| WO | 2007109304 | A2 | 9/2007 |
| WO | 2008131293 | A2 | 10/2008 |
| WO | 2009079211 | A1 | 6/2009 |
| WO | 2009/149181 | A2 | 12/2009 |
| WO | 2013/093921 | A1 | 6/2013 |
| WO | 2013123147 | A1 | 8/2013 |
| WO | 2013/172788 | A1 | 11/2013 |
| WO | 2015/138970 | A1 | 9/2015 |
| WO | 2016/042211 | A1 | 3/2016 |
| WO | 2016156992 | A2 | 10/2016 |
| WO | 2017053757 | A1 | 3/2017 |
| WO | 2018092098 | A1 | 5/2018 |
| WO | 2018/212792 | A2 | 11/2018 |
| WO | 2018212792 | A2 | 11/2018 |
| WO | 2019084209 | A1 | 5/2019 |

OTHER PUBLICATIONS

Rangaraj, A., Harding, K. and Leaper, D. (2011) 'Role of collagen in wound management', Wounds UK, 7(2), pp. 54-63.

Ratcliffe, A. et al., (2015) 'Scaffolds for Tendon and Ligament Repair and Regeneration', Annals of Biomedical Engineering, 43(3), pp. 819-831. doi: 10.1007/s10439-015-1263-1.

Ratner, B. D. (2011) 'The biocompatibility manifesto: Biocompatibility for the twenty-first century', Journal of Cardiovascular Translational Research, 4, pp. 523-527. doi: 10.1007/s12265-011-9287-x.

Reddy, N., Reddy, R. and Jiang, Q. (2015) 'Crosslinking biopolymers for biomedical applications', Trends in Biotechnology. Elsevier Ltd, 33(6), pp. 362-369. doi: 10.1016/j.tibtech.2015.03.008.

Sanchez-Ruiz, J. M. (1995) 'Differential scanning calorimetry of proteins.', in Proteins: Structure, Function, and Engineering. Subcellular Biochemistry, pp. 133-176. doi: 10.1007/978-1-4899-1727-0_6., Abstract Only.

Schlegel, T. F. et al. (2018) 'Radiologic and clinical evaluation of a bioabsorbabie collagen implant to treat partial-thickness tears: a prospective multicenter study', Journal of Shoulder and Elbow Surgery, 27(2), pp. 242-251. doi: 10.1016/j.jse.2017.08.023.

Seon, J. K., Song, E. K. and Park, S. J. (2006) 'Osteoarthritis after anterior cruciate ligament reconstruction using a patellar tendon autograft', International Orthopaedics, 30(2), pp. 94-98. doi: 10.1007/s00264-005-0036-0.

(56) References Cited

OTHER PUBLICATIONS

Shaerf, D. A. (2014) 'Anterior cruciate ligament reconstruction best practice: A review of graft choice', World Journal of Orthopedics, 5(1), p. 23. doi: 10.5312/wjo.v5.i1.23.

Shepherd, D. V. et al. (2015) 'The process of EDC-NHS crosslinking of reconstituted collagen fibres increases collagen fibrillar order and alignment', APL Materials, 3(1), pp. 1-13. doi: 10.1063/1.4900887.

Sherman, O. H. and Banffy, M. B. (2004) 'Anterior cruciate ligament reconstruction: Which graft is best?', Arthroscopy—Journal of Arthroscopic and Related Surgery, 20(9), pp. 974-980. doi: 10.1016/S0749-8063(04)00842-4.

Showery, J. E. et al. (2016) 'The Rising Incidence of Degenerative and Posttraumatic Osteoarthritis of the Knee in the United States Military', Journal of Arthroplasty, 31(10), pp. 2108-2114. doi: 10.1016/j.arth.2016.03.026.

Van Sliedregt, A. et al. (1994) 'Evaluation of polylactide monomers in an in vitro biocompatibility assay', Biomaterials, 15(4), pp. 251-256. doi: 10.1016/0142-9612(94)90047-7.

Smith, T. O. et al. (2014) 'Is reconstruction the best management strategy for anterior cruciate ligament rupture? A systematic review and meta-analysis comparing anterior cruciate ligament reconstruction versus non-operative treatment', Knee, 21(2), pp. 462-470. doi: 10.1016/j.knee.2013.10.009.

Stout, R. D. et al. (2005) 'Macrophages Sequentially Change Their Functional Phenotype in Response to Changes in Microenvironmental Influences', The Journal of Immunology, 175, pp. 342-349. doi: 10.4049/jimmunol.175.1.342.

Taylor, M. S. et al. (1994) 'Six bioabsorbable polymers: In vitro acute toxicity of accumulated degradation products', Journal of applied biomaterials, 5(2), pp. 151-157. doi: 10.1002/jab.770050208.

Tsugawa, A. J. and Verstraete, F. J. M. (2012) 'Suture materials and biomaterials', in Oral and Maxillofacial Surgery in Dogs and Cats, pp. 69-78. doi: 10.1016/B978-0-7020-4618-6.00007-5.

Umashankar, P., Kumari, T. and Mohanan, P. (2012) 'Glutaraldehyde treatment elicits toxic response compared to decellularization in bovine pericardium', Toxicology International, 19, pp. 51-58. doi: 10.4103/0971-6580.94513.

Vavken, P. et al. (2012) 'Biomechanical outcomes after bioenhanced anterior cruciateligament repair and anterior cruciate ligament reconstruction are equal in a porcine model', Arthroscopy—Journal of Arthroscopic and Related Surgery, 28(5), pp. 672-680. doi: 10.1016/j.arthro.2011.10.008.

Vijayaraghavan, R. et al. (2010) 'Biocompatibility of choline salts as crosslinking agents for collagen based biomaterials', Chemical Communications, 46(2), pp. 294-296. doi: 10.1039/b910601d.

Vunjak-Novakovic, G. et al. (2004) 'Tissue Engineering of Ligaments', Annual Review of Biomedical Engineering. Annual Reviews, 6(1), pp. 131-156. doi: 10.1146/annurev.bioeng.6.040803.140037.

Wang, J. H.-C., Guo, Q. and Li, B. (2012) 'Tendon Biomechanics and Mechanobiology—a mini-review of basic concepts', Journal of Hand Therapy, 25(2), pp. 133-141. doi: 10.1016/j.jht.2011.07.004. Tendon.

Wang, L. and Stegemann, J. P. (2011) 'Glyoxal crosslinking of cell-seeded chitosan/collagen hydrogels for bone regeneration', Acta Biomaterialia, 7(6), pp. 2410-2417. doi: 10.1016/j.actbio.2011.02.029.

Watts, G. (1975) 'Sutures for Skin Closure', The Lancet, 305(7906), p. 581.

Wiegnad, N., Patczai, B. and Lörinczy, D. (2017) 'The Role of Differential Scanning Calorimetry in the Diagnostics of Musculoskeletal Diseases', EC Orthopaedics. 4, pp. 164-177.

Woo, S. L. Y. et al. (1999) 'Tissue engineering of ligament and tendon healing', in Clinical Orthopaedics and Related Research. doi: 10.1097/00003086-199910001-00030.

Wren, T. A. L. et al. (2001) 'Mechanical properties of the human achilles tendon', Clinical Biomechanics, 16, pp. 245-251. doi: 10.1016/S0268-0033(00)00089-9.

Yaari, Amit, Schilt, Yaelle, Tamburu, Carmen, Raviv, Uri, and Shoseyov, Oded, 'Wet Spinning and Drawing of Human Recombinant Collagen', ACS Biomaterials, 2016.

Yang, G., Rothrauff, B. B. and Tuan, R. S. (2013) 'Tendon and ligament regeneration and repair: Clinical relevance and developmental paradigm', Birth Defects Research Part C—Embryo Today: Reviews, pp. 203-222. doi: 10.1002/bdrc.21041.

Yannas, I. V. and Tobolsky, A. V (1967) 'Cross-linking of Gelatine by Dehydration', Nature, 215(5100), pp. 509-510. doi: 10.1038/215509b0.

Cheng et al., "Isolation, Characterization and Evaluation of Collagen from Jellyfish *Rhopilema esculentum* Kishinouye for Use in Hemostatic Applications", PLoS ONE 12(1), Jan. 19, 2017, pp. 1-21.

Hochleitner et al., "Melt electrowriting below the critical translation speed to fabricate crimped elastomer scaffolds with non-linear extension behaviour mimicking that of ligaments and tendons", Acta Biomaterialia 72 (2018) 110-120.

Hochleitner et al., "Melt Electrowriting of Thermoplastic Elastomers", Macromolecular Rapid Communications, 2018, 39, 1800055, pp. 1-7.

Hoque et al., "Extrusion Based Rapid Prototyping Technique: An Advanced Platform for Tissue Engineering Scaffold Fabrication", Aug. 9, 2011, Biopolymers vol. 97, No. 2, pp. 83-93.

Hrynevich et al., "Dimension-Based Design of Melt Electrowritten Scaffolds", Nano-Micro Small, 2018, 14, 1800232, pp. 1-5.

Huang et al., "A review on polymer nanofibers by electrospinning and their applications in nanocomposites", Composites Science and Technology 63 (2003) 2223-2253.

Jha et al., "Electrospun Collagen: A Tissue Engineering Scaffold with Unique Functional Properties in aWide Variety of Applications", Journal of Nanomaterials, vol. 2011, Article ID 348268, pp. 1-15.

Krishnamoorthi et al., "Isolation and partial characterization of collagen from outer skin of Sepia pharaonis (Ehrenberg, 1831) from Puducherry coast", Biochemistry and Biophysics Reports 10 (2017) pp. 39-45.

Li et al., "3D-Printed Biopolymers for Tissue Engineering Application", International Journal of Polymer Science vol. 2014, Article ID 829145, pp. 1-13.

Lin et al., "Functionalized Poly(D,L-lactide) for Pulmonary Epithelial Cell Culture", Advanced Engineering Materials, Mar. 8, 2010.

Lu et al., "Techniques for fabrication and construction of three-dimensional scaffolds for tissue engineering", International Journal of Nanomedicine, Jan. 17, 2013, vol. 8, pp. 337-350.

Ma, "Scaffolds for tissue fabrication", Materialstoday, May 2004, pp. 30-40.

Addad et al., "Isolation, Characterization and Biological Evaluation of Jellyfish Collagen for Use in Biomedical Applications", Marine Drugs, Jun. 7, 2011, vol. 9, pp. 957-983.

Middleton et al., "Synthetic biodegradable polymers as orthopedic devices", Biomaterials 21 (2000) pp. 2335-2346.

Qiao et al., "Compositional and in Vitro Evaluation of Nonwoven Type I Collagen/Poly-di-lactic Acid Scaffolds for Bone Regeneration", Journal of Functional Biomaterials, 2015, vol. 6, pp. 667-686.

Rudolph et al., "Surface Modification of Biodegradable Polymers towards Better Biocompatibility and Lower Thrombogenicity", PLOS ONE, Dec. 7, 2015, pp. 1-17.

Sensini et al., "Biofabrication of bundles of poly(lactic acid)-collagen blends mimicking the fascicles of the human Achille tendon", IOP Publishing, Biofabrication, vol. 9 (2017) 015025.

Siow et al., "Plasma Methods for the Generation of Chemically Reactive Surfaces for Biomolecule Immobilization and Cell Colonization—A Review", Plasma Processes and Polymers, Jun. 2006, vol. 3, pp. 392-418.

Yang et al., "Tendon and Ligament Regeneration and Repair: Clinical Relevance and Developmental Paradigm", Birth Defects Res C Embryo Today, Sep. 2013, vol. 99(3). pp. 203-222.

Tham et al., "Surface Modification of Poly (lactic acid) (PLA) via Alkaline Hydrolysis Degradation", Advanced Materials Research, 2014, vol. 970, pp. 324-327. 4p. Abstract Only.

(56) References Cited

OTHER PUBLICATIONS

Zagho et al., "Recent Trends in Electrospinning of Polymer Nanofibers and their Applications as Templates for Metal Oxide Nanofibers Preparation", INTECH open science, open minds, 2016, pp. 4-24.
Zhang et al., "Electrospun scaffolds from silk fibroin and their cellular compatibility", Journal of Biomedical Materials Research Part A, 2009, pp. 997-983.
Zhong et al., "Isolation and Characterization of Collagen from the Body Wall of Sea Cucumber *Stichopus monotuberculatus*", Journal of Food Science, vol. 80, No. 4, 2015, pp. 671-679.
International Search Report and Written Opinion in International Application No. PCT/US2018/000119, dated Dec. 11, 2018.
Liao et al., "In Vitro and in Vivo Degradation of Mineralized Collagen-Based Composite Scaffold: Nanohydroxyapatite/Collagen/Poly(L-lactide)", Tissue Engineering Part A, vol. 10, Issue 1-2, 2004, pp. 73-80.
Cui et al., "Investigation of Drug Release and Matrix Degradation of Electrospun Poly(DL-lactide) Fibers with Paracetanol Inoculation", Biomacromolecules, 2006, 7, pp. 1623-1629.
D. Garlotta "A Literature Review of Poly(Lactlc Acid)", Journal of Polymers and the Environment, vol. 9, No. 2, 2001, pp. 63-84.
Haider et al., "A comprehensive review summarizing the effect of electrospinning parameters and potential applications of nanofibers in biomedical and biotechnology", Arabian Journal of Chemistry, 2015, pp. 1-24.
Jamshidi et al., "Thermal characterization of polylactides", Polymer, 1988, vol. 29, pp. 2229-2234.
Katsogiannis et al., "Porous electrospun polycarprolactone (PCL) fibres by phase separation", European Polymer Journal, 2015, 69, pp. 284-295.
Li et al., "Recent advances in stereocomplexation of enantiomeric PLA-based copolymers and applications", Progress in Polymer Science, 2016, 62, pp. 22-72 ; ; Abstract Only.
D. Lubasova and L. Martinova "Controlled Morphology of Porous Polyvinyl Butyral Nanofibers", Hindawi Publishing Corporation Journal of Nanomaterials, vol. 2011, Article ID 292516, 6 pages.
H. Tsuji "Poly(lactide) Stereocomplexes: Formation, Structure, Properties, Degradation, and Applications", Macroomol. Biosci., 2005, 5, pp. 569-597.
Demirbilek et al., "Oxidative Stress Parameters of L929 Cells Cultured on Plasma-Modified PDLLA Scaffolds", Appl. Biochem Biotechnol (2011) 164:780-792 ; Abstract Only.
Caves et al., "Fibrillogenesis in Continuously Spun Synthetic Collagen Fiber", J Biomed Mater Res B. Appl Biomater. Apr. 2010 ; 93(1): . doi:10.1002/jbm.b.31555.
Porcheray, F. et al. (2005) 'Macrophage activation switching: An asset for the resolution of inflammation', Clinical and Experimental Immunology, 142, pp. 481-489. doi: 10.1111/j.1365-2249.2005.02934.x.
Peters, A. E. et al. (2018) 'Tissue material properties and computational modelling of the human tibiofemoral joint: a critical review', PeerJ, 6, p. e4298. doi: 10.7717/peerj.4298.
Ahmad, Z. et al. (2015) 'Effect of 1-ethyl-3-(3-dimethylaminopropyl) carbodiimide and N-hydroxysuccinimide concentrations on the mechanical and biological characteristics of cross-linked collagen fibres for tendon repair', Regenerative Biomaterials, 2(2), pp. 77-85. doi: 10.1093/rb/rbv005.
Benjamin, M. (2010) The structure of tendons and ligaments, Regenerative Medicine and Biomaterials for the Repair of Connective Tissues. Woodhead Publishing. doi: 10.1533/9781845697792.2.351.
Benjamin, M., Kaiser, E. and Milz, S. (2008) 'Structure-function relationships in tendons: A review', Journal of Anatomy, 212, pp. 211-228. doi: 10.1111/j.1469-7580.2008.00864.x.
Bokor, D. J. et al. (2015) 'Preliminary investigation of a biological augmentation of rotator cuff repairs using a collagen implant: A 2-year MRI follow-up', Muscles, Ligaments and Tendons Journal, 5(3), pp. 144-150. doi: 10.11138/mltj/2015.5.3.144.
Brown, B. N. et al. (2012) 'Macrophage phenotype as a predictor of constructive remodeling following the implantation of biologically derived surgical mesh materials', Acta Biomaterialia, 8(3), pp. 978-987. doi: 10.1016/j.actbio.2011.11.031.
Brown, B. N. and Badylak, S. F. (2013) 'Expanded applications, shifting paradigms and an improved understanding of host-biomaterial interactions', Acta Biomaterialia. Acta Materialia Inc., 9(2), pp. 4948-4955. doi: 10.1016/j.actbio.2012.10.025.
Caruso, A. B. and Dunn, M. G. (2004) 'Functional evaluation of collagen fiber scaffolds for ACL reconstruction: Cyclic loading in proteolytic enzyme solutions', Journal of Biomedical Materials Research—Part A, 69(1), pp. 164-171. doi: 10.1002/jbm.a.20136.
Chattopadhyay, S. and Raines, R. T. (2014) 'Review collagen-based biomaterials for wound healing', Biopolymers, doi: 10.1002/bip.22486.
Chen, J. et al. (2009) 'Scaffolds for tendon and ligament repair: Review of the efficacy of commercial products', Expert Review of Medical Devices, 6(1), pp. 61-73. doi: 10.1586/17434440.6.1.61.
Chu, C. C. (2013) 'Materials for absorbable and nonabsorbable surgical sutures', in Biotextiles As Medical Implants, pp. 275-334. doi: 10.1533/9780857095602.2.275.
Cornwell, K. G. et al. (2007) 'Crosslinking of discrete self-assembled collagen threads: Effects on mechanical strength and cell-matrix interactions', Journal of Biomedical Materials Research Part A, 80, pp. 352-371.
Cornwell, K. G., Downing, B. R. and Pins, G. D. (2004) 'Characterizing fibroblast migration on discrete collagen threads for applications in tissue regeneration', Journal of Biomedical Materials Research—Part A, 71, pp. 55-62. doi: 10.1002/jbm.a.30132.
Wang, H. et al. (2014) 'Acceleration of wound healing in acute full-thickness skin wounds using a collagen-binding peptide with an affinity for MSCs', Burns & Trauma, 2(4), p. 181. doi: 10.4103/2321-3868.143623.
Delgado, L. M. et al. (2015) 'To Cross-Link or Not to Cross-Link? Cross-Linking Associated Foreign Body Response of Collagen-Based Devices', Tissue Engineering Part B: Reviews, 21(3), pp. 298-313. doi: 10.1089/ten.teb.2014.0290.
Dunn, M. G., Avasarala, P. N. and Zawadsky, J. P. (1993) 'Optimization of extruded collagen fibers for ACL reconstruction', Journal of Biomedical Materials Research, 27(12), pp. 1545-1552. doi: 10.1002/jbm.820271211.
Elder, S. et al. (2017) 'Suitability of EGCG as a Means of Stabilizing a Porcine Osteochondral Xenograft.', Journal of functional biomaterials, 8(43). doi: 10.3390/jfb8040043.
Enea, D. et al. (2011) 'Extruded collagen fibres for tissue engineering applications: Effect of crosslinking method on mechanical and biological properties', Journal of Materials Science: Materials in Medicine, 22(6), pp. 1569-1578. doi: 10.1007/s10856-011-4336-1.
Enea, D. et al. (2013) 'Collagen fibre implant for tendon and ligament biological augmentation. In vivo study in an ovine model', Knee Surgery, Sports Traumatology, Arthroscopy, 21(8), pp. 1783-1793. doi: 10.1007/s00167-012-2102-7.
Fathima, N. N. et al. (2004) 'Interaction of aldehydes with collagen: Effect on thermal, enzymatic and conformational stability', International Journal of Biological Macromolecules, 34(4), pp. 241-247. doi: 10.1016/j.ijbiomac.2004.05.004.
Gallagher, A. J. et al. (2012) 'Dynamic tensile properties of human skin', in 2012 IRCOBI Conference Proceedings—International Research Council on the Biomechanics of Injury, pp. 494-502.
Gentleman, E. et al. (2003) 'Mechanical characterization of collagen fibers and scaffolds for tissue engineering', Biomaterials, 24(21), pp. 3805-3813. doi: 10.1016/S0142-9612(03)00206-0.
Gigante, A. et al., (2009) 'Collagen I membranes for tendon repair: Effect of collagen fiber orientation on cell behavior', Journal of Orthopaedic Research, 27, pp. 826-832. doi: 10.1002/jor.20812.
Gordon, S. and Taylor, P. R. (2005) 'Monocyte and macrophage heterogeneity', Nature Reviews Immunology, 5(12), pp. 953-964. doi: 10.1038/nri1733.
Gough, J. E., Scotchford, C. A. and Downes, S. (2002) 'Cytotoxicity of glutaraldehyde crosslinked collagen/poly(vinyl alcohol) films is by the mechanism of apoptosis', Journal of Biomedical Materials Research, 61(1), pp. 121-130. doi: 10.1002/jbm.10145.
Haugh, M. G., Jaasma, M. J. and O'Brien, F. J. (2009) 'The effect of dehydrothermal treatment on the mechanical and structural

(56) References Cited

OTHER PUBLICATIONS properties of collagen-GAG scaffolds', Journal of Biomedical Materials Research—Part A, 89(2), pp. 363-369. doi: 10.1002/jbm.a. 31955.

Haynl, Christian, Hofmann, Eddie, Pawar, Kiran, Förster, Stephan, and Thomas Scheibel 'Microfluidics-produced collagen fibers show extraordinary mechanical properties,' NanoLetters 2016, 16 (9), pp. 5917-5922 DOI: 10.1021/acs.nanolett.6b02828.

Hogan, M. V. et al. (2015) 'Tissue engineering of ligaments for reconstructive surgery', Arthroscopy—Journal of Arthroscopic and Related Surgery. Arthroscopy Association of North America, 31(5), pp. 971-979. doi: 10.1016/j.arthro.2014.11.026.

Van Kampen, C. et al. (2013) 'Tissue-engineered augmentation of a rotator cuff tendon using a reconstituted collagen scaffold: A histological evaluation in sheep', Muscles, Ligaments and Tendons Journal, 3(229-235). doi: 10.11138/mltj/2013.3.3.229.

Brown, B. et al. (2009) 'Macrophage phenotype and remodeling outcomes in response to biologic scaffolds with and without a cellular component', Biomaterials, 30(8), pp. 1482-1491. doi: 10.1016/j.biomaterials.2008.11.040.Macrophage.

Kato, Y. P. et al. (1989) 'Mechanical properties of collagen fibres: a comparison of reconstituted and rat tail tendon fibres', Biomaterials, 10, pp. 38-42. doi: 10.1016/0142-9612(89)90007-0.

Kiapour, A. M. et al. (2015) 'Validation of Porcine Knee as a Sex-specific Model to Study Human Anterior Cruciate Ligament Disorders', Clinical Orthopaedics and Related Research, 473(2), pp. 639-650. doi: 10.1007/s11999-014-3974-2.

Koob, T. J. et al. (2001) 'Biocompatibility of NGDA-polymerized collagen fibers. II. Attachment, proliferation, and migration of tendon fibroblasts in vitro', Journal of Biomedical Materials Research, 56, pp. 40-48. doi: 10.1002/1097-4636(200107)56:1 <40::AID-JBM1066>3.0.CO;2-I.

Kudur, M. H. et al. (2009) 'Sutures and suturing techniques in skin closure', Indian Journal of Dermatology, Venereology and Leprology, 75(4), pp. 425-434. doi: 10.4103/0378-6323.53155.

Lee, C. H., Singla, A. and Lee, Y. (2001) 'Biomedical applications of collagen', International Journal of Pharmaceutics, 221, pp. 1-21. doi: 10.1016/S0378-5173(01)00691-3.

Leiter, J. R. S. et al. (2014) 'Long-term follow-up of ACL reconstruction with hamstring autograft', Knee Surgery, Sports Traumatology, Arthroscopy, 22(5), pp. 1061-1069. doi: 10.1007/s00167-013-2466-3.

Liu, S. H. et al. (1995) 'Collagen in tendon, ligament, and bone healing: A current review', Clinical Orthopaedics and Related Research, (318), pp. 265-278.

Maghdouri-White, Y. et al. (2019) 'Biomanufacturing and Translational Research of an Aligned Collagen-Based Electrospun Tissue ENgineered Device (TEND) for Tendon Regeneration', manuscript submitted.

Matsusue, Y. et al. (1995) 'Tissue reaction of bioabsorbable ultra high strength poly (L-lactide) rod: A long-term study in rabbits', Clinical Orthopaedics and Related Research, 317, pp. 246-253.

Meena, C., Mengi, S. A. and Deshpande, S. G. (1999) 'Biomedical and industrial applications of collagen', Proceedings of the Indian Academy of Sciences: Chemical Sciences, 111(2), pp. 319-329. doi: 10.1007/BF02871912.

Meyer, M. (2019) 'Processing of collagen based biomaterials and the resulting materials properties', BioMedical Engineering Online. BioMed Central, 18(1), pp. 1-74. doi: 10.1186/s12938-019-0647-0.

Mills, C. D. et al. (2000) 'M-1/M-2 Macrophages and the Th1/Th2 Paradigm', The Journal of Immunology, 164(12), pp. 6166-6173. doi: 10.4049/jimmunol.164.12.6166.

Wang, Ming-Che, Pins, G. D., Silver, F. H., 'Collagen fibres with improved strength for the repair of soft tissue injuries.' Biomaterials 15, 507-512 (1994).

Mosser, D. M. (2003) 'The many faces of macrophage activation', Journal of Leukocyte Biology, 73(2), pp. 209-212. doi: 10.1189/jlb.0602325.

Noyes, F. and Grood, E. (1976) 'The strength of the anterior cruciate ligament in humans and Rhesus monkeys', The Journal of Bone & Joint Surgery, 58(8), pp. 1074-1082. doi: 10.2106/00004623-197658080-00006.

Paul, R. G. and Bailey, A. J. (2003) 'Chemical stabilisation of collagen as a biometric.', TheScientificWorldJournal, 3, pp. 138-155. doi: 10.1100/tsw.2003.13.

Perrone, G. S. et al. (2017) 'Bench-to-bedside: Bridge-enhanced anterior cruciate ligament repair', Journal of Orthopaedic Research. doi: 10.1002/jor.23632.

Delguerra et al., "Optimization if the interaction between ethylene-vinyl alcohol copolymers and human endothelial cells", Journal of Materials Science: Materials in Medicine 7, 1996, 8-12.

"4 Figures: Liquid Crystalline Ordered Collagen Substrates for Applications in Tissue Engineering", ACS Biomaterials Science and Engineering, Mar. 2016, https://www.researchgate.net/publication/297595398.

Bishop et al., "Design of an Extrusion System to Optimize the Production of Self-Assembled Collagen Microthreads", Degree of Bachelor of Science Paper, Worcester Polytechnic Institute, Project No. GXP-0508, 2005.

Dong et al., "Electrospinning of Collagen Nanofiber Scaffolds from Benign Solvents", Macromol. Rapid Commun. 2009, 30 pp. 539-542.

Gentleman et al., "Mechanical characterization of collagen fibers and scaffolds for tissue engineering", Biomaterials 2003, 24, pp. 3805-3813.

Hwang et al., "Effects of Zero-Length and Non-Zero-Length Cross-Linking Reagents on the Optical Spectral Properties and Structures of Collagen Hydrogels", ACS Appl. Mater. Interfaces., 2012, 4, pp. 261-267.

Liu et al., "Novel 3D collagen scaffolds fabricated by indirect printing technique for tissue engineering", Abstract, J. Biomedical Materials Research Part B: Applied Biomaterials, 2008, Issue 2; pp. 519-528.

Oryan et al., "Chemical crosslinking of biopolymeric scaffolds: Current knowledge and future directions of crosslinked engineered bone scaffolds", International Journal of Biological Macromolecules 2018, 107, pp. 678-688.

Punnoose et al., "Electrospun Type 1 Collagen matrices using a novel benign solvent for Cardiac tissue engineering", Journal of Cellular Physiology, 2015.

Salgado et al., "Bone Tissue Engineering: State of the Art and Future Trends", Abstract, Macromolecular Bioscience, 2004, vol. 4, Issue 8, pp. 743-765.

Synthasome X-Repair Technology, FAQs, http://www.synthasome.com/xRepair-technology.php; accessed Mar. 22, 2017.

Tutak et al., "The support of bone marrow stromal cell differentiation by airbrushed nanofibers scaffolds", Abstract, Biomateriais, 2013, vol. 34, Issue 10, pp. 2389-2398.

Wortmann et al., "New Polymers for Needlesless Electrospinning from Low-Toxic Solvents", Nanomaterials, 2019, 9, 52, pp. 1-11.

Wright Achilles Tendon Information, http://www.wright.com/healthcare-professionals/graftjacket/applications/achilles-tendon; accessed Nov. 12, 2017.

Zobitz et al., "Determination of the Compressive Material Properties of the Supraspinatus Tendon", Journal of Biomechanical Engineering, 2001, vol. 123, pp. 47-51.

Gabler et al., "In Vivo Evaluation of Different Collagen Scaffolds in an Achilles Tendon Defect Model", BioMed Research International, vol. 2018, Article ID 6432742, pp. 1-11.

Kew et al., "Synthetic collagen fascicles for the regeneration of tendon tissue" 2012, www.elsevier.com/locate/actabiomat.

Winkler et al., "microfabricated, optically accessible device to study the effects of mechanical cues on collagen fiber organization" Biomed Microdevices (2014) 16:255-267.

Lee et al., "Microfluidic alignment of collagen fibers for in vitro cell culture" Biomed Microdevices (2006) 8: 35-41 DOI 10.1007/s10544-006-6380-z.

Zeugolis et al. "Cross-linking of extruded collagen fibers" Wiley InterScience (www.interscience.wiley.com). DOI: 10.1002/jbm.a. 32031 2008.

(56) References Cited

OTHER PUBLICATIONS

McCarty et al., "Layer-by-layer Collagen Deposition in Microfluidic Devices for Microtissue Stabilization" PMC Sep. 29, 2016.

Gillette et al.,"In situ collagen assembly for integrating microfabricated three-dimensional cell-seeded matrices" May 30, 2008; doi:10.1038/nmat2203.

PCT Invitation to Pay Additional Fees mailed Apr. 23, 2020 in International Application No. PCT/US2020/016244.

Notification of Transmittal of the International Search Report and the Written Opinion of the International Searching Authority, or the Declaration, for Application No. PCT/US2020/016244, dated Jun. 22, 2020.

Sarah Köster et al. "An in-situ Study of Collagen Self-Assembly Processes" Jan. 2008 ; 9(1): 199-2. Jan. 2008 ; 9(1): 199-207. doi:10.1021/bm700973t.07. doi:10.1021/bm700973t.

Kevin H. Lam et al. "A high-throughput microfluidic method for fabricating aligned collagen fibrils to study Keratocyte behavior" (2019) 21:99 https://doi.org/10.007/s10544-019-0436-3.

Babette Lanfer et al"The growth and differentiation of mesenchymal stem and progenitor cells cultured on aligned collagen matrices" www.elsevier.com/locate/biomaterials, 2009.

Phillip Lee et al., "Microfluidic alignment of collagen fibers for in vitro cell culture" Biomed Microdevices (2006) 8: 35-41 DOI 10.1007/s10544-006-6380-z.

Nima Saeidi et al. "Production of highly aligned collagen lamellae by combining shear force and thin film confinement" www.elsevier.com/locate/actabiomat, 2011.

Robert Spanneberg et al "Glyoxal modification of gelatin leads to change in properties of solutions and resulting films" (2011) DOI: 10.1039/c2sm06659a.

Bishop et al., (2005) "Design of an Extrusion System to Optimize the Production of Self-Assembled Collagen Microthreads", Degree of Bachelor of Science Paper, Worcester Polytechnic Institute, Project No. GXP-0508.

Decision Granting Request dated Apr. 4, 2020 in U.S. Appl. No. 16/779,196.

Restriction Requirement dated May 22, 2020 in U.S. Appl. No. 16/779,196.

Response to Restriction Requirement filed Jul. 20, 2020 in U.S. Appl. No. 16/779,196.

Preliminary Amendment filed Sep. 18, 2020 in U.S. Appl. No. 16/779,196.

Non Final Office Action dated Sep. 29, 2020 in U.S. Appl. No. 16/779,196.

Amendment and Request for Reconsideration filed Dec. 29, 2020 in U.S. Appl. No. 16/779,196.

Response to Rule 312 filed Apr. 23, 2021 Notice of Allowance dated Apr. 26, 2021 in U.S. Appl. No. 16/779,196.

Notice of Allowance dated Apr. 26, 2021 in U.S. Appl. No. 16/779,196.

* cited by examiner

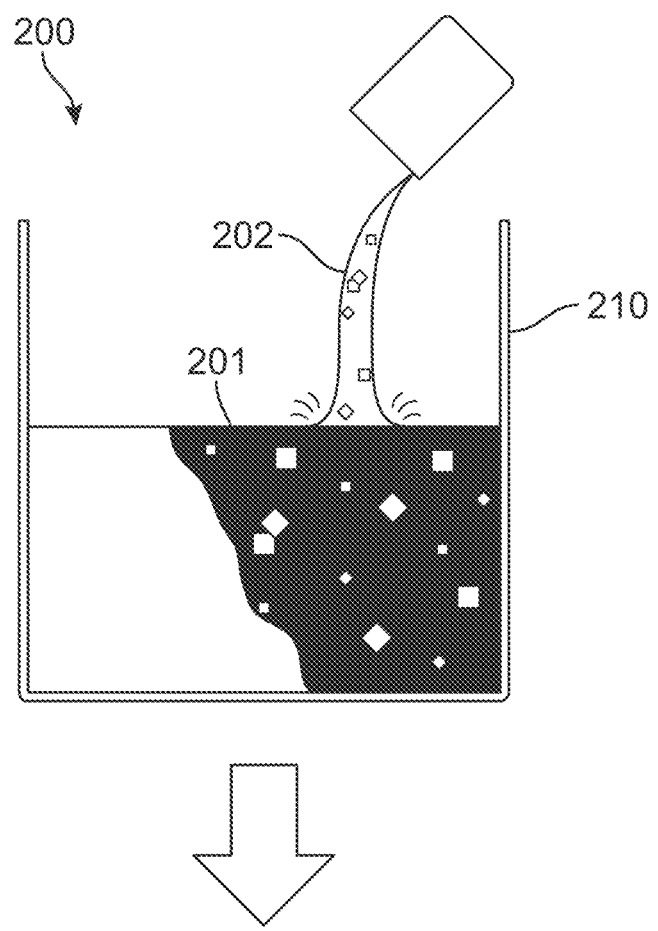
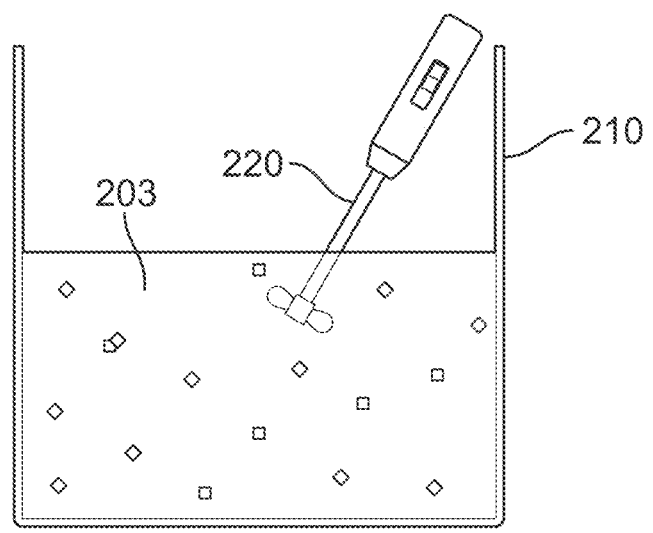
FIG. 2

Table 1

| Chemical | Vendor |
| --- | --- |
| Acetic Acid | Sigma-Aldrich, St. Louis, MO |
| Hydrochloric Acid (HCl) | Sigma-Aldrich, St. Louis, MO |
| NaCl (Sodium Chloride) | Sigma-Aldrich, St. Louis, MO |
| TES (N-Tris(hydroxymethyl)methyl-2-aminoethanesulfonic acid) | Sigma-Aldrich, St. Louis, MO |
| PEG (Polyethylene Glycol) | Santa Cruz Biotechnology, TX |
| $Na_2HPO_4$ (Sodium Phosphate Dibasic) | Sigma-Aldrich, St. Louis, MO |
| $NaH_2PO_4$ (Sodium Phosphate Monobasic) | J.T. Baker, PA |
| Choline Bitartarate | Sigma-Aldrich, St. Louis, MO |
| DL-Glyceraldehyde (DLG) | Sigma-Aldrich, St. Louis, MO |
| EDC (1-ethyl-3-(3-dimethylaminopropyl) carbodiimide) | Thermo Fisher Scientific, MA |
| NHS (N-Hydroxysuccinimide) | Life Technologies, CA |
| EGCG ((-)-Epigallocatechin gallate) | Sigma-Aldrich, St. Louis, MO |
| Glyoxal (GLY) | Sigma-Aldrich, St. Louis, MO |
| D-Sorbitol | Sigma-Aldrich, St. Louis, MO |
| Procyanidin | BulkActives, Taiwan |
| NDGA (Nordihydroguaiaretic acid) | Santa Cruz Biotechnology, TX |
| L-Lysine | Sigma-Aldrich, St. Louis, MO |
| O-Dextran | Sigma-Aldrich, St. Louis, MO |
| Ethanol Solution, 96% | Fisher Bioreagents, MA |

FIG. 17

Table 2

| Crosslinker | Collagen Starting Material | In Situ | Post | Crosslinker Concentration | Time [hours] | Mean UTS [MPa] ± S.E.M. | References |
|---|---|---|---|---|---|---|---|
| *Un-crosslinked* | *Telocollagen* | | | | | *6.1 ± 1.2* | |
| Choline Bitartarate | Telocollagen | Y | | 1mM | 0.5 | CBD[a] | (Vijayaragha van et al., 2010) |
| Choline Bitartarate | Telocollagen | Y | | 100mM | 0.5 | CBD[a] | |
| DHT | Telocollagen | | Y | | 72 | 16.0 ± 1.2* | (Yannas and Tobolsky, 1967; Haugh, Jaasma and O'Brien, 2009) |
| DHT | Telocollagen | | Y | | 120 | 13.1 ± 0.7 | |
| DHT | Telocollagen | | Y | | 24 | 4.7 ± 0.4 | |
| DHT/Glyoxal | Telocollagen | | Y | 10mM | 120/24 | 27.2 ± 2.8* | (Zeugolis, Paul and Attenburrow, 2009; Reddy, Reddy and Jiang, 2015) |
| DHT/Glyoxal | Telocollagen | | Y | 10mM | 24/24 | 22.0 ± 3.0 | |
| *DL-Glyceraldehyde* | *Atelocollagen* | | *Y* | *25mM* | *72* | *128.0 ± 11.8*° | |
| DL-Glyceraldehyde | Telocollagen | | Y | 25mM | 24 | 70.5 ± 6.0 | |
| DL-Glyceraldehyde | Atelocollagen | | Y | 25mM | 24 | 50.7 ± 3.3 | |
| DL-Glyceraldehyde | Telocollagen | | Y | 25mM | 72 | 40.3 ± 1.8 | |
| DL-Glyceraldehyde | Telocollagen | | Y | 10mM | 24 | 37.1 ± 2.2 | |
| DL-Glyceraldehyde | Telocollagen | | Y | 5mM | 24 | 35.3 ± 2.1 | |
| DL-Glyceraldehyde | Telocollagen | | Y | 50mM | 24 | 31.1 ± 1.2 | |
| DL-Glyceraldehyde | Telocollagen | Y | | 250mM | 5 | 27.3 ± 1.6 | |
| DL-Glyceraldehyde | Telocollagen | Y | | 500mM | 24 | 60.4 ± 1.5 | |
| DL-Glyceraldehyde | Telocollagen | | Y | 250mM | 5 | 60.2 ± 4.5 | |
| DL-Glyceraldehyde | Telocollagen | | Y | 500mM | 5 | 28.6 ± 1.5 | |

FIG. 18A to FIG. 18B

Table 2 (continued)

*from FIG. 18A*

| | | | | | | |
|---|---|---|---|---|---|---|
| *EDC* | *Telocollagen* | | *Y* | *0.25mM* | *24* | *16.6 ± 1.5\** | (Enea *et al.*, 2011) |
| EDC | Telocollagen | Y | | 0.25mM | 4 | 6.5 ± 0.5 | |
| EDC | Telocollagen | Y | | 0.25mM | 1 | 2.8 ± 0.1 | |
| EDC/NHS | Telocollagen | | Y | 0.25mM /0.125mM | 24 | 30.2 ± 1.0* | (Ahmad *et al.*, 2015; Shepherd *et al.*, 2015) |
| EGCG | Telocollagen | Y | | 200[μM] | 2 | 2.2 ± 0.1* | (Elder *et al.*, 2017) |
| EGCG | Telocollagen | Y | | 1mM | 2 | 1.1 ± 0.1 | |
| *Glyoxal* | *Telocollagen* | | *Y* | *10mM* | *72* | *121.2 ± 7.4\** | (Wang and Stegemann, 2011) |
| Glyoxal | Telocollagen | | Y | 10mM | 24 | 109.0 ± 7.4 | |
| Glyoxal | Telocollagen | | Y | 100mM | 72 | 76.2 ± 8.0 | |
| Glyoxal | Atelocollagen | | Y | 10mM | 24 | 62.1 ± 4.9 | |
| Glyoxal | Telocollagen | | Y | 1mM | 24 | 49.4 ± 1.6 | |
| Glyoxal | Telocollagen | | Y | 5mM | 24 | 45.9 ± 4.1 | |
| Glyoxal | Atelocollagen | | Y | 10mM | 72 | 28.6 ± 2.8 | |
| Glyoxal | Telocollagen | | Y | 500mM | 72 | 86.9 ± 5.5 | |
| Glyoxal | Telocollagen | | Y | 0.5mM | 24 | 48.3 ± 2.2 | |
| Glyoxal | Telocollagen | Y | | 10mM | 5 | 5.1 ± 0.2 | |
| Glyoxal | Telocollagen | Y | | 0.5mM | 5 | 2.3 ± 0.4 | |
| Glyoxal/DHT | Telocollagen | | Y | 10mM | 24/24 | 24.2 ± 1.3 | |
| Glyoxal/Vegetable Oil | Telocollagen | | Y | 10mM | 24/72 | 27.6 ± 2.2 | |
| Liquid Transglutaminase/ Glyoxal | Telocollagen | Y | Y | 0.1mg/ml 10mM | 72 | 6.2 ± 1.0 | |
| L-Lysine/Glyoxal | Telocollagen | Y | Y | 10mM/10mM | 2/24 | 96.9 ± 4.6* | |
| L-Lysine/Glyoxal | Telocollagen | Y | Y | 5mM/10mM | 2/24 | 32.2 ± 1.5 | |
| Methyl Glyoxal | Telocollagen | | Y | 10mM | 24 | 42.3 ± 4.1 | |

Table 2 *(continued)*

*from FIG. 18B*

| | | | | | | |
|---|---|---|---|---|---|---|
| NDGA | Telocollagen | | Y | 0.01gm/ml | 24 | 47.9 ± 4.2 | (Koob *et al.*, 2001; Zeugolis, Paul and Attenburrow, 2009) |
| O-Dextran | Telocollagen | | Y | 20% [w/v] | 24 | 4.4 ± 0.1 | |
| Procyanidin | Telocollagen | | Y | 2.5mg/ml | 24 | 19.3 ± 1.5 | |
| Procyanidin | Telocollagen | | Y | 5mg/ml | 24 | 13.3 ± 0.9 | |
| D-Sorbitol/Glyoxal | Telocollagen | Y | Y | 330mM/10mM | 72 | 22.2 ± 5.2 | |
| D-Sorbitol | Telocollagen | | Y | 200mM | 72 | 14.4 ± 0.7* | |
| D-Sorbitol | Telocollagen | | Y | 100mM | 72 | 5.8 ± 0.4 | |
| D-Sorbitol | Telocollagen | Y | | 200mM | 5 | 1.9 ± 0.2 | |
| UVR | Methacrylated | | Y | | 03 | 1.9 ± 0.2 | |
| UVR/Glyoxal | Methacrylated | | Y | 10 mM | 03/24 | 86.6 ± 10.1* | |

Notes: *<sup>a</sup>CBD: Could not be determined;*

*\* Significantly High UTS for the crosslinker group (p<0.01)*

FIG. 18C

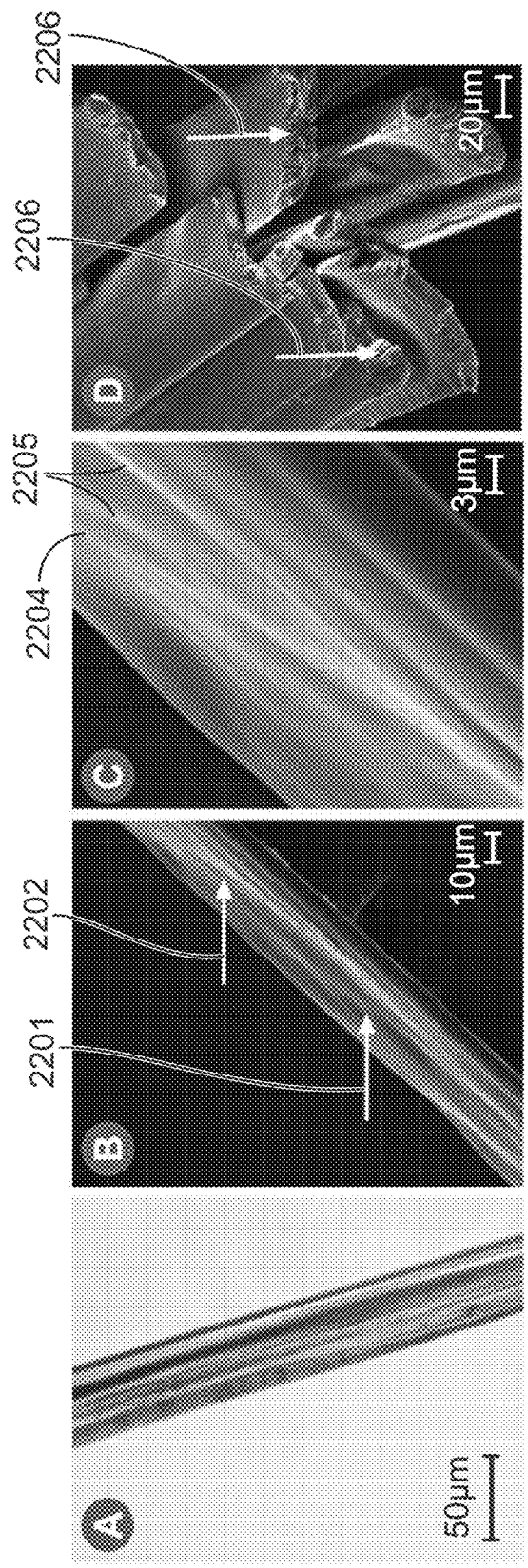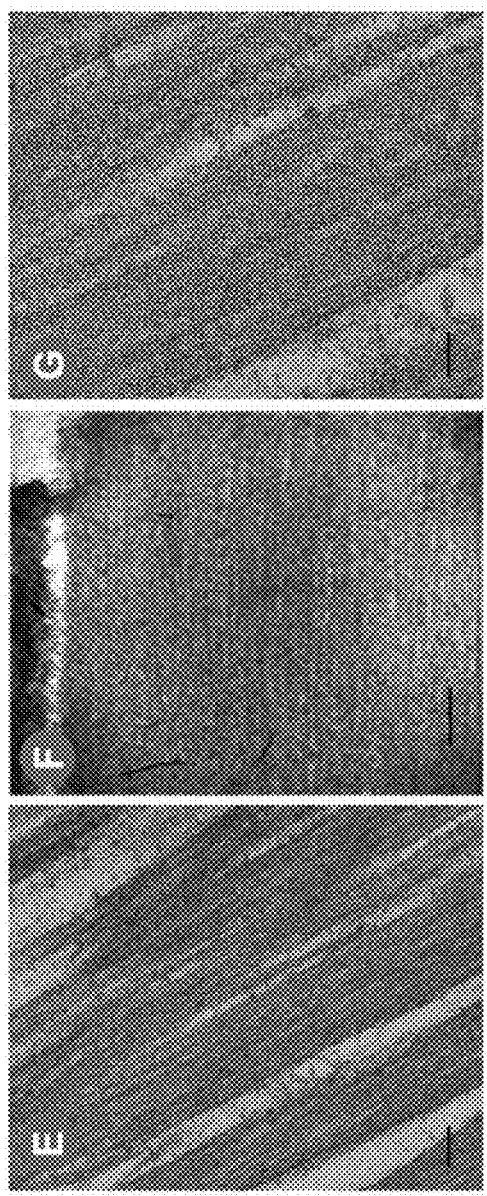
FIG. 22

| Reference | Crosslinker/Crosslinking Method | UTS (MPa) | Modulus (MPa) | Strain at Failure (%) |
|---|---|---|---|---|
| Present Study | Glyoxal | 299 ± 15 | 3431 ± 86 | 9.5 ± 1.6 |
| Yaari et al. | Glutaraldehyde | 151 ± 31 | 888 ± 153 | 20.5 ± 2 |
| Ahmad et al. | EDC[a] | 150 ± 100 | 1000 ± 600 | 18 ± 12 |
| Wang et al. | DHT | 92 ± 31 | 895 ± 206 | 12 ± 2 |
| Koob et al. | NDGA | 91 ± 10 | 696 ± 38 | 11 ± 1 |

Note:
[a]Values were estimated from graphical data published. Exact values were unavailable.

FIG. 45

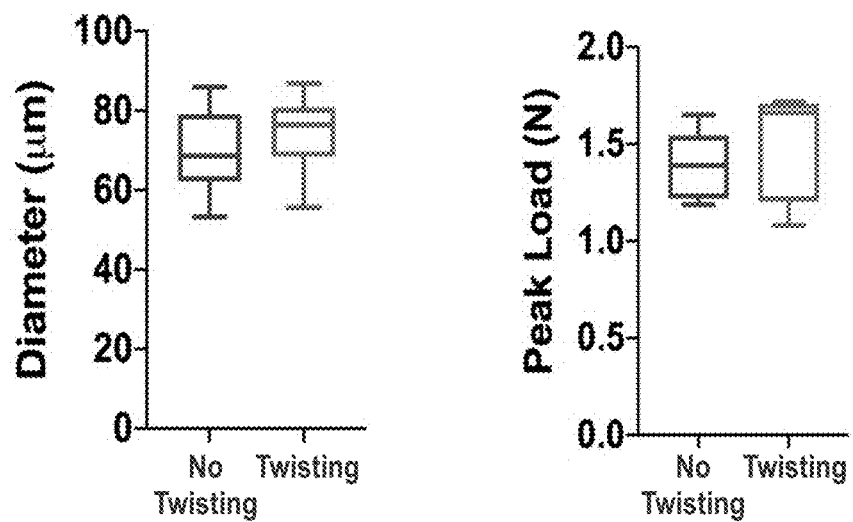
FIG. 47  FIG. 48
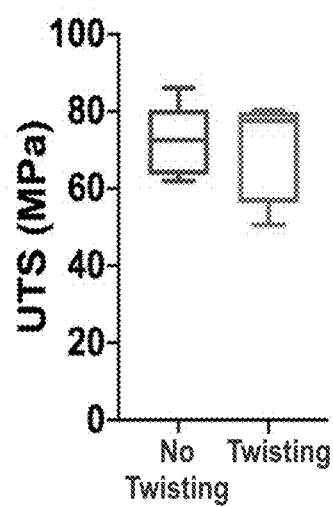 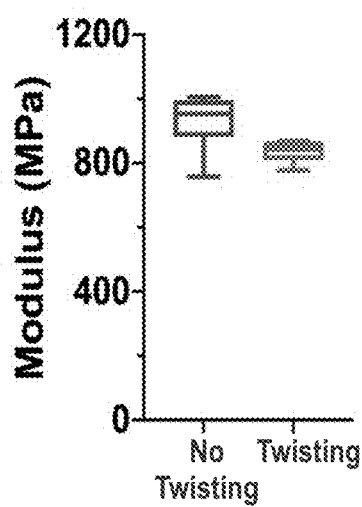 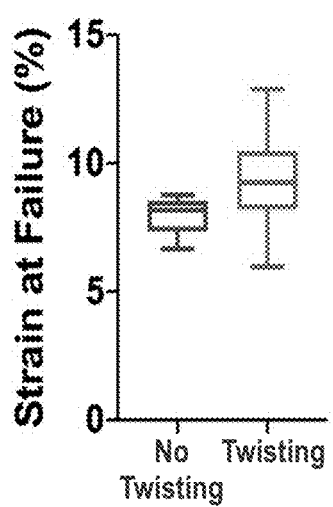
FIG. 49  FIG. 50  FIG. 51

MICROFLUIDIC EXTRUSION

CROSS-REFERENCE TO RELATED APPLICATIONS

This application is a divisional application of co-pending application Ser. No. 16/779,196, filed Jan. 31, 2020, and issued as U.S. Pat. No. 11,020,509, the disclosure of which is hereby incorporated by reference in its entirety. Co-pending application Ser. No. 16/779,196 claims the benefit of application Ser. No. 62/800,317, filed Feb. 1, 2019, the disclosure of which was incorporated by reference in its entirety.

STATEMENT REGARDING GOVERNMENTAL SUPPORT

The data presented in this application was supported at least in part by DARPA Contract HR0011-15-9-0006. The US government has certain rights in the invention.

BACKGROUND OF THE INVENTION

1. Field of the Disclosure

The present disclosure relates to a method for manufacturing collagen fibers and their incorporation into scaffolds and implantable biocompatible devices prepared with such fibers. In particular, the disclosure relates to a method for extruding collagen fibers having superior mechanical strength, biocompatibility, and immunological properties.

2. Description of Related Art

Collagen is a fibrous insoluble protein consisting of bundles of tiny reticular fibrils. Collagen protein molecules combine to form white, glistening, inelastic fibers of the tendons, the ligaments, and the fascia. Collagen is found in connective tissue, including skin, bone, ligaments, and cartilage.

In particular, collagen fibrils combine to form tough connective tissue such as ligaments and tendons. Many efforts have been made to manufacture collagen-containing tissue for use in the body to replace damaged collagen body parts, including in particular ligaments and tendons. Such implantable devices may replace the damaged part directly or may serve to provide a scaffold to facilitate repair of, and eventually replace, damaged soft tissues such as tendons and ligaments.

Such products must function in a variety of challenging biomechanical environments in which multiple functional parameters must be addressed. These parameters include, for example, compatibility with bodily tissue and fluids, strength, flexibility, and biodegradability.

There is a need in the art for a system and method that addresses the shortcomings of the prior art discussed above.

SUMMARY OF THE INVENTION

In one aspect, the disclosure is directed to a biopolymer fiber comprising a collagen, wherein the biopolymer fiber has one or more of the following characteristics:
an ultimate tensile strength of between about 1 MPa to about 1,700 MPa;
a modulus of elasticity of between about 10 MPa to about 20,000 MPa;
a strain at break of between about 2 percent and about 45 percent elongation;
an average fiber diameter between about 10 µm and about 90 µm;
maintains its strength after soaking in DPBS at room temperature for at least about 1 hour; and
wherein the filament exhibits an ordered, longitudinally oriented structure.

In another aspect, the disclosure is directed to a bundle of the biopolymer fibers comprising between 2 and about 10,000 fibers.

In still another aspect, the disclosure is directed to an implantable biopolymer scaffold for supporting repair of a soft tissue injury comprising the biopolymer fibers or the bundle.

The disclosure also is directed to a woven sheet-like support, a patch, or a brace comprising biopolymer fibers.

In yet another aspect, the disclosure is directed to a method for producing a biopolymer fiber. The method comprises the steps of:
dissolving collagen in an acid solution to form a collagen solution;
passing the collagen solution at a first speed through a first needle having a first diameter simultaneously with passing a formation buffer solution at a second speed through a second needle coaxially surrounding the first needle and having a second diameter greater than the first diameter to form a sheath around the collagen solution to form a coaxial flow,
wherein the second flow rate of the foundation buffer solution through the second needle is at least twice the first flow rate of the collagen solution through the first needle,
passing the coaxially-flowing collagen and formation buffer solution through a reaction zone comprising a fibril-forming bath for a time and at speeds sufficient to form a fiber,
dehydrating the collagen fiber at an extrusion speed, and
withdrawing the fiber onto a spool at a third speed greater than the extrusion speed sufficient to increase molecular alignment and reduce the diameter of the fiber.

In another aspect, the disclosure is directed to a method for producing a biopolymer fiber. The method comprises the steps of:
dissolving collagen in an acid solution to form a collagen solution;
passing the collagen solution at a first speed through a first needle having a first diameter into a formation buffer solution,
passing the collagen and formation buffer solution through a reaction zone comprising a fibril-forming bath for a time and at speeds sufficient to form a fiber,
dehydrating the collagen fiber at an extrusion speed, and
withdrawing the fiber onto a spool at a speed of between about 2 times the extrusion speed and about 10 times the extrusion speed sufficient to increase molecular alignment and reduce the diameter of the fiber.

In yet another aspect, the disclosure is directed to a method for producing a biopolymer fiber comprising the steps of:
dissolving clinical-grade collagen in an acid solution to form a collagen solution;
passing the collagen solution at a first volumetric flow rate through a first needle to yield a first speed simultaneously with passing a formation buffer solution at a second speed in a tube coaxially surrounding the first needle and forming a sheath around the collagen solution to form a coaxial flow, wherein the speed of the foundation buffer solution is between about 2 times and about 20 times the first speed of the collagen solution through the first needle, passing the coaxially-flowing collagen and formation buffer solution through a reaction zone comprising a fibril-forming bath for a time and at speeds sufficient to form a fiber, dehydrating the collagen fiber at an extrusion speed, and withdrawing the fiber at a third speed greater than the extrusion speed sufficient to increase molecular alignment and reduce the diameter of the fiber.

In a further aspect, the disclosure is directed to a method for producing a biopolymer fiber comprising the steps of:

dissolving clinical-grade collagen in an acid solution to form a collagen solution;

extruding the solution through a nozzle into a guide that passes the extruded solution into a bath of formation buffer;

dehydrating fiber formed in the formation buffer bath; and collecting the fiber.

In a still further aspect, the disclosure is directed to a method for producing a biopolymer fiber comprising the steps of:

dissolving clinical-grade collagen in an acid solution to form a collagen solution;

passing the collagen solution at a first speed through a first needle having a first diameter into a formation buffer solution, passing the collagen and formation buffer solution through a reaction zone comprising a fiber-forming bath for a time and at speeds sufficient to form a fiber, dehydrating the collagen fiber at an extrusion speed, and withdrawing the fiber onto a spool at a speed of between about 2 times the extrusion speed and about 12 times the extrusion speed, in one or more stages, sufficient to increase molecular alignment and reduce the diameter of the fiber.

The disclosure also includes an aspect of providing an implantable biopolymer scaffold for supporting repair of a soft tissue injury comprising the biopolymer fibers, a method for supporting the repair of a soft tissue injury comprising the implantation of the biopolymer scaffold.

Other systems, methods, features, and advantages of the invention will be, or will become, apparent to one of ordinary skill in the art upon examination of the following figures and detailed description. It is intended that all such additional systems, methods, features, and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 2 is a schematic diagram illustrating a first step in the formation of a collagen solution in an embodiment of the disclosure;

FIG. 17 is a table summarizing compositions used in the disclosure;

FIG. 18A is the first of three sections of a table summarizing conditions used for embodiments;

FIG. 18B is the second of three sections of a table summarizing conditions used for embodiments;

FIG. 18C is the third of three sections of a table summarizing conditions used for embodiments;

FIG. 22 is magnified images of compositions manufactured in accordance with the disclosure;

FIG. 45 is a table summarizing comparative information;

FIG. 47 summarizes the properties and characteristics of an embodiment of the disclosure;

FIG. 48 summarizes the properties and characteristics of an embodiment of the disclosure;

FIG. 49 summarizes the properties and characteristics of an embodiment of the disclosure;

FIG. 50 summarizes the properties and characteristics of an embodiment of the disclosure;

FIG. 51 summarizes the properties and characteristics of an embodiment of the disclosure;

DETAILED DESCRIPTION

Figure 1:
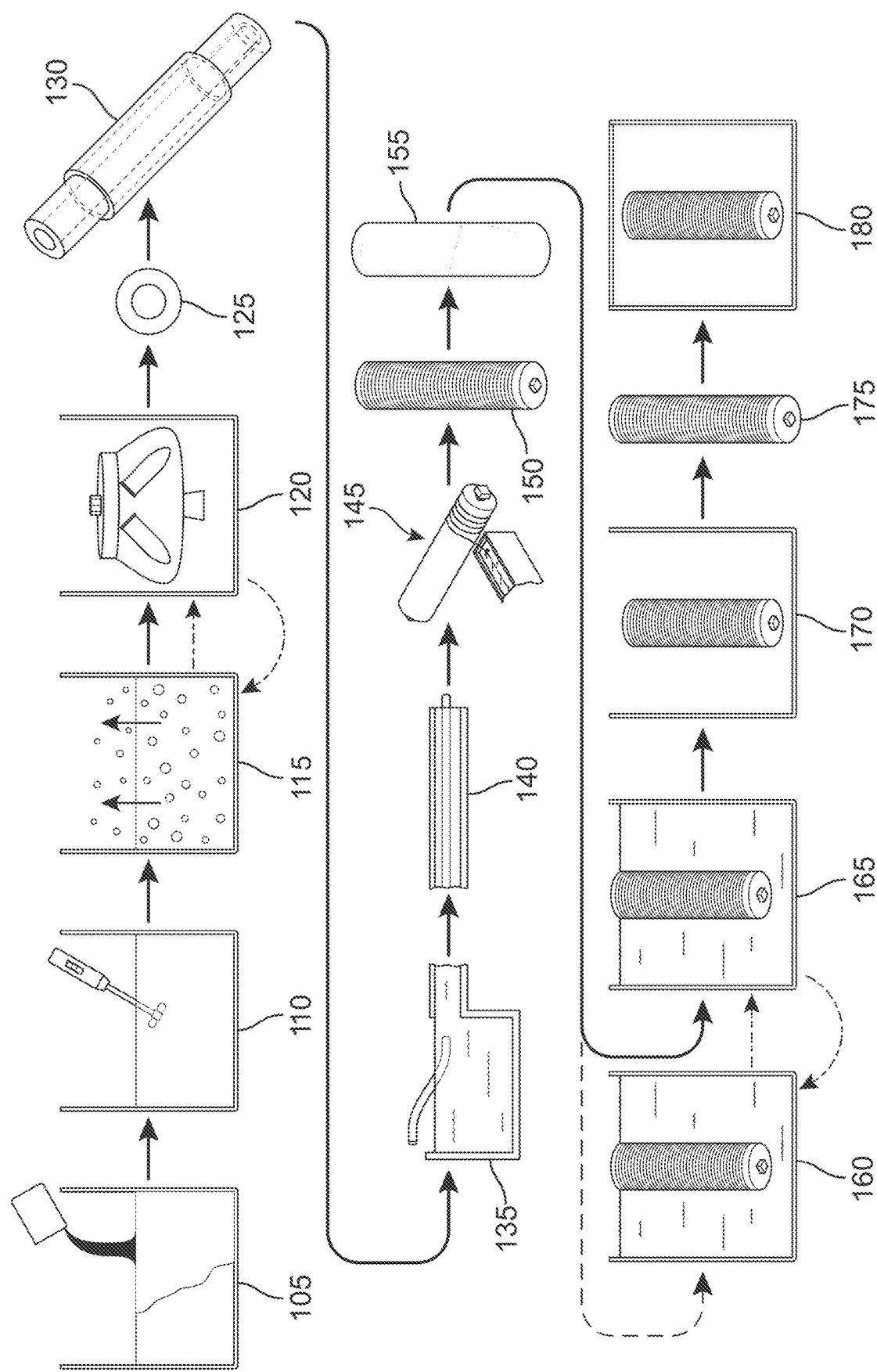
FIG. 1 is a schematic diagram of an embodiment of a method disclosed in the specification.
Figure 3:
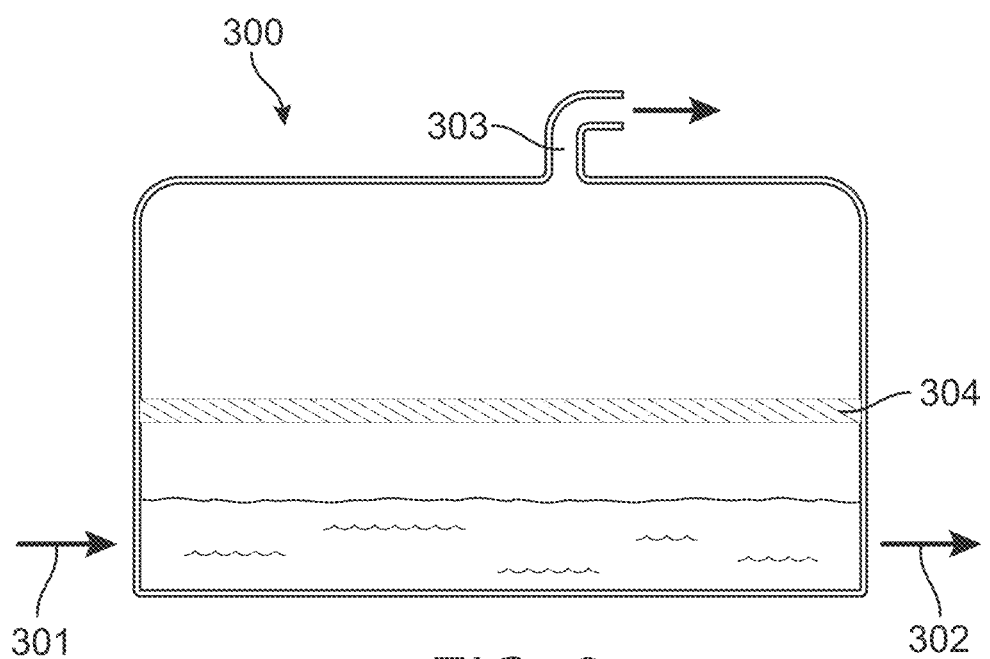
FIG. 3 is a schematic illustration of use of a degasser in collagen preparation in an embodiment of a method disclosed in the specification.

In one aspect, the disclosure is directed to a biopolymer fiber comprising collagen, wherein the biopolymer fiber has one or more of the following characteristics:

an ultimate tensile strength of between about 1 MPa to about 1,700 MPa;

a modulus of elasticity of between about 10 MPa to about 20,000 MPa;

a strain at break of between about 2 percent and about 45 percent elongation;

an average fiber diameter between about 10 μm and about 90 μm;

maintains its strength after soaking in DPBS at room temperature for at least about 1 hour; and wherein the filament exhibits an ordered, longitudinally oriented structure.

In another aspect, the disclosure is directed to an implantable biopolymer scaffold for supporting repair of a soft tissue injury comprising at least one biopolymer sheet comprising biopolymer fibers, wherein the biopolymer comprises collagen and the biopolymer fibers have one or more of the following characteristics:

an ultimate tensile strength of between about 1 MPa to about 1,700 MPa;

a modulus of elasticity of between about 10 MPa to about 20,000 MPa;

a strain at break of between about 2 percent and about 45 percent elongation;

an average fiber diameter between about 10 μm and about 90 μm;

maintains its strength after soaking in DPBS at room temperature for at least about 1 hour; and wherein the filament exhibits an ordered, longitudinally oriented structure.

The fibers exhibit an ordered, longitudinally-oriented structure, and allow cellular infiltration following implantation of the fibers, and devices made with the inventive fibers, into a subject.

In another aspect, the disclosure includes an implantable biopolymer scaffold for repair or replacement of a human body part.

Biopolymer fiber typically is formed of collagen. In particular, telocollagen typically is obtained from any source (human, bovine, recombinants, jelly fish, etc.). Bio-acceptable polymer, such as silk fibroin; other types of collagen such as type II collagen; fibrin/fibrinogen; basement membrane proteins; hyaluronic acid, poly ethylene oxide, poly ethylene glycol, poly caprolactone, polyethylene, polyhydroxybutyrate, PDLA; PDLLA and high molecular weight PDLLA; PLGA; and blends thereof, may be blended with collagen to form biopolymer fiber.

In still another aspect, the disclosure is directed to a method for producing a biopolymer fiber comprising the steps of dissolving collagen in an acid solution to form a collagen solution. In one embodiment of this method, the collagen then is passed at a first speed through a first needle having a first diameter to have a first speed simultaneously with passing a formation buffer at a second volumetric flow rate through a second needle coaxially surrounding the first needle and having a second diameter greater than the first diameter to form a sheath around the collagen solution to form a coaxial flow. The second volumetric flow rate of the formation buffer through the second needle is at least about twice the first volumetric flow rate of the collagen solution through the first needle.

The coaxially-flowing collagen and formation buffer are passed through a reaction zone comprising a fibril-forming bath for a time and at speeds sufficient to form a fiber, which is withdrawn onto a spool at a third speed greater than the first speed, and typically twice the speed at which the fiber is extruded through the dehydration bath, sufficient to increase molecular alignment and reduce the diameter of the fiber. The fibers then may be cross-linked and dried.

In yet another aspect, the disclosure is directed to an alternative method for producing a biopolymer fiber. In this embodiment, a collagen solution is prepared and injected into a reaction zone in a comprising a fiber-forming bath, such as a bath of formation buffer, for a time and at speeds sufficient to form a fiber. The fiber is withdrawn on a spool at a speed between about 2 to about 10 times faster than the injection speed to increase molecular alignment and reduce the diameter of the fiber. The fibers then may be cross-linked and dried.

In various embodiments of the disclosure, collagen or collagen and other suitable biopolymers are made into biopolymer or collagen fiber. For ease of understanding, the features of the disclosure will be described as they relate to collagen. However, collagen may be blended or combined with suitable biopolymers in various combinations and proportions to obtain fibers of the type disclosed herein.

Throughout the specification, steps that might typically be taken together during a typical manufacturing process, such as washing and drying or soaking and drying, may be taken or repeated as appropriate to achieve a desired result. For example, in an embodiment, a composition may be washed and dried before advancing to the next step. In some embodiments, the material may be washed a second time and dried a second time before advancing to the next processing step, or may be washed a second time, then advanced.

In other embodiments, a first washing or drying step may be made optional. Thus, a material typically washed, then dried, may go directly to the drying step, and then moved on to the next processing step. The skilled practitioner can recognize circumstances under which steps may be repeated or eliminated.

The constructs, such as scaffolds, made from the fibers, allow cellular ingrowth, that is, various types of cells from the animal into which the fiber (and devices made from the fiber) is implanted will grow into the pores of the scaffold, preferably aligned with the fibers in the scaffold. Constructs and scaffolds comprise single layer and multi-layer articles that may be used as a substitute for a known repair feature, such as sutures used to re-attach body parts, for example opposing ends of a ruptured Achilles tendon. In addition to providing supporting structures for use in repairing torn or damaged tendons, embodiments of the disclosure are suitable in ligament repair as well. Thus, other exemplary ligaments for which the scaffolds or the present invention may be used to provide support include the ACL, MCL, PCL, UCL, and other human and animal ligaments. Other surgeries for which products of the disclosure are useful include superior capsular reconstruction as a treatment option for superior rotator cuff tears, and in particular for otherwise irreparable or difficult to repair partial or full tears. Similarly, a multi-layered sheet may be used to overlap a repair to strengthen it.

In particular, embodiments of the disclosure may be suitable for repair of ligaments, tendons, and other soft tissues of animals of all types. Collagen fibers of the disclosure may be used, for example, to reattach torn ligaments and tendons, even those with only a partial tear. Plural fibers also may be twisted, bundled, braided, interwoven, or otherwise arranged to improve a form factor that is easier to work with than a single fiber is to manipulate, for example during surgery. Improving the form factor may make it easier to locate a fiber or platform accurately. Other form factors may be constructed to serve as a reinforcement or internal brace for a torn natural body part. A brace connects from one bone to another bone to support a joint. Typically, a brace forms an isometric joint with restored biomechanics and the isometry of the native joint.

The efficacy of collagen fiber produced in accord with embodiments of the disclosure may be illustrated by studying repairs made in, for example, rabbits. In particular, reinforcements and internal brace and over-sewn structures of rabbit knees are suitable for evaluating the properties and characteristics of collagen fiber of the disclosure and of structures made from this fiber.

FIG. 1 illustrates an embodiment of a system and method for manufacturing collagen fiber. The system and method may be described as comprising four sections or manufacturing areas. A collagen solution is prepared in the first section, and collagen fiber is formed in the second section. The collagen fiber then is collected in the third section and then may be post-processed to yield wet or dry collagen fiber in the fourth section, post-treatments or end of treatment.

The steps in the system and method illustrated in FIG. 1 may be grouped into four categories, as follows:

| Category | Name | Steps Included |
| --- | --- | --- |
| 1 | Preparing Collagen Solution | 105-120 |
| 2 | Forming Collagen Fiber | 125-130 |
| 3 | Collecting Collagen Fiber | 135-150 |
| 4 | Post-Treatment or End | 155-180 |

As seen at step 105 of FIG. 1, collagen is combined with an acidic solution and stirred thoroughly at step 110. In some embodiments, the acid is between about 0.01 M and about 0.50 M acetic acid. In other embodiments, the acid is between about 0.01 M and about 0.50 M hydrochloric acid. The solution may be degassed at step 115, and then centrifuged at step 120 to remove residual bubbles. Resultant collagen solution is extruded from a needle, and there may be a second needle co-axial therewith that supplies a formation buffer solution in step 125. The resultant forming fiber may continue in through a formation tube in step 130. The resultant product is a formed collagen fiber.

The fiber then continues to a collection system, wherein the fiber is separated from the formation buffer solution at step 135 and dehydrated at step 140. The collagen fiber is recovered at step 145 and air-dried at step 150. Then, post-processing may be carried out, as illustrated at step 155, step 160, step 165, and step 170. Air-dried collagen fiber on a spool is submerged in cross-linking solution at step 155, optionally washed at step 160, air-dried at step 165, and desiccated to form dried fiber at step 170. As illustrated in FIG. 1 by the dot-dash line, material may be optionally washed at step 160, dried at step 165, and returned to wash step 160.

Alternatively, collagen is injected into a bath of formation solution to form a fiber. In this system, a second needle for coaxial injection of formation buffer is not necessary. Collagen thus injected is introduced to a collection system through dehydration at step 140. The fiber then is processed in accordance with the remainder of the processing steps.

FIG. 1 provides a generalized view of a system and method for carrying out an embodiment of the disclosure. Additional details and disclosure are included in the following particular aspects and embodiments of the description.

In an embodiment, the disclosure is directed to a method for producing a biopolymer fiber comprising the steps of dissolving collagen in an acidic solution to form a collagen solution. The collagen then is passed at a first volumetric flow rate through a first needle having a first diameter to have a first speed simultaneously with passing a formation buffer at a second volumetric flow rate through a second needle coaxially surrounding the first needle and having a second diameter greater than the first diameter to form a sheath around the collagen solution to form a coaxial flow. The second volumetric flow rate of the formation buffer through the second needle is at least twice the first volumetric flow rate of the collagen solution through the first needle.

The coaxially-flowing collagen and formation buffer is passed through a reaction zone comprising a fibril-forming bath for a time and at volumetric flow rates sufficient to form a fiber, which is withdrawn onto a spool at a third speed greater than the first speed. The third speed, typically about twice the speed at which the fiber is extruded through the dehydration bath, is sufficient to increase molecular alignment and reduce the diameter of the fiber. The fibers then are cross-linked and dried.

In another embodiment, the disclosure is directed to an alternative method for producing a biopolymer fiber. Collagen solution is prepared and injected into a reaction zone in a comprising a fibril-forming bath, such as a bath of formation buffer, for a time and at speeds sufficient to form a fiber. The second needle to form coaxial flow of formation buffer is not needed. Rather, collagen fiber is injected directly into the fibril-forming bath, and then carried through the dehydration bath. The fiber is carried through by being withdrawn on a spool at a speed between about 2 to about 4 times faster than the injection speed to increase molecular alignment and reduce the diameter of the fiber. The fibers then may be cross-linked and dried.

Figure 13:
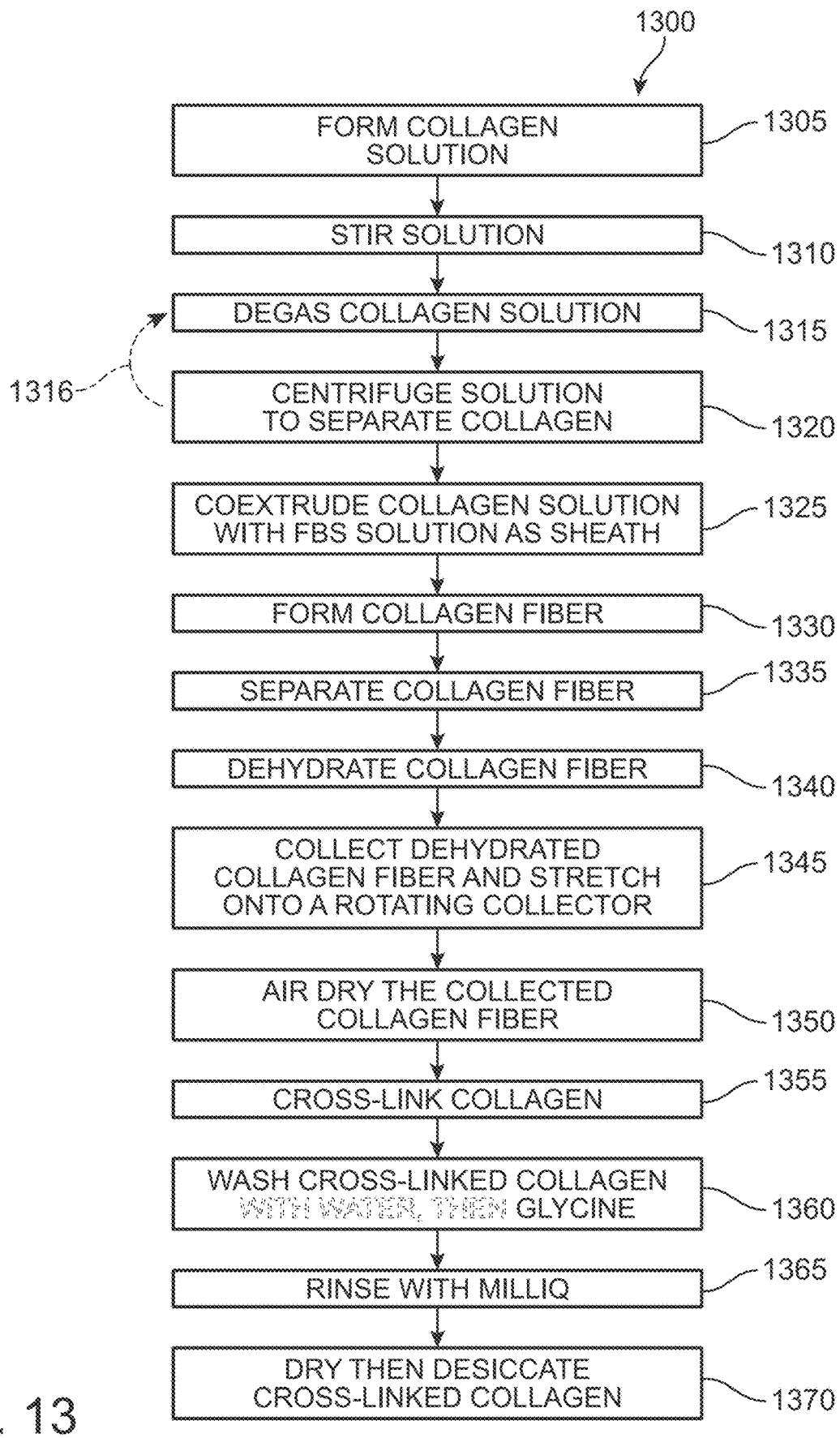
FIG. 13 is a schematic illustration of a method of an embodiment of the disclosure.

An embodiment of the method 1300 is summarized in FIG. 13. A collagen solution is prepared, as illustrated. A collagen solution is formed at step 1305. A biopolymer may be mixed with the collagen. Collagen is dissolved in an acidic solution to form a viscous solution. The solution is stirred at step 1310 to ensure thorough mixing. The mixed solution may have entrapped gas, and so may be degassed one or more times in degasser step 1315. The collagen solution then may be centrifuged, as illustrated at step 1320. Optionally, the degas/centrifuge steps may be repeated, as shown by the dot-dash lines on FIG. 1 and as feature 1316 on FIG. 13, to reduce the volume of gas entrapped in the solution.

Thus-prepared collagen solution is formed into a collagen fiber by coaxial extrusion with a formation buffer solution that serves as a sheath for the fiber core, as shown at step 1325. The formation buffer solution volumetric flow rate typically is at least twice the volumetric flow rate of the forming collagen. This arrangement suppresses formation of individual fibrils; stretches and orients the fiber; and may smooth the surface of the fiber by imparting flow-induced crystallization to the fiber.

The collagen fiber then is collected. As formation of the collagen fiber is completed at step 1330, the collagen then is separated from the formation buffer solution at step 1335 and dehydrated in a dehydrating solution at step 1340. The dehydrated collagen then is collected on a rotating spool in step 1345, which further stretches the fiber by rotating at a rate greater than, and typically about twice, the rate at which the fiber is supplied from dehydrating solution step 1340. Thus-collected fiber then is air-dried on the spool in step 1350.

In an alternative embodiment, collagen solution is formed into a collagen fiber by direct injection into formation buffer solution. Thus, step 1325 is skipped. The fiber is collected, separated from formation buffer solution, and dehydrated in a dehydrating solution at step 1340. The fiber is collected on a rotating spool in step 1345, which collects fiber at a speed of between about 2 times the formation speed and about 4 times the formation speed.

Fiber that has been air-dried on the spool then may be post-processed. Fiber may be cross-linked in a cross-linking solution at step 1355, and then may be rinsed at step 1360. The fiber then is air dried at step 1365 and desiccated at step 1370 to yield dry cross-linked collagen fiber.

The equipment used in making collagen fiber is made of conventional materials of construction suitable for resisting attack by any of the raw materials used to make collagen fiber in accordance with embodiments of the disclosure. Metals, plastics, and other materials have properties and characteristics suitable to resist attack by raw materials, intermediates, solvents, and products during manufacture of collagen fiber.

Another aspect of the disclosure is directed to a collagen fiber having one or more of the following characteristics:

an ultimate tensile strength of between about 1 MPa to about 1,700 MPa;

a modulus of elasticity of between about 10 MPa to about 20,000 MPa;

a strain at break of between about 4 percent and about 12 percent elongation;

an average fiber diameter between about 16 $\mu$m and about 70 $\mu$m; and at least maintains its strength after soaking in biological fluid for about 1 hour.

The fiber exhibits an ordered, longitudinally-oriented structure, and the fiber allows infiltration of cellular growth.

A fiber of this embodiment is manufactured in accordance with the method of an embodiment of the disclosure. Collagen may be obtained from many sources and in various forms. The quality of the collagen fiber may be related to the quality of the raw material used. In some embodiments, bovine collagen typically is used. Bovine collagen may be obtained in natural form or as lyophilized powder.

Bovine collagen 202 may be made into a viscous solution 203 by dissolution in an acidic solution. Both mineral acids, such as hydrochloric acid, and organic acids, such as acetic acid, may be used to prepare a collagen solution. For example, in an embodiment, type I bovine collagen with telopeptide ends intact may be dissolved in about 0.01 M acetic acid to about 0.5 M acetic acid 201 in vessel 210 to form a viscous solution 203 comprising about 16 mg collagen/mL of solution. Solution concentrations may range from about 10 mg collagen/mL of solution to about 19 mg collagen/mL of solution. In another embodiment, lyophilized type I bovine corium with telopeptide ends attached is mixed into a mineral acid, such as HCl having a concentration of from about 0.01 M to about 0.5 M, to form a solution having a concentration between about 10 mg collagen/mL of solution to about 19 mg collagen/mL of solution, typically about 16 mg collagen/mL of solution.

In embodiments, collagen is allowed to dissolve for at least about 14 hours, typically at least about 15 hours, and more typically at least about 16 hours. In some embodiments, collagen solution 301 is degassed in degasser 300 to remove bubbles from collagen solution 301. Screen 304 ensures that collagen is not drawn out of the degasser through the degasser gas flow exit 303. Degasser 303 typically is operated at a pressure of between about 0 psia and about 3 psia. Collagen solution may be exposed to up to about 2 degassing cycles, typically between about 1 and about 2 cycles. Degassing removes gas bubbles that likely would interfere with and disrupt extrusion of fibrous collagen.

Figure 4:
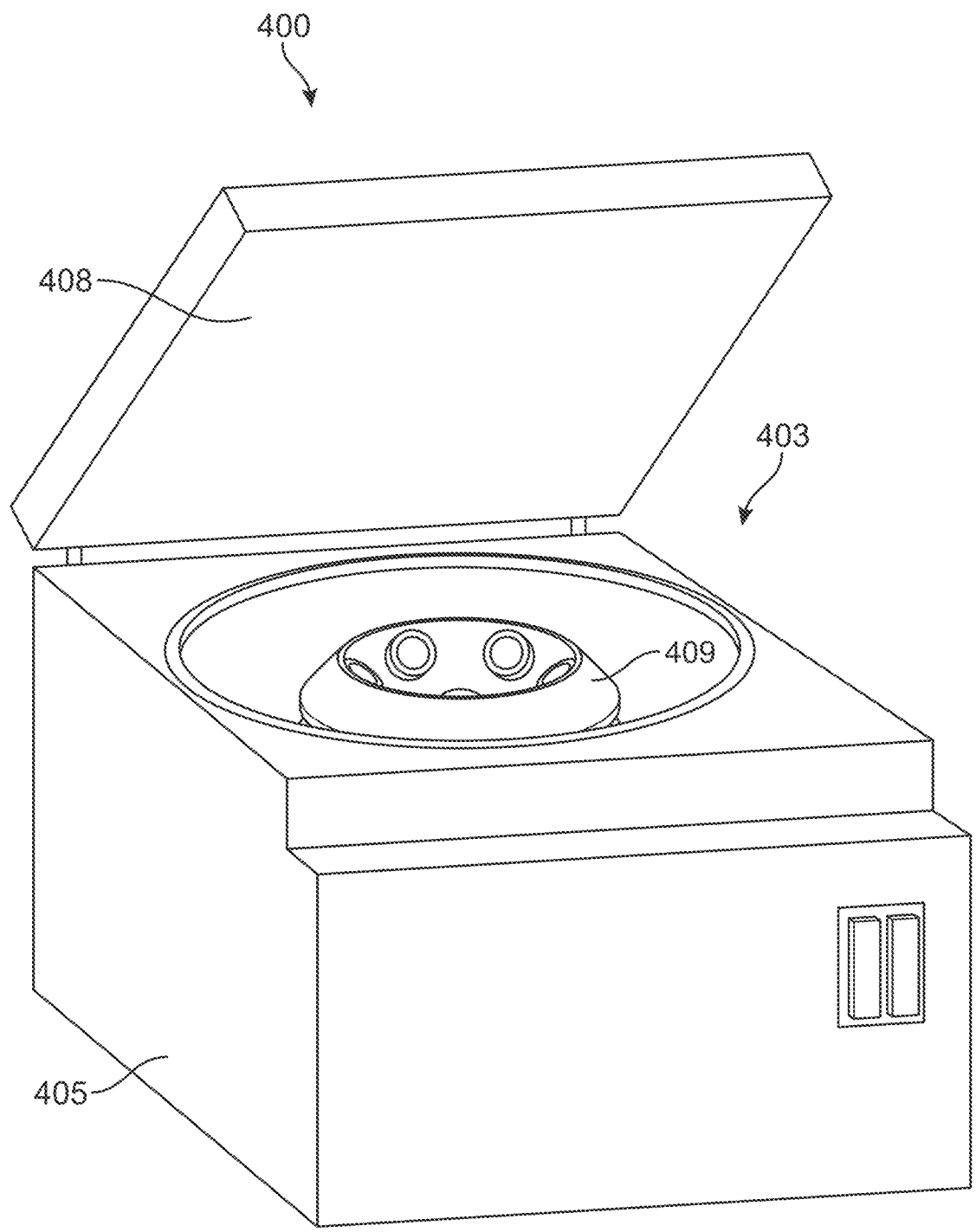
FIG. 4 is a schematic illustration of a centrifuge suitable for use in an embodiment of a method disclosed herein.

Degassed collagen then may be further degassed in a centrifuge. Centrifuge 400 is illustrated with top 408 open, making bowl 403 visible in FIG. 4. Tubes of material to be centrifuged and tubes used to ensure balance of the centrifuge are placed into the wells in the rotating bowl 409. Case 405 is sufficiently robust to contain any debris should any of the interior parts fail during use.

Figure 5:
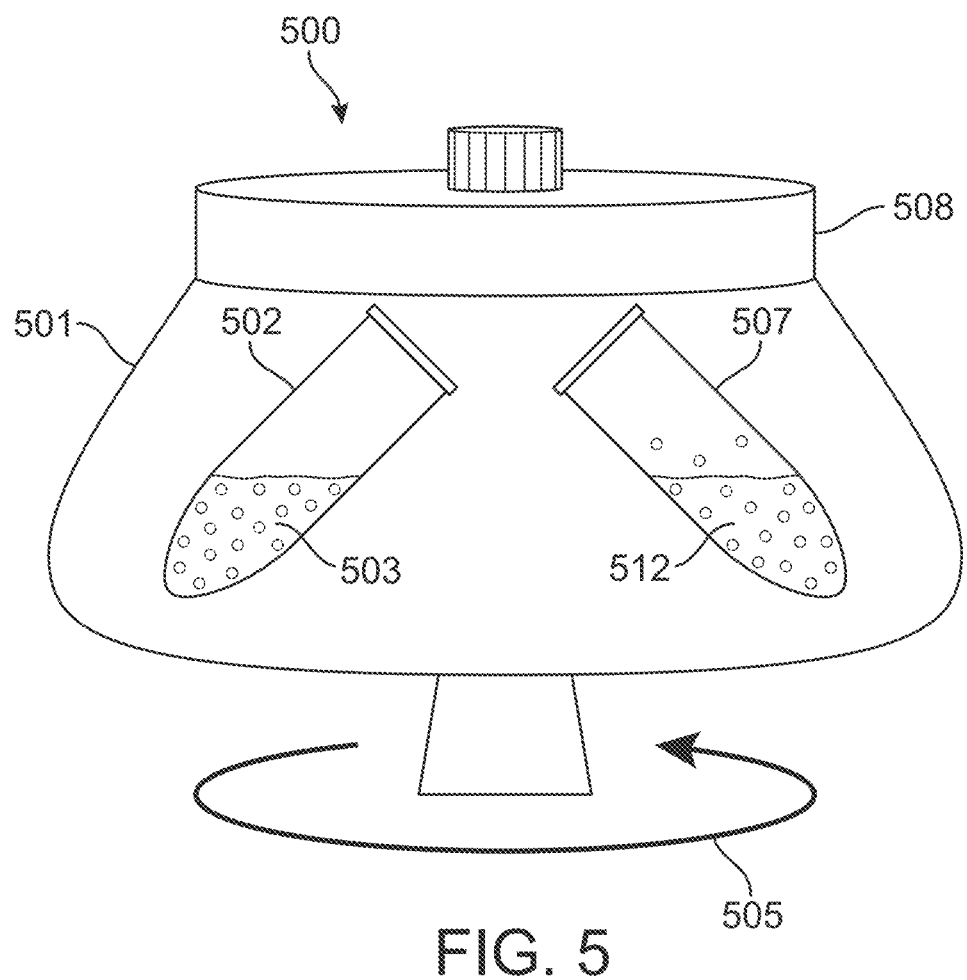
FIG. 5 is a schematic illustration of centrifuge use in an embodiment of the disclosure.

FIG. 5 illustrates centrifuge 500 having containment bowl 501 and lid 508. The centrifuge rotates rapidly counterclockwise, as illustrated by movement arrow 505. Tube 502 illustrates a tube before centrifugation containing collagen solution 503. As can be seen, the collagen solution is homogeneous and has trapped bubbles in the otherwise homogenous collagen solution 512.

Centrifugation at relative centrifugal force, or g values, between about 400 rcf and about 4,000 rcf, typically between about 600 rcf and about 1,000 rcf, and more typically between about 700 rcf and about 800 rcf, is suitable to reduce the entrapped bubble volume to essentially zero within between about 3 minutes and about 15 minutes, typically between about 4 minutes and about 10 minutes, and more typically between about 5 minutes and about 7 minutes.

In some embodiments, a pair of related steps may be repeated by alternating between the steps. For example, collagen may be processed in degasser 303 for one cycle, then in centrifuge 500 for 5 minutes, and then returned to degasser 303 for a cycle, then centrifuged again for 5 minutes. Operating in this alternative way may provide improved efficiency. This improved efficiency may be realized by taking advantage of a shorter treatment time to achieve a given quantity of bubbles or to achieve a better result than linear processing may achieve.

Collagen then is coextruded with a solution to form collagen fiber. Extrusion of collagen solution at the core of a coaxial fluid may, in some embodiments, aid formation of a collagen fiber.

Figure 6:
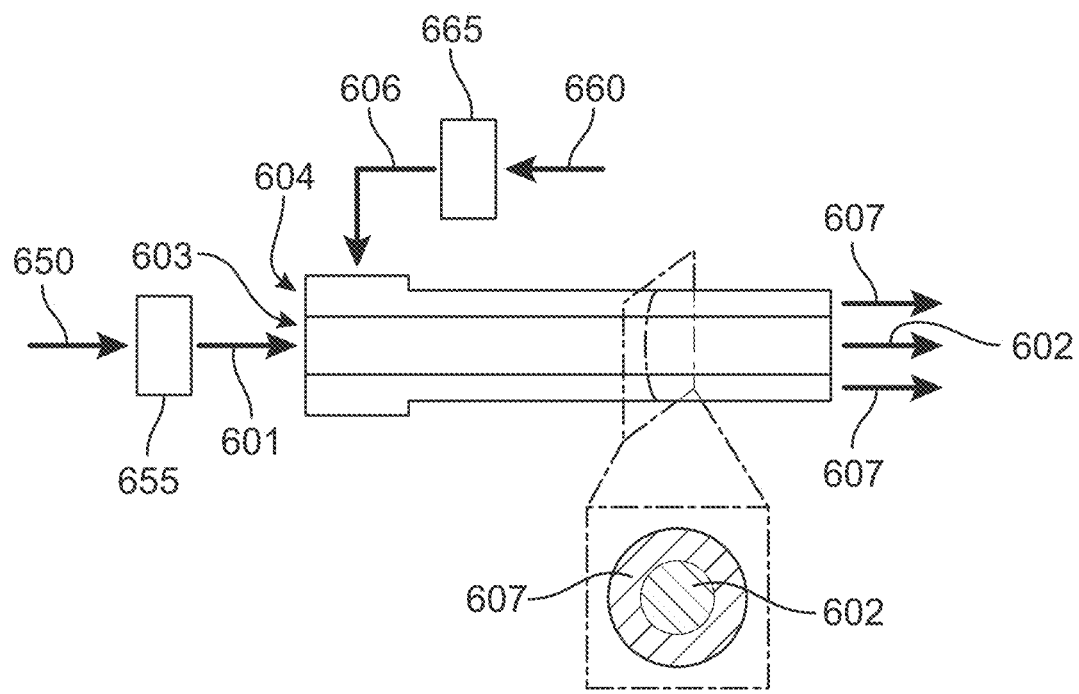
FIG. 6 is a schematic illustration of an embodiment of coaxial needles used to form collagen fiber in an embodiment.

In some embodiments of the disclosure, collagen then is introduced to the center of a coaxial flow needle, with a formation buffer solution introduced to the outer needle. Thus, the formation buffer solution forms a sheath around the collagen. As illustrated in FIG. 6, collagen solution 650 is pumped through pump 655 and introduced into inner needle 603 as collagen flow 601. Simultaneously, formation buffer solution 660 is introduced to outer needle 604 as formation buffer solution flow 606. Outer needle 604 is coaxial with inner needle 603 so that formation buffer solution forms a sheath around the central core of collagen. As the materials exit the needle to flow into a reaction zone comprising a fibril-forming bath 701 (shown in FIG. 7), formation buffer solution 607 has formed a sheath around collagen fiber 602, which begins to form as a solid fiber.

The diameter of a resultant product collagen fiber is made smaller than the inner diameter of the central needle by downstream processing. The diameter of the central needle may be larger than the target diameter of the finished fiber. In some embodiments, the inner diameter of the central needle is between about 0.05 mm and about 100 mm; in some embodiments, the inner diameter of the central needle is between about 0.1 mm and about 50 mm; in still other embodiments, the inner diameter of the central needle is between about 0.2 mm and about 20 mm; in yet other embodiments, the inner diameter of the central needle is between about 0.3 mm and about 10 mm, and more typically between about 0.35 mm and about 5 mm. In some embodiments, an even narrower range of inner diameter of the central needle, such as between about 0.03 mm and about 10 mm, typically between about 0.10 mm and about 3 mm, still more typically between about 0.30 mm and about 1 mm, and even more typically between about 0.35 mm and about 0.50 mm.

In some embodiments, the inner diameter of the central needle is between about 0.38 mm and about 0.44 mm, typically between about 0.39 mm and about 0.43 mm, and more typically between about 0.40 mm and about 0.42 mm.

In some embodiments, the inner diameter of the surrounding outer coaxial needle that supplies formation buffer solution typically is between about 1.95 times the inner diameter of the central needle and about 2.15 times the inner diameter of the central needle, typically between about 2.00 times the inner diameter of the central needle and about 2.10 times the inner diameter of the central needle, and more typically about 2.05 times the inner diameter of the central needle.

In embodiments, formation buffer solution may be any solution that aids formation of a collagen fiber. Formation buffer solution typically is a solution comprising TES, also known as 2-[(2-Hydroxy-1,1-bis(hydroxymethyl)ethyl)amino]ethanesulfonic acid or N-[Tris(hydroxymethyl)methyl]-2-aminoethanesulfonic acid, together with salts and buffering agents.

In some embodiments of the disclosure, formation buffer solution is WSB, a solution comprising 30 mM TES, 4.14 mg/mL sodium phosphate monobasic dihydrate, 12.1 mg/mL sodium phosphate dibasic heptahydrate, 135 mM NaCl, and 10 percent w/v PEG (polyethylene glycol). Similar solutions also may be suitable.

The flow rates of the collagen solution and of the formation buffer solution are adjusted so that the formation buffer solution sheath remains intact within the extrusion needles and reaction zone comprising a fibril-forming bath. The speed of the formation buffer solution also is established to be greater than the speed of the collagen solution so as to provide a stretch to the collagen fiber to improve the quality of the fiber. Indeed, in this way, the collagen will be urged to form a relatively straight, continuous fiber without kinks and other physical shape aberrations. In some embodiments, fibers may be substantially circular, ovoid, square, rectangular, ribbon-like, triangular, or irregularly shaped.

In embodiments of the disclosure, the speed of formation buffer solution in the needle reaction zone comprising a fiber-forming bath is higher than the speed of the collagen solution. Formation buffer solution is used to neutralize the collagen solution and to assist with fibrillogenesis. Further, the higher speed of the formation buffer solution is used to pull or stretch the collagen stream, which creates an extensional field that helps align the collagen monomers in a process called flow-induced crystallization. This alignment helps collagen polymerize and increases the strength of the resultant product.

In some embodiments, the volumetric flow rate of the formation buffer solution in the needle is between about 5 times the volumetric flow rate of the collagen solution in the needle and about 10 times the volumetric flow rate of the collagen solution in the needle, typically between about 7 times the volumetric flow rate of the collagen solution in the needle and about 9 times the volumetric flow rate of the collagen solution in the needle, and more typically between about 7.5 times the volumetric flow rate of the collagen solution in the needle and about 8.5 times the volumetric flow rate of the collagen solution in the needle. In particular, 8 times the volumetric flow rate of the collagen solution in the needle is effective.

Figure 7:
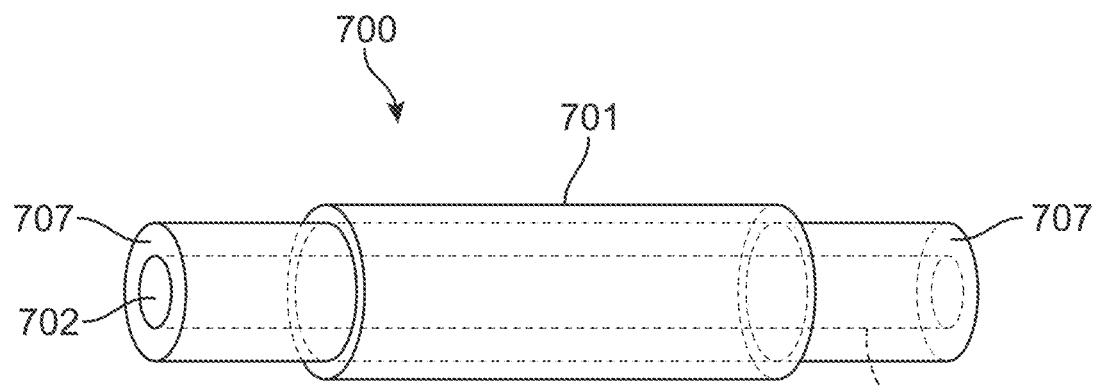
FIG. 7 is a schematic illustration of a collagen fiber reaction zone comprising a fibril-forming bath in an embodiment of the disclosure.

In embodiments, collagen stream 702 and formation buffer solution sheath 707 enter reaction zone comprising a fibril-forming bath 701 of reaction system 700, as illustrated in FIG. 7. The reaction zone may have a structure, such as a formation tube, that forms reaction zone 701. However, typically, no structure need be present. The collagen fiber continues to polymerize to form collagen fiber product as the streams flow through reaction zone comprising a fibril-forming bath 701. Collagen fiber 752 and formation buffer solution 702 flow out of reaction zone comprising a fibril-forming bath 701.

In embodiments, the speed of the collagen is adjusted to afford the collagen a reaction or polymerization time of between about 15 seconds and about 60 seconds, typically between about 20 seconds and about 50 seconds, and more typically between about 25 seconds and about 40 seconds.

Figure 8:
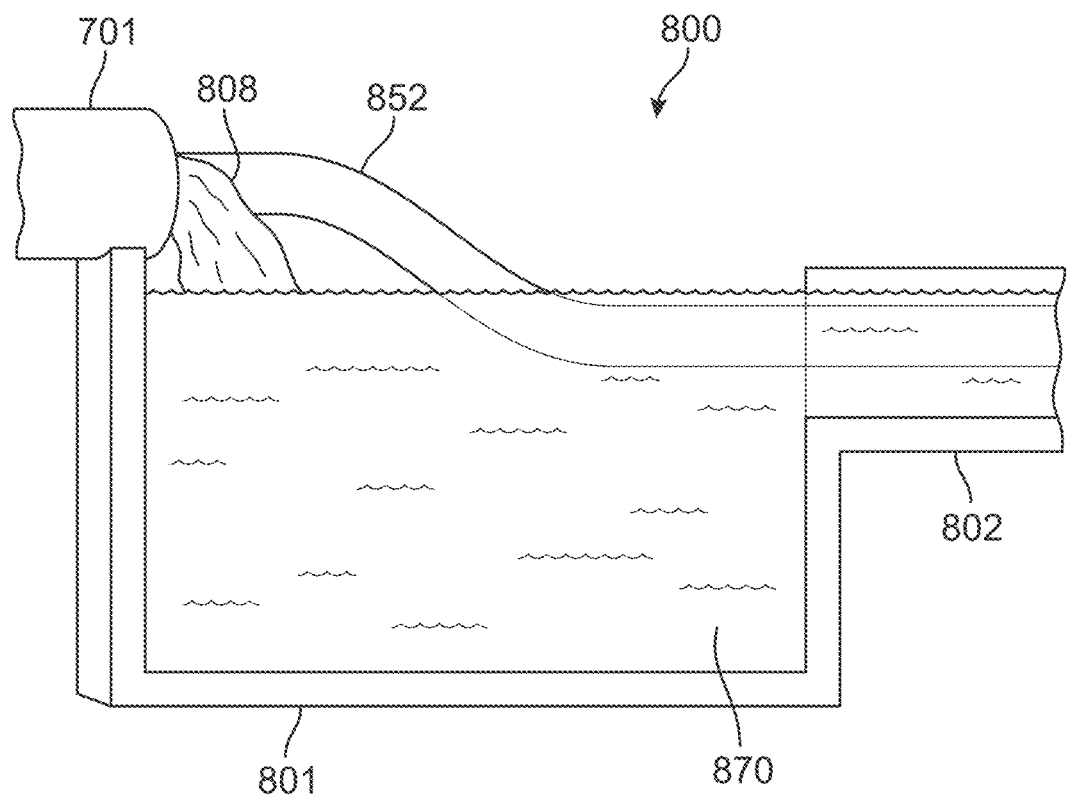
FIG. 8 is a schematic embodiment of a dehydration bath in an embodiment of the disclosure.

As shown in FIG. 8, in embodiments, at the end of the polymerization period, collagen fiber 852 has formed and separates from formation buffer solution 808 as the streams flow out of reaction zone comprising a fibril-forming bath 701. The excess formation buffer solution flows into basin 801. Dehydration system 800 is so designed as to catch formation buffer solution 808 in basin 801 and to introduce collagen fiber 852 to dehydration bath 802.

Dehydration solution affords the opportunity to remove water from the collagen fiber, reduce fiber diameter, and aid in fibrillogenesis. In embodiments, dehydration solution comprises a solution of between about 10 percent ethanol in MilliQ water and about 35 percent ethanol in MilliQ water, typically between about 15 percent ethanol in MilliQ water and about 30 percent ethanol in MilliQ water, and more typically between about 15 percent ethanol in MilliQ water and about 25 percent ethanol in MilliQ water. Skilled practitioners recognize that MilliQ water, also written as Milli-Q water, is highly purified water produced in equipment available from Millipore Sigma, Burlington, Mass. USA.

Collagen fiber 852 is passed through dehydration bath 802 for between about 10 seconds and about 50 seconds, typically between about 15 seconds and about 45 seconds, and more typically between about 20 seconds and about 40 seconds. Throughout the period, collagen fiber 852 remains submerged in dehydration bath 802. The volume of dehydration bath 802 is between about 400 times the volume of formation buffer solution pumped per minute and about 800 times the volume of formation buffer solution pumped per minute, typically between about 450 times the volume of formation buffer solution pumped per minute and about 750 times the volume of formation buffer solution pumped per minute, and more typically between about 500 times the volume of formation buffer solution pumped per minute and about 700 times the volume of formation buffer solution pumped per minute 601.

Figure 9:
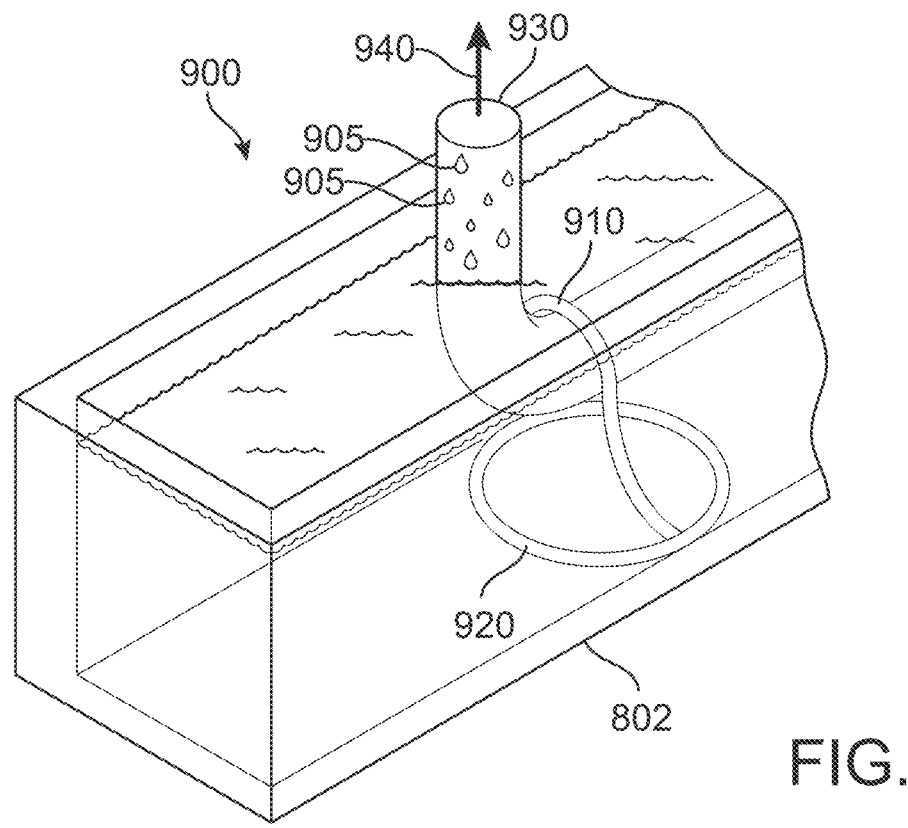
FIG. 9 is a schematic diagram of an embodiment of a device for separating collagen fiber from a dehydrating bath.

FIG. 9 illustrates the end part of the dehydration bath, from which dehydrated collagen fiber is removed from the dehydration bath. As seen in embodiments illustrated in FIG. 9, dehydrated collagen fiber 930 is removed from dehydration bath 802 at hook 910 on ring 920. As can be seen, hook 910 is retained in dehydration bath 802 by ring 920. Hook 910 tends to aid in removal of dehydration bath from the dehydrated collagen fiber. Dehydrated collagen fiber 930 is pulled upwardly in the direction of arrow 940 by rotation of spool 1001, as shown on FIG. 10. Because the collection speed of spool 1001 (FIG. 10) is greater than the extrusion flow rate of collagen fiber 930, hook 920, or a similar device, is appropriate to ensure that the collagen fiber remains submerged in the dehydration bath 802. As dehydrated collagen fiber 930 is lifted above the level of the dehydration bath, fluid droplets 905 can be seen to be falling off dehydrated collagen fiber 930.

Figure 10:
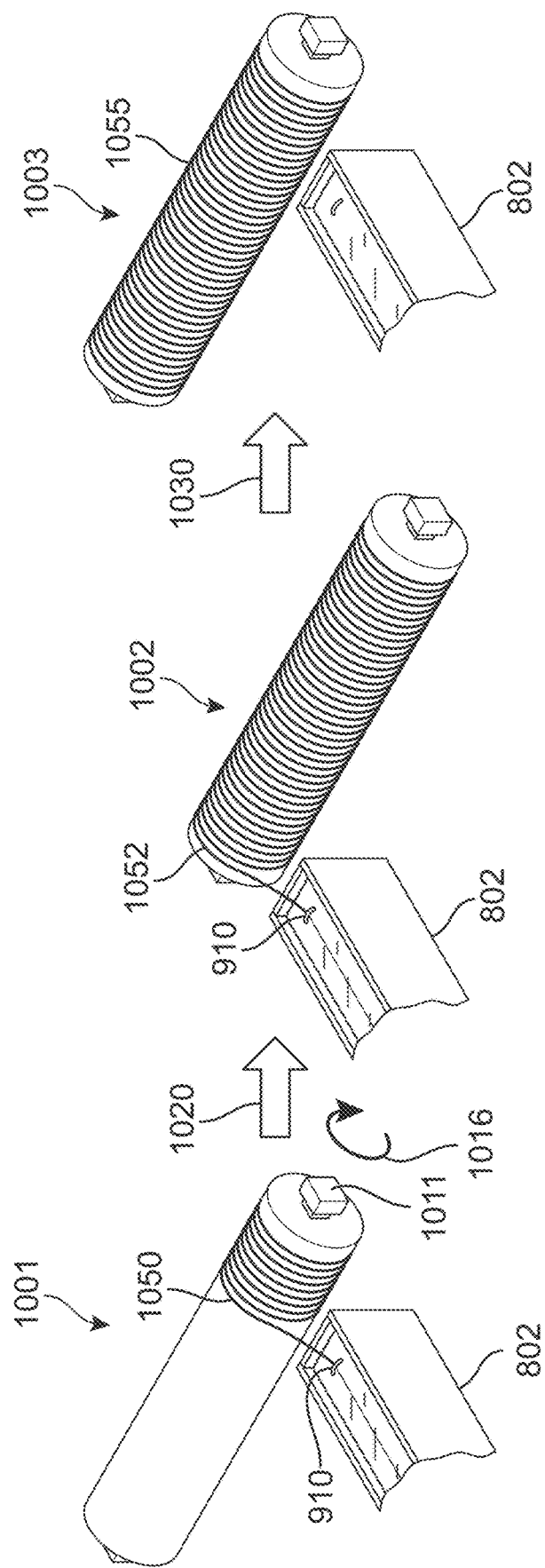
FIG. 10 is a schematic diagram of a fiber collection system in an embodiment of the disclosure.

FIG. 10 illustrates collection of dehydrated fiber onto spool 1001. In embodiments, spool 1001 is rotated by motor 1011 in a clockwise direction, as shown by arrow 1016. Spool 1001 is rotated at a speed that provides a draw ratio of between about 1.5 and about 3, typically between about 1.75 and about 2.5, and more typically between about 1.90 and 2.20. Similarly, spool 1002 is rotated at the same speed. The draw ratio is the ratio between the spooling speed and the extrusion speed. Thus, there is a tension on first collagen fiber 1050 that pulls the fiber upward at hook 910. The fiber then is pulled above the wall of dehydrating bath 802 and onto spool 1001.

Alternatively, in some embodiments of the disclosure, collagen is introduced directly into a fibril-forming bath, without the coaxial needles of FIG. 6 to form a coaxial flow illustrated in FIG. 7. Rather, collagen fiber is formed as collagen solution 852 is injected directly from a needle into fiber-forming bath 870, after which processing proceeds as with the coaxial formation method which is an alternative embodiment of the disclosure. The needle size for the collagen injection is selected in the same way the needle size is selected for the coaxial injection method, and the fiber is drawn through the fibril-formation bath and then into the dehydration bath in the same manner as other embodiments. However, spool 1001 in FIG. 10 is rotated at a speed that yields a draw speed of between about 2 times the fiber formation rate and about 4 times the fiber formation rate, typically between about 2.5 times the fiber formation rate and about 3.5 times the fiber formation rate, and more typically between about 2.75 and 3.25 the fiber formation rate. Then, post-processing is carried out in the same manner as for other embodiments.

Arrow 1020 indicates passage of time for some embodiments, during which spool 1001 has been translated relative to the position at the end of dehydration bath 802 so as to form a single layer of fiber on the spool. Thus, spool rotation continues at the same speed and fiber 1052 is kept in tension as the spool is translated until spool 1002 is essentially full. Time arrow 1030 illustrates a passage of time until the fiber supply is exhausted. Spool 1055 may then be recovered. The translational speed may be adjusted to adjust separation between fibers on a spool.

Figure 11:
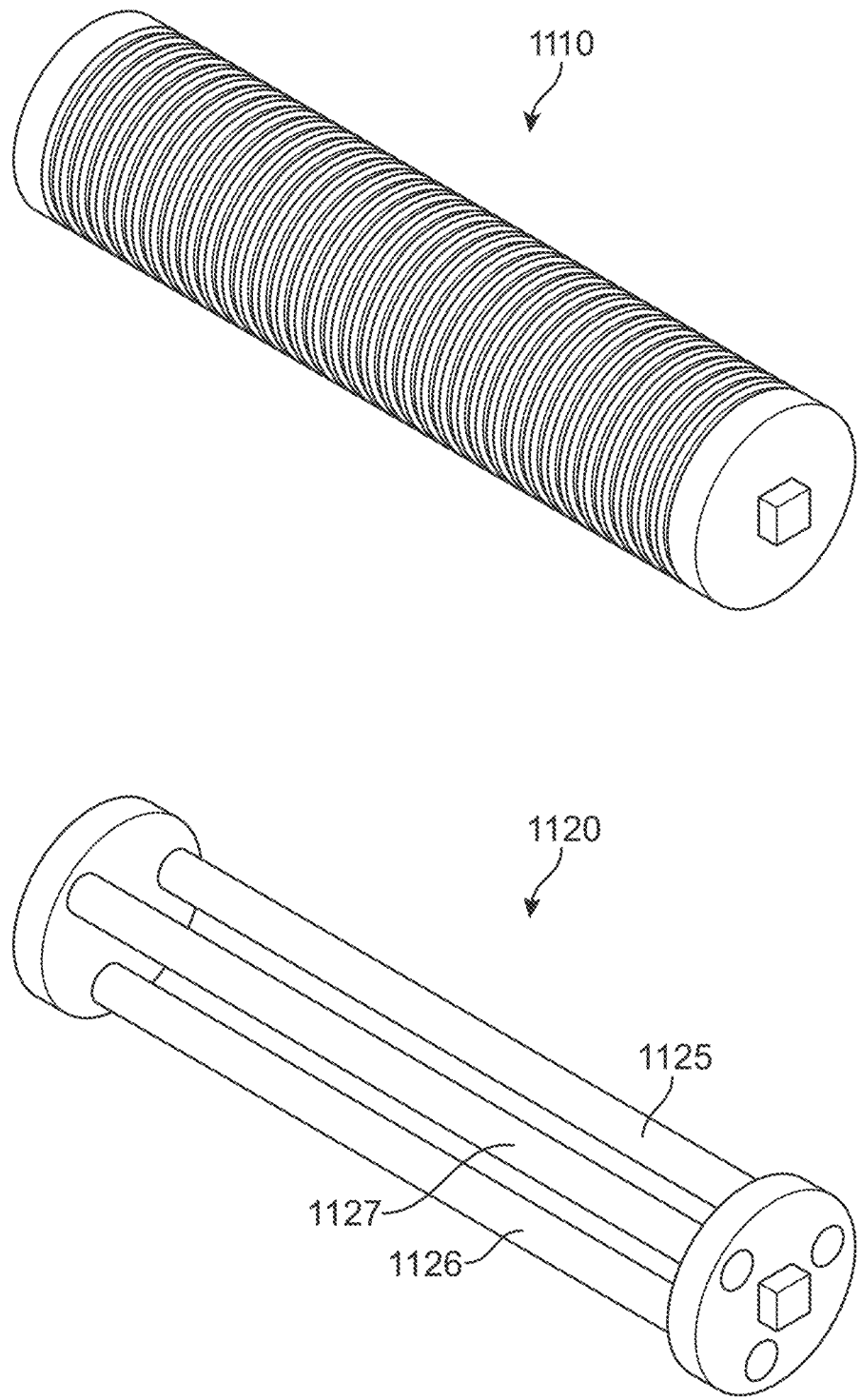
FIG. 11 is a schematic illustration of fiber collecting spools in an embodiment of the disclosure.

To ensure that tension is maintained on a fiber as the spool is rotated, typically the fiber is in contact with the entirety on the surface of a spool, such a spool 1110 used in some embodiments, as shown in FIG. 11. However, a spool need not have a continuous surface, as does spool 1110. In other embodiments, a number of rods could extend along the length of the spool. One such spool formed from rods is spool 1120 in FIG. 11, which comprises first rod 1125, second rod 1126, and third rod 1127. The rods provide sufficient surface to wind collagen thereon.

Figure 12:
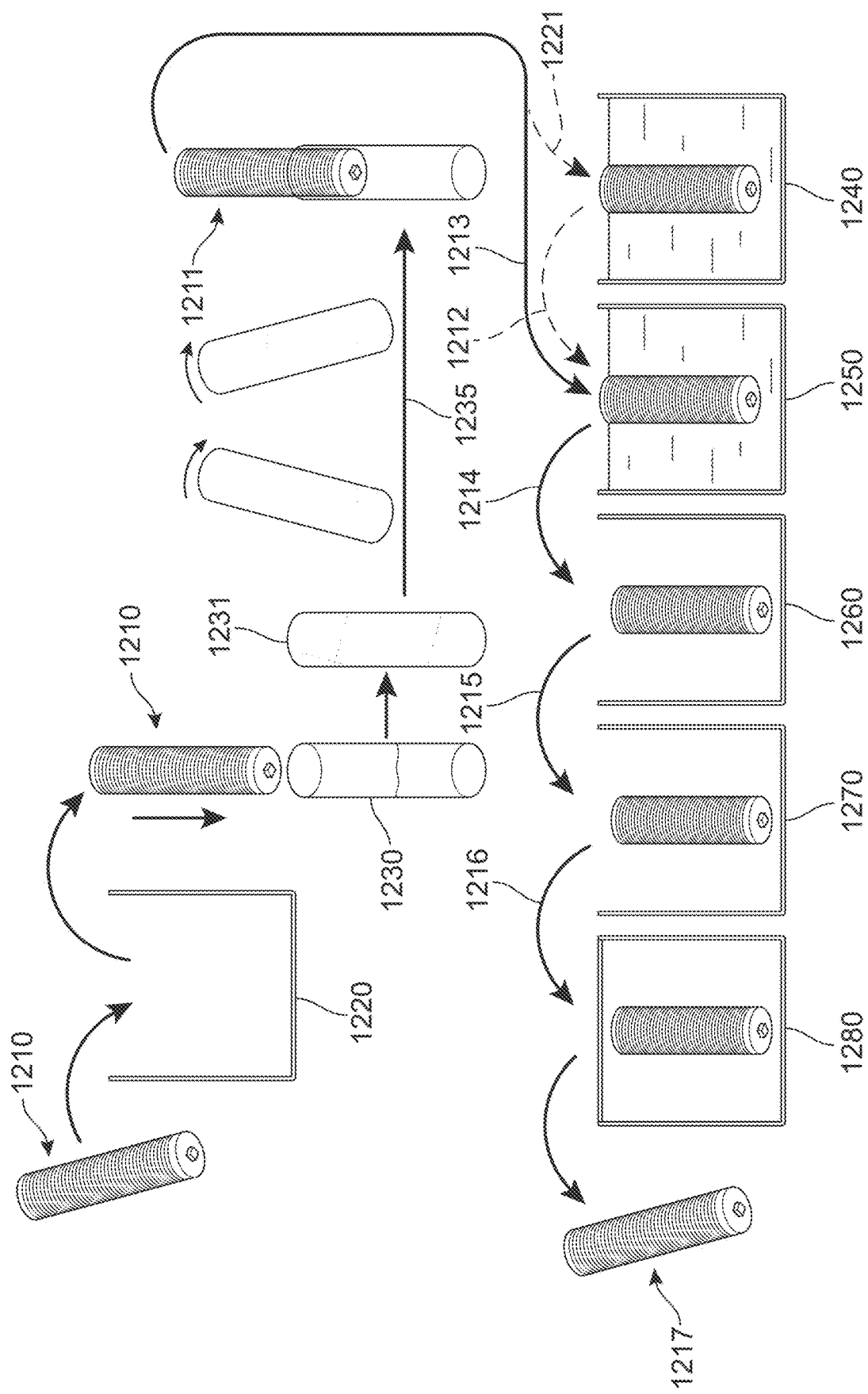
FIG. 12 is a schematic illustration of end treating in accordance with an embodiment of the disclosure.

Fibers of the disclosure also may be chemically post-processed. FIG. 12 illustrates potential post-processing steps. In embodiments, spool 1210 containing collagen fiber is air-dried at 1220 for at least about 15 minutes, typically at least about 20 minutes, and more typically at least about 30 minutes. Air-dried fiber-containing tube 1210 then is placed in a container for cross-linking. Typically, a container in embodiments of the disclosure minimizes the volume of the cross-linking container to reduce the amount of cross-linker required. Thus, as illustrated in FIG. 12, cylinder 1230 contains the amount of cross-linking fluid necessary to cover cylindrical spool 1210, as shown at 1231. In embodiments, the volume of cross-linking solution per meter of fiber is at least about 3 µL, typically at least about 4.5 µL, and more typically at least about 6 µL.

Fibers of the disclosure may be functionalized to provide amino groups, or, like collagen, may contain amino groups that can be crosslinked with aldehydes. Typically, small chain aldehydes, and more typically glyoxal (GLY) or with other conventional crosslinking reagents. For example, crosslinkers such as 1-ethyl-3-(3-dimethylaminopropyl)car-bodiimide hydrochloride (EDC), N-hydroxysuccinimide (NHS), genipin, glyceraldehyde, glutaraldehyde, o-dextran, and low M procyanidin and high M procyanidin may be used. Alternatively, if the fiber is functionalized with carboxyl groups, then EDC and other carbodiimides may be used for crosslinking. Isocyanates react with both OH groups and amines. Therefore, isocyanate-based cross-linkers may be used to crosslink the OH groups to each other within, for example, the functionalized PDLLA (linking an OH group to another OH group) to improve media stability and strength. Isocyanates also may be used to link collagen to OH groups in functionalized PDLLA via the $NH_2$ group (that is, amine group) from the collagen. Additionally, photocrosslinkers can be used.

The following reaction sequences are exemplary of cross-linking reactions available in embodiments of the disclosure. In each of the exemplary reactions, P=polymer, which is the fiber in these reactions:

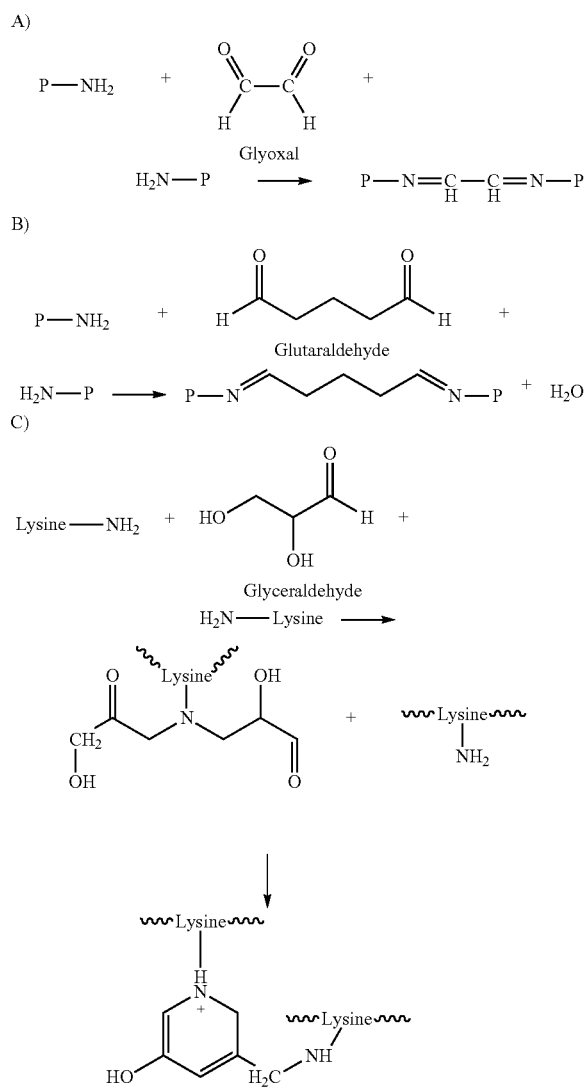

In particular, glyoxal provides suitable cross-linking in embodiments of the disclosure. In embodiments of the disclosure, a solution of 10 mM glyoxal in a solution of 70 percent ethanol and 30 percent MilliQ water is used for cross-linking. The concentrations or proportions of these components may be varied to provide the desired cross-linking degree and functionality.

In embodiments of the disclosure, 0.25 mM EDC solution in the sheath may be used as cross-linking solution.

As shown in FIG. 12, in some embodiments, tube and spool 1231 are rolled as illustrated schematically by arrow 1235. For example, the roller may roll the tube and spool at about 1 RPM. Rolling continues for a time sufficient to obtain the desired degree of cross-linking. In some embodiments, at least about 24 hours is sufficient to obtain the desired degree of cross-linking. Increasing cross-link time increases strength of bonds within the fibers and improves stability of resultant product. Thus, in some embodiments, materials are allowed to cross-link for at least about 48 hours, typically for at least about 72 hours. Cross-linking time of as much as about 1 month has been found to increase cross-link strength even more. The container may be moved in any manner that ensures that the entire coil is submersed in cross-linking fluid.

In some embodiments, the spool containing cross-linked collagen fiber 1211 then is removed from the tube and optionally is placed in a MilliQ water rinse for about 10 min, as shown at rinse tank 1240 and arrow 1221. Rinsed spool and fiber 1212 then are placed in a bath comprising 100 mM glycine 1250 for a time sufficient to deactivate excess glyoxal. Typically, 10 minutes is sufficient. Removing glyoxal helps reduce cytotoxicity of the fibers. Other cross-linking agents may be removed in a similar way, if necessary or appropriate.

In embodiments in which the rinsing step is skipped, spool and fiber 1213 are placed in glycine at glycine bath 1250. Processing to dry fiber is as in embodiments with the rinse step.

Spool containing collagen fiber 1214 from glycine bath then is again rinsed in MilliQ water at tank 1260. In embodiments, 10 minutes is sufficient to remove the glycine. Spool and fiber 1215 then are air-dried at 1270 for about an hour before being placed into a desiccating chamber 1280 for about 24 hours. Dry, flexible fibers 1217 of FIG. 12 then are recovered.

Embodiments of the disclosure are directed to a method 1300 in FIG. 13 for producing a biopolymer fiber. In the embodiments, collagen is dissolved in an acid solution 1305 to form a collagen solution 1310. In some embodiments, a compatible biopolymer is included with collagen. The collagen solution then may be degassed 1315, then centrifuged 1320 to obtain a collagen solution.

The collagen solution then is coextruded with formation buffer solution as a sheath 1325. The collagen solution is passed at a first speed through a first needle having a first diameter simultaneously with passing the formation buffer at a second speed through a second needle coaxially surrounding the first needle and having a second diameter greater than the first diameter to form a sheath around the collagen solution to form a coaxial flow. The second speed of the foundation buffer through the second needle is at least twice the first speed of the collagen solution through the first needle.

In some embodiments, the inner diameter of the central needle is between about 0.05 mm and about 100 mm; in some embodiments, the inner diameter of the central needle is between about 0.1 mm and about 50 mm; in still other embodiments, the inner diameter of the central needle is between about 0.2 mm and about 20 mm; in yet other embodiments, the inner diameter of the central needle is between about 0.3 mm and about 10 mm, and more typically between about 0.35 mm and about 5 mm. in some embodiments, an even narrower range of inner diameter of the central needle, such as between about 0.03 mm and about 10 mm, typically between about 0.10 mm and about 3 mm, still more typically between about 0.30 mm and about 1 mm, and even more typically between about 0.35 mm and about 0.50 mm.

In some embodiments, the inner diameter of the central needle is between about 0.38 mm and about 0.44 mm, typically between about 0.39 mm and about 0.43 mm, and more typically between about 0.40 mm and about 0.42 mm.

In some embodiments, the inner diameter of the surrounding outer coaxial needle that supplies formation buffer solution typically is between about 1.95 times the inner diameter of the central needle and about 2.15 times the inner diameter of the central needle, typically between about 2.00 times the inner diameter of the central needle and about 2.10 times the inner diameter of the central needle, and more typically about 2.05 times the inner diameter of the central needle.

In embodiments, formation buffer solution may be any solution that aids formation of a collagen fiber. Formation buffer solution typically is a solution comprising TES, also known as 2-[(2-Hydroxy-1,1-bis(hydroxymethyl)ethyl) amino]ethanesulfonic acid or N-[Tris(hydroxymethyl) methyl]-2-aminoethanesulfonic acid, together with salts and buffering agents.

In some embodiments of the disclosure, formation buffer solution is WSB, a solution comprising 30 mM TES, 4.14 mg/mL sodium phosphate monobasic dihydrate, 12.1 mg/mL sodium phosphate dibasic heptahydrate, 135 mM NaCl, and 10 percent w/v PEG (polyethylene glycol). Similar solutions also may be suitable.

In some embodiments, the volumetric flow rate of the formation buffer solution in the needle is between about 5 times the volumetric flow rate of the collagen solution in the needle and about 10 times the volumetric flow rate of the collagen solution in the needle, typically between about 7 times the volumetric flow rate of the collagen solution in the needle and about 9 times the volumetric flow rate of the collagen solution in the needle, and more typically between about 7.5 times the volumetric flow rate of the collagen solution in the needle and about 8.5 times the volumetric flow rate of the collagen solution in the needle. In particular, 8 times the volumetric flow rate of the collagen solution in the needle is effective.

In embodiments, the coaxially-flowing collagen and formation buffer flow through a reaction zone comprising a fibril-forming bath for a time and at speeds sufficient to form a fiber 1330. Formed collagen fiber then is separated from the formation buffer solution 1335 and put into a dehydrating solution 1340. Dehydration solution affords the opportunity to remove water from the collagen fiber, reduce fiber diameter, and aid in fibrillogenesis. In embodiments, dehydration solution comprises a solution of between about 10 percent ethanol in MilliQ water and about 35 percent ethanol in MilliQ water, typically between about 15 percent ethanol in MilliQ water and about 30 percent ethanol in MilliQ water, and more typically between about 15 percent ethanol in MilliQ water and about 25 percent ethanol in MilliQ water.

In some embodiments, the fiber is withdrawn 1345 onto a spool at a third speed greater than the first speed sufficient to increase molecular alignment and reduce the diameter of the fiber. This speed typically is at least about twice the speed at which the fiber flows through the dehydrating bath.

In other embodiments, step 1325 is skipped, and the coaxial sheath formation is not utilized. Rather, collagen solution is injected into formation buffer solution, and motivated through the formation buffer solution and the dehydrating fluid by rotating the collection spools to provide a rate that pulls the fiber at a speed between about 2 times the injection speed and about 4 times the injection speed. The remainder of the steps, including potential post-processing, then are carried out.

In embodiments, the fibers are cross-linked in step 1355 after a short air-drying period in step 1350. Typically, cross-linking is carried out in a glyoxal solution with agitation for a period sufficient to achieve cross-linking. In embodiments, the fiber is left on the spool. It is typical to minimize the volume of the cross-linking container to reduce the amount of cross-linker required.

Cross-linking material may be any suitable cross-linker. In particular, glyoxal provides suitable cross-linking in embodiments of the disclosure. In embodiments of the disclosure, a solution of 10 mM glyoxal in a solution of 70 percent ethanol and 30 percent MilliQ water is used for cross-linking. The concentrations or proportions of these components may be varied to provide the desired cross-linking degree and functionality. In embodiments, the volume of cross-linking solution per meter of fiber is at least about 3 µL, typically at least about 4.5 µL, and more typically at least about 6 µL. A 24 hour cross-linking period often is suitable to achieve the amount of cross-linking. However, typically, a cross-linking period of at least about 48 hours provides increased cross-linking, and a period of at least about 72 hours provides even more cross-linking.

The spool containing cross-linked collagen fiber then is removed from the cross-linking container and, in some embodiments of the disclosure, is placed in a MilliQ water rinse for about 10 minutes. In other embodiments, the spool need not be rinsed. Spool and fiber then are placed in a bath comprising 100 mM glycine bath step 1360 for a time sufficient to deactivate excess glyoxal. Typically, 10 minutes is sufficient. Removing glyoxal may help reduce cytotoxicity of the fibers.

Other processing steps may be taken if glyoxal is not used as the cross-linking agent. The skilled practitioner will recognize appropriate post-processing steps appropriate for these other cross-linking systems.

In embodiments, the spool containing collagen fiber from the glycine bath then is again rinsed in MilliQ water at step 1365. In embodiments, 10 minutes is sufficient to remove the glycine. Spool and fiber 1214 then are air-dried at step 1270 for about an hour before being placed into a desiccating chamber 1370 for about 24 hours. Dry, flexible fibers are recovered.

In embodiments of the disclosure, the fiber produced is a biopolymer fiber comprising collagen. The biopolymer fiber has one or more of the following characteristics:

an ultimate tensile strength of between about 20 MPa to about 170 MPa;

a modulus of elasticity of between about 200 MPa to about 3,500 MPa;

a strain at break of between about 4 percent and about 12 percent elongation;

an average fiber diameter between about 16 µm and about 70 µm after drying; and at least maintains its strength after soaking in biological fluid for about 1 hour.

The fiber exhibits an ordered, longitudinally-oriented structure, and the fiber allows infiltration of cellular growth.

In another aspect, the disclosure is directed to an implantable biopolymer scaffold for supporting repair of a soft tissue injury, or for repair or replacement for a human body part. The scaffold comprises at least one biopolymer sheet comprising biopolymer fibers, wherein the biopolymer comprises collagen and the biopolymer fibers have one or more of the following characteristics:

an ultimate tensile strength of between about 20 MPa to about 170 MPa;

a modulus of elasticity of between about 200 MPa to about 3,500 MPa;

a strain at break of between about 4 percent and about 12 percent elongation;

an average fiber diameter between about 16 µm and about 70 µm after soaking for about 1 hour in phosphate-buffered saline solution; and at least maintains its strength after soaking in biological fluid for about 24 hours.

The fiber exhibits an ordered, longitudinally-oriented structure, and allows infiltration of cellular growth. The sheet comprises fibers arranged in a typical way for convenience of handling during use. For example, a single fiber would be exceedingly difficult to use because of the small diameter. Thus, it is necessary or appropriate to form scaffolds, or structures larger than a single fiber, to provide fiber-containing products suitable for repair or replacement of a body part. Thus, for example, it is possible to braid several fibers together to form a strand comprising collagen fibers. Such a strand may be useful, for example, to oversew a rupture in a ligament or tendon. These and other uses will become apparent to the user.

Throughout the disclosure, testing of properties and characteristics is carried out on 10 randomly-gathered fibers. Strength tests are carried out with 10 fibers and a load of between about 0.3 N and about 2 N.

As noted herein, the stability of the collagen fiber is at least maintained, even after 1 hour in biologic solution. Further, additional cross-linking achieved by continuing the cross-linking period to at least about 48 hours, and even further to 72 hours, significantly reduces swelling of the fiber and maintains or increases load capacity.

The following example is an example of an embodiment of the disclosure and is not meant to be limiting in any way.

Example 1

Collagen, type I bovine, with telopeptide ends intact, was removed from packaging, and was combined with 0.05 M acetic acid to create a viscous solution having a collagen concentration of 16 mg/mL. The solution was allowed to dissolve collagen for 16 hours before being degassed for several cycles. Excess bubbles were removed by centrifuging at about 750 rcf before and after degassing for 5 minutes. Collagen was aspirated into a 5 mL syringe and then attached to the center luer fitting of a coaxial needle (0.41 mm ID for collagen inlet and 0.84 mm ID for formation buffer inlet). The collagen syringe and coaxial needle were then placed onto a syringe pump to be pumped at 60 µL/min.

The pH of formation buffer solution was adjusted to 8.0±0.1 and placed into a covered beaker. The formation buffer solution was WSB, also known as wet spinning buffer, a solution comprising 30 mM TES, 4.14 mg/mL sodium phosphate monobasic dihydrate, 12.1 mg/mL sodium phosphate dibasic heptahydrate, 135 mM NaCl, and 10 percent w/v PEG (polyethylene glycol).

Tubing was placed at the bottom of the beaker and through a peristaltic pump and then attached to the outer coaxial needle via a luer fitting, thus creating the outer sheath flow for the collagen. Formation buffer was used to neutralize the collagen solution and to assist with fibrillogenesis. Formation buffer solution was flowed at 500 µL/min. The faster formation buffer was also used to pull or stretch the collagen stream and created an extensional field that helps align the collagen monomers in a process called flow-induced crystallization. This alignment helped collagen polymerize more readily and increased the strength of the end product.

The collagen and formation buffer streams entered the reaction zone comprising a fibril-forming bath, in which the fiber had time to polymerize and form a long chain. The reaction zone comprising a fibril-forming bath ends at the inlet of a dehydration bath that caught the used formation buffer in a reservoir and allowed the fiber to travel roughly 45 cm through 20% ethanol and 80% MilliQ water. This bath helped remove water from the collagen fiber, reduced its diameter, and aided in fibrillogenesis. The bath was 2.5 cm wide and held roughly 300 mL of solution.

After the fiber traveled through the bath, it was then spooled onto a 50 mm diameter spool that was 300 mm long and rotated at roughly 5 RPM, thus creating a draw ratio of approximately 2 (ratio between spooling speed and extrusion speed). This draw ratio helped further increase the molecular alignment and reduced fiber diameter which ultimately increased strength. Translational speed of the spool was adjusted to alter the spacing between fibers.

The spools were allowed to air dry for at least 15 minutes before being placed into a cylindrical tube for crosslinking. The inner diameter of this tube was close to the outer diameter of the spool to reduce the amount of crosslinker required for full submersion. One-hundred twenty mL of 10 mM glyoxal in 70% ethanol and 30% MilliQ water was prepared and poured into the tube. The spool then was put into the tube. The tube and spool then were placed on a roller at approximately 1 RPM for 24 hours.

After 24 hours, the spool was removed from the tube and placed in a MilliQ bath for 10 minutes. The spool was then placed in a bath of 100 mM glycine for 10 minutes to deactivate any excess glyoxal to help reduce cytotoxicity, followed by a final bath of MilliQ water for 10 minutes to remove any remaining glycine. The spool and fibers then were air dried for approximately an hour before being placed into a desiccating chamber for 24 hours.

After desiccation, the fibers were dry and flexible which makes them easily manipulated into useful shapes for building scaffolds. Resulting fibers had an average diameter of 25 µm and a tensile strength of approximately 100 MPa after a half hour soak in PBS. PBS, also known as phosphate-buffered saline, is a buffer solution commonly used in biological research. It is a water-based salt solution containing disodium hydrogen phosphate, sodium chloride, and, in some formulations, potassium chloride and potassium dihydrogen phosphate. The buffer helps to maintain a constant ph. The osmolarity and ion concentrations of the solutions match those of the human body (i.e., are isotonic).

Stability testing for 7 days in DMEM, a synthetic cell culture medium comprising amino acids, calcium chloride, potassium chloride, magnesium sulfate, sodium chloride, and monosodium phosphate, glucose, and vitamins folic acid, nicotinamide, riboflavin, and $B_{12}$, at 37° C. shows a loss of approximately 25% original strength. DMEM also contains iron and phenol red for pH indication.

This example illustrates production of fiber within the scope of the claims in accordance with a method within the scope of the claims. The fiber will produce scaffolds, in accordance with the claims, for repair or replacement of human body parts.

Example 2

Collagen, type I bovine, with telopeptide ends intact, was removed from packaging, and was combined with 10 mM hydrochloric acid to create a viscous solution having a collagen concentration of 16 mg/mL. The solution was allowed to dissolve collagen for 16 hours before being centrifuged at 733 rcf for 5 minutes. Excess bubbles are removed by degassing for 2 minutes, and then centrifuging again at 733 rcf for 10 minutes. Collagen was aspirated into a 20 mL syringe and then attached to the center luer fitting of a coaxial needle (0.41 mm ID for collagen inlet). The collagen needle was then placed onto a syringe pump to be pumped at 50 μL/min.

The pH of formation buffer solution was adjusted to 8.0±0.1 and placed into a long bath. The formation buffer solution was WSB, also known as wet spinning buffer, a solution comprising 30 mM TES, 4.14 mg/mL sodium phosphate monobasic dihydrate, 12.1 mg/mL sodium phosphate dibasic heptahydrate, 135 mM NaCl, and 10 percent w/v PEG (polyethylene glycol).

Formation buffer was used to neutralize the collagen solution and to assist with fibrillogenesis. Collagen was pumped into the formation buffer solution and is guided through the bath. The collagen formation buffer solution comprises the reaction zone, in which the fiber had time to polymerize and form a long chain. The reaction zone comprising a fibril-forming bath ends at the inlet of a dehydration bath of 20% ethanol and 80% MilliQ water through which the fiber is guided. This bath helped remove water from the collagen fiber, reduced its diameter, and aided in fibrillogenesis. Both baths were 2.5 cm wide and held roughly 300 mL of solution.

After the fiber traveled through the baths, it was then spooled onto a 50 mm diameter spool that was 300 mm long and rotated at roughly 10 RPM, thus creating a draw ratio of at least approximately 2 (ratio between spooling speed and extrusion speed). This draw ratio helped further increase the molecular alignment and reduced fiber diameter which ultimately increased strength. Translational speed of the spool was adjusted to alter the spacing between fibers.

The spools were allowed to air dry for at least 15 minutes but no more than 1 hour before being placed into a cylindrical tube for crosslinking. The inner diameter of this tube was close to the outer diameter of the spool to reduce the amount of crosslinker required for full submersion. One-hundred twenty mL of 10 mM Glyoxal in 70% ethanol and 30% MilliQ water was prepared and poured into the tube. The spool then was put into the tube. The tube and spool then were placed on a roller at approximately 1 RPM for at least 24 hours and up to 72 hours.

After 24 or up to 72 hours, the spool was removed from the tube and air dried for approximately an hour before being placed into a desiccating chamber for 24 hours.

After desiccation, the fibers were dry and flexible which makes them easily manipulated into useful shapes for building scaffolds. Resulting fibers had an average wet diameter of 30 μm and a tensile strength of approximately 120 MPa after a half hour soak in PBS. PBS, also known as phosphate-buffered saline, is a buffer solution commonly used in biological research. It is a water-based salt solution containing disodium hydrogen phosphate, sodium chloride, and, in some formulations, potassium chloride and potassium dihydrogen phosphate. The buffer helps to maintain a constant pH. The osmolarity and ion concentrations of the solutions match those of the human body (i.e., are isotonic).

Stability testing for 7 days in DMEM, a synthetic cell culture medium comprising amino acids, calcium chloride, potassium chloride, magnesium sulfate, sodium chloride, and monosodium phosphate, glucose, and vitamins folic acid, nicotinamide, riboflavin, and $B_{12}$, at 37° C. shows a loss of approximately 25% original strength. DMEM also contains iron and phenol red for pH indication.

This example illustrates production of fiber within the scope of the claims in accordance with a method within the scope of the claims. The fiber will produce scaffolds, in accordance with the claims, for repair or replacement of human body parts.

Additional Disclosure and Comparative Information

In embodiments of the disclosure, clinical-grade atelocollagen and telocollagen may be used to form microfluidics extruded collagen microfibers which then can be crosslinked with biological and benign crosslinkers such as glyoxal or DL-Glyceraldehyde (DLG). These cross-linked fibers demonstrated hydrated ultimate tensile strength near 300 MPa and modulus over 3 GPa, significantly stronger than 50 other crosslinking strategies tested and exceeding native human Achilles tendon and anterior cruciate ligament strength. Glyoxal cross-linked fibers further retained 50% of the initial load-bearing capacity through 3-6 months in culture. Collagen fibers implanted in rats demonstrated biocompatibility, promoted the production of new, host-generated aligned collagen growing along the fibers, and in the case of glyoxal crosslinking, promoted an elevated pro-regenerative M2 macrophage response. Embodiments of the disclosure demonstrate marked improvements in healing compared with other crosslinked fibers comprising conventional and synthetic materials, making embodiments of the disclosure superior fibers for generating strong collagen sutures or use as a device for ligament, tendon, or other soft tissue repairs.

Attempts to create materials suitable for tendon and ligament repairs have yet to produce a suitable product. To date, autografts, allografts, and synthetic materials as sutures, braces, or grafts for soft tissue closure or joining, for example, have been found to have significant clinical limitations. Allografts such as dead, decellularized, and chemically treated implants, can be slow to integrate, inflammatory, and may possibly delay healing (Seon, Song and Park, 2006). Synthetic grafts can break down into acidic byproducts damaging surrounding tissue (Taylor et al., 1994; van Sliedregt et al., 1994; Matsusue et al., 1995). Synthetic grafts often do not match the mechanical or material properties of tendons or ligaments (Hogan et al., 2015), which may lead to generation of stress risers and creation of a debilitating non-isometry if used in a joint space. Autografting extends surgery time and associated trauma (e.g. blood loss, risk of infection) due to the need for a second procedure to recover the autologous tissue, causing additional trauma in the process (Chen et al., 2009; Perrone et al., 2017). Joint reconstruction with autografting or allografting further results in a higher incidence and severity of premature osteoarthritis, thus affecting the quality of life (Leiter et al., 2014; Smith et al., 2014; Perrone et al., 2017). Rising rates of post-traumatic osteoarthritis has become a significant problem for military veterans (Showery et al., 2016).

There remains an unmet need in manufacturing an ideal biological, strong, material for tendon and ligament repair sutures and for resorbable sutures. Synthetic non-resorbable suture with collagen-coating (e.g. Collagen-Coated FiberWire®) has been made available in an attempt to improve biocompatibility, reduce inflammation, and reduce abrasiveness from the strong synthetic materials, particularly for orthopedic indications.

Crosslinked fibers extruded from type I collagen may produce strong product. However, these products are unsatisfactory and present biological, strength, and other objections. For example, most crosslinkers are cytotoxic, use harsh chemicals foreign to the body, and are also not used in currently marked U.S. Food and Drug Administration (FDA) approved or cleared products, making their use more challenging for clinical translation. In addition to their potential use in augmenting ACL or AT repair, braided collagen fibers have the potential to be used as sutures for general, ocular, and plastic and cosmetic surgery if shown to have high uniform tensile properties, consistent uniform diameters, biocompatibility and controllable resorption with regenerative capacity.

Embodiments of the disclosure are directed to a novel microfluidic-extrusion system to produce microfibers of clinical type I collagen as filaments and as thin ribbon-like structures. Embodiments of the disclosure satisfy rigorous mechanical, biochemical, cytocompatibility, and biocompatibility criteria, making fiber embodiments of the disclosure having properties specifically for biomedical use. Embodiments of the disclosure exhibiting order from the molecular-scale through mesoscale and up to macroscales required to produce useful products, these collagen fibers disclosed herein have potential applications in tendon and ligament repair, wound closure, and other indications where an advanced collagen-suture-based biomaterial may be beneficial across the fields of surgery in medicine.

Figure 14:
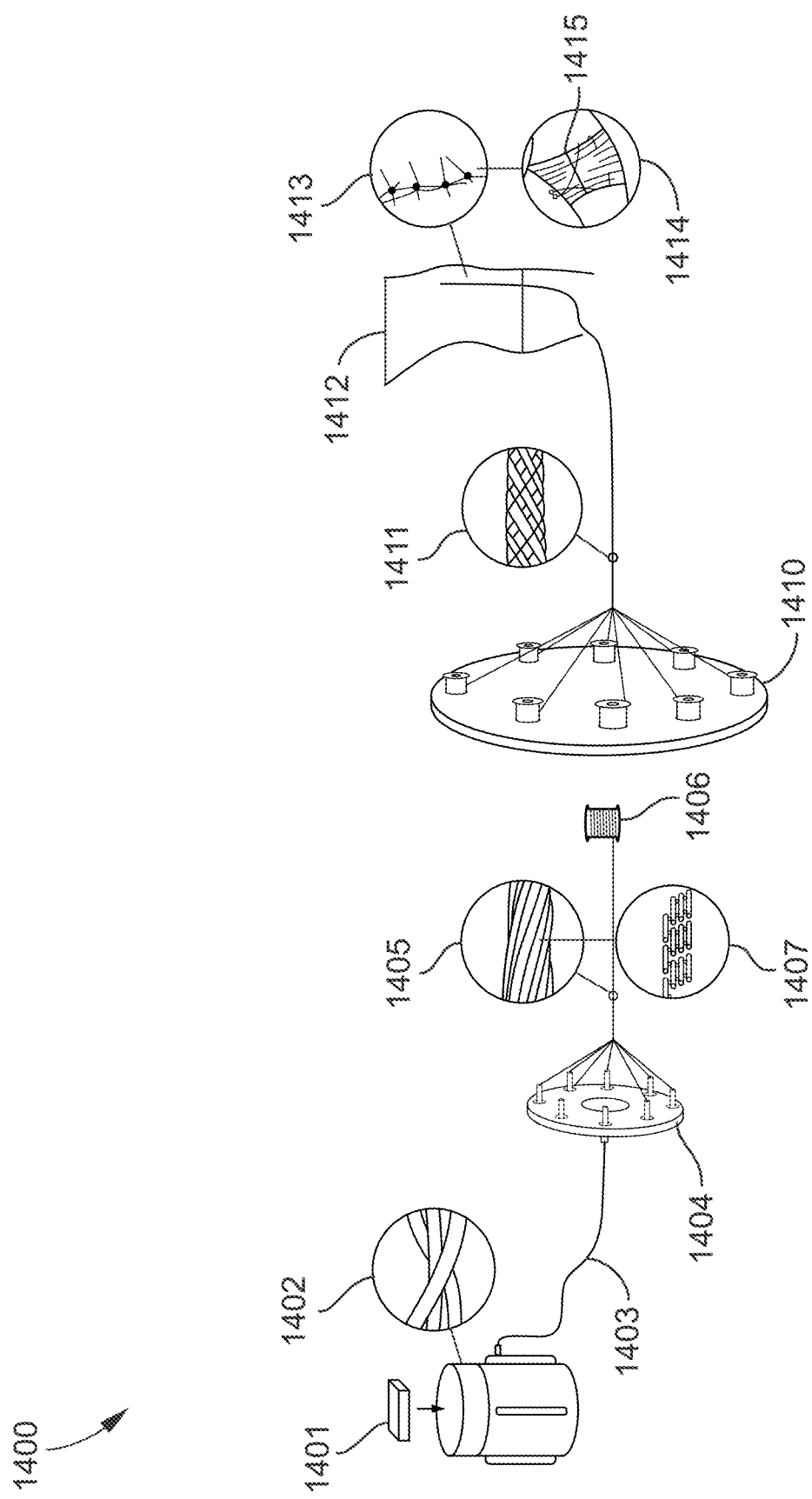
FIG. 14 is a schematic illustration of a method of an embodiment of the disclosure.

FIG. 14 illustrates schematically manufacture of collagen microfiber in accordance with embodiments of the disclosure, and potential biomedical applications of suitable products. Freeze-dried collagen is dissolved in acid in step 1401, wherein collagen molecules 1402 are obtained. Extruded microfibers 1403 are twisted in spinneret 1404 to form twisted microfibers 1405. The microfibers comprise assembled molecular collagen 1406. The collagen may be spooled at step 1407.

Collagen may be more suitably used in three-dimensional structures formed by twisting or braiding individual fibers. Braided fibers 1411 or twisted fibers 1405 then may be used to suture tear 1415 in an anterior cruciate ligament (ACL) in knee 1412 of a patient. Collagen ACL sutures 1414 are used to repair the tear, and collagen skin sutures 1415 may be used to close the wound.

Any number of fibers may be associated, whether twisted or not, to form a bundle, and bundles may be assembled into larger bundles. For example, bundles may comprise between 2 fibers and about 10,000 fibers, or between about 4 fibers and about 6,000 fibers, typically between about 8 fibers and about 4,000 fibers, and more typically between about 12 fibers and about 2,000 fibers. Then, bundles may be combined, by twisting or otherwise, to form larger bundles. Bundles that are combined need not have equal numbers of fibers.

Bundles may be described by the number of fibers in the bundle. For example, a 5-fiber bundle may be called a penta-fiber; 8 fibers would produce an octa-fiber, and so on. Systems and equipment with other numbers of nozzles or extruders may be used to produce such bundles.

Figure 15:
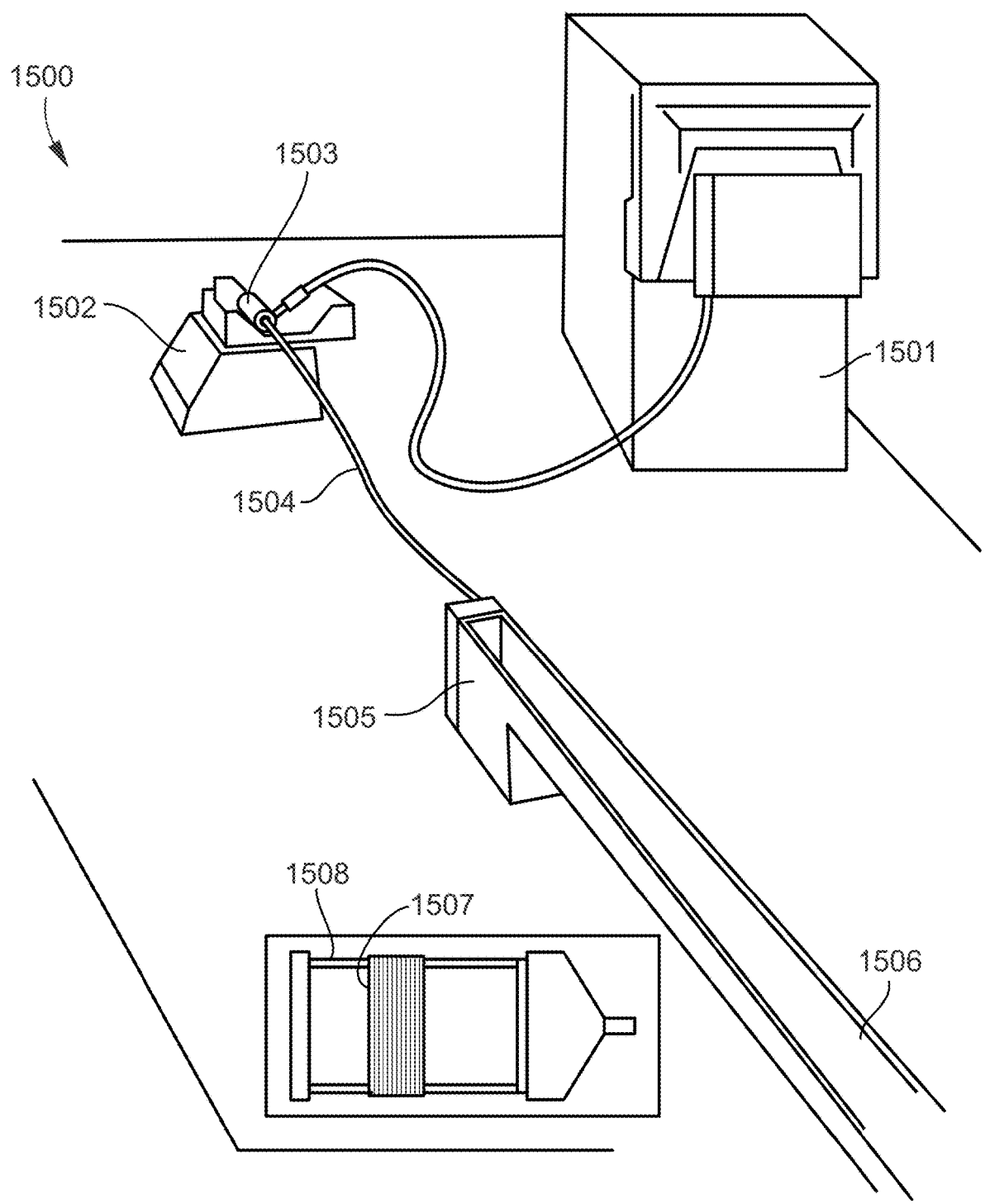
FIG. 15 is a schematic illustration of an embodiment of an apparatus suitable for use to make product of the disclosure.
Figure 16:
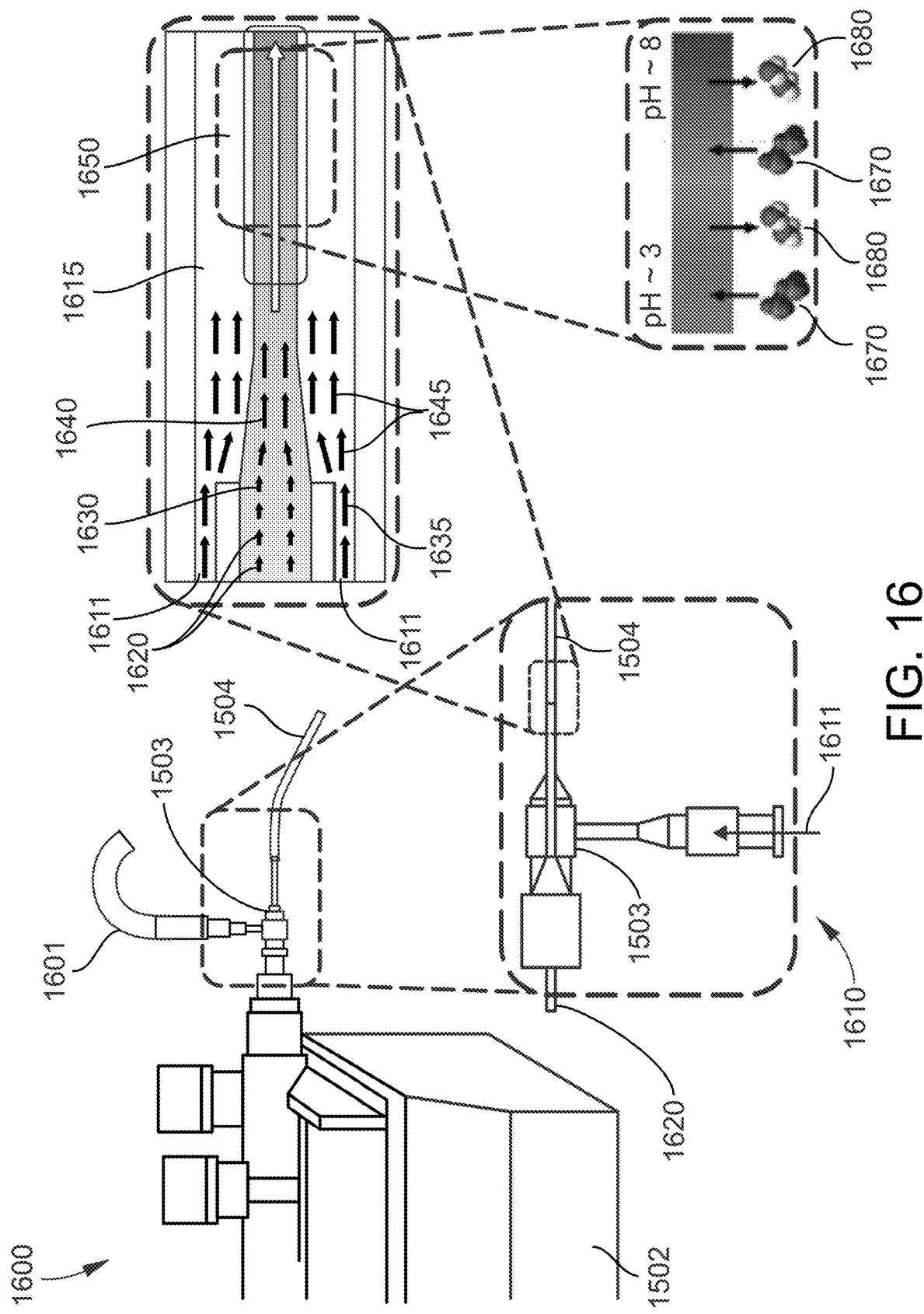
FIG. 16 illustrates additional details of the apparatus of FIG. 15.

FIG. 15 and FIG. 16 illustrate a method for obtaining collagen fiber and a system in which the reactions can be carried out. In embodiments of the disclosure, up to 2% (w/v) clinical grade lyophilized telocollagen (Telo) or atelocollagen (Atelo) (Collagen Solutions, CA) or methacrylated collagen (Advanced BioMatrix, CA) was dissolved in up to 0.05 M acid (most typically acetic or hydrochloric) overnight by agitation. As shown in system 1500, acidified collagen 1501 was then pumped through the center of a nozzle system. The system may include coaxially arranged conduits or needles 1503. Neutralizing alkaline formation phosphate buffer containing salts (Sodium chloride, Sodium Phosphate Dibasic, Sodium Phosphate Monobasic, and N-Tris(hydroxymethyl)methyl-2-aminoethanesulfonic acid) and PEG (polyethylene glycol) was pumped 1501 through the system in the outer portion of the coaxial conduit 1503. The formation buffer ran at a volumetric flow rate that is between about 5 times and about 20 times, typically between about 8 times and 15 times, and most typically about ten times the rate at which collagen was introduced, which causes the protein to be extended and partially aligned, imparting mechanical strength to the resulting fiber 1504. The fiber became more solid as it passed through the formation tube before entering a bath 1505 of 20% aqueous ethanol. In addition to dehydrating the fiber, this bath helped remove residual formation buffer thus contributing to improved strength and stability of the resultant collagen microfiber. After dehydration 1506, the microfiber 1507 may collected on two-bar device 1508. Other suitable collections devices also can be used.

In some embodiments, acidified collagen fibers may be formed by extrusion before entering the formation bath. For example, acidified collagen fibers may be formed by use of spinneret 1404. In some embodiments, a plurality of syringes of acidified collagen may be formed simultaneously.

Figure 46:
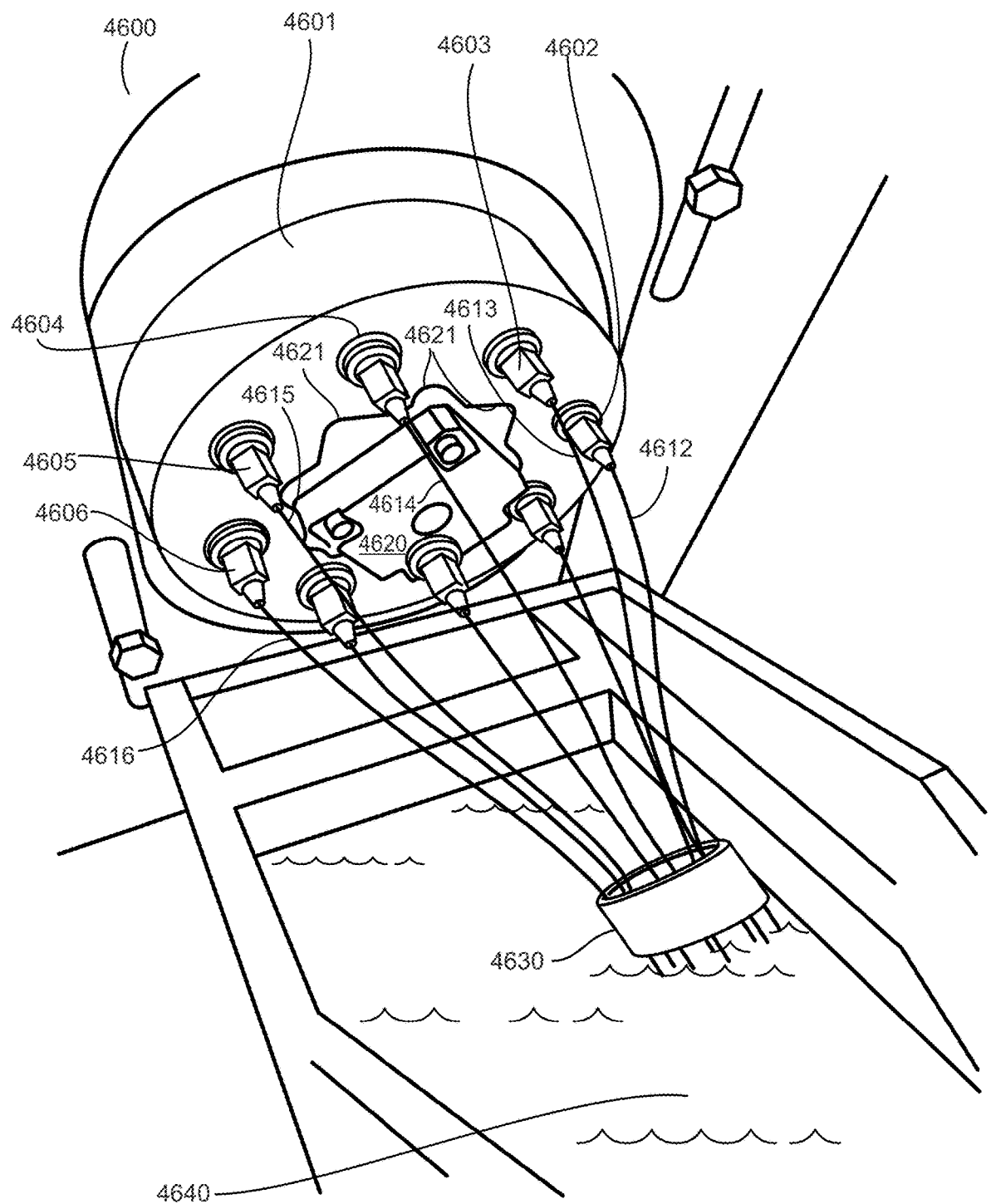
FIG. 46 illustrates an embodiment of a method of the disclosure.
Figure 52:
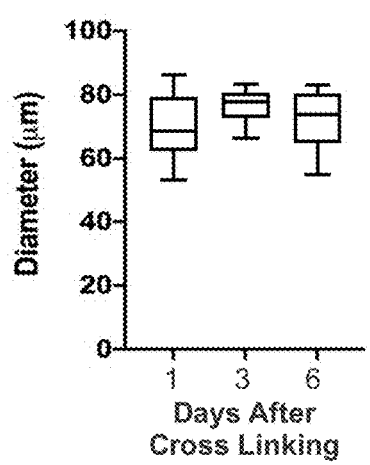
FIG. 52 summarizes the properties and characteristics of an embodiment of the disclosure.
Figure 53:
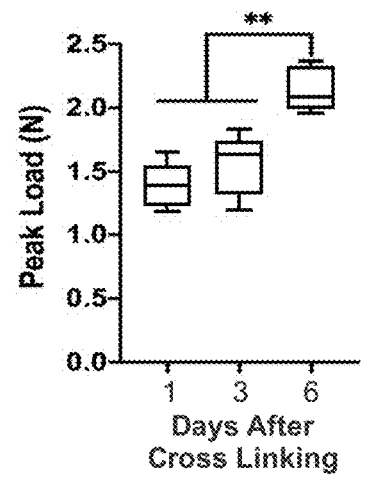
FIG. 53 summarizes the properties and characteristics of an embodiment of the disclosure.
Figure 54:
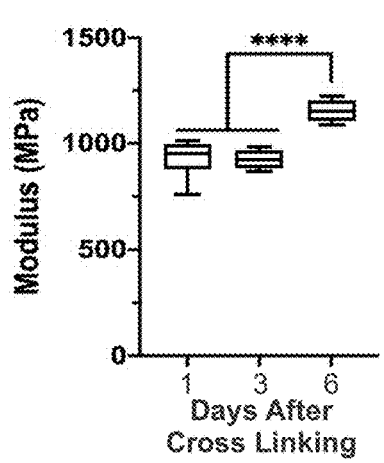
FIG. 54 summarizes the properties and characteristics of an embodiment of the disclosure.

FIG. 46 illustrates system 4600, which uses an array of syringes to form acidified collagen fibers. System 4600 may be considered to be a high-throughput system. In some embodiments of the disclosure, clinical grade collagen is dissolved in acid (acetic acid or a mineral acid such as HCl) in a closed container made of materials inert to the acid and to the collagen. Polypropylene is one such material. The volume of the collagen and acid typically is less than about 50% of the volume of the closed container to encourage thorough mixing. The solution is stirred overnight, or for between about 16 hours and 30 hours, typically between about 15 hours and about 20 hours. The solution then is centrifuged to degas the solution.

The degassed solution then is placed into syringes. The number of syringes used equals the number of fibers to be formed simultaneously. System 4600 in FIG. 46 shows use of outlets from 8 syringes mounted in rotatable plate 4601. The plunger of each syringe is pressed into the barrel of the syringe by a plate (not shown) to ensure that the fibers are extruded in essentially equal quantities. Acidified collagen is pressed through first nozzle 4602 to form first fiber 4612; through second nozzle 4603 to form second fiber 4613; through third nozzle 4604 to form third fiber 4614; through fourth nozzle 4605 to form fourth fiber 4615; through fifth nozzle 4606 to form fifth fiber 4616; and through the remaining nozzles. In some embodiments, not all nozzles are used. In embodiments of the disclosure, rotatable plate 4601 may have more or fewer nozzles mounted through it.

The fibers are gathered at guide 4630 and fed into formation buffer bath 4640. The fibers are kept taught after extrusion. In some embodiments, rotatable plate 4601 may be turned in either direction to produce twisted fiber. In system 4600, rotatable plate 4601 may be rotated by rotation of drive plate 4620, which meshes with rosette notches 4621. Any suitable drive system may be used. In some embodiments, rotatable plate 4601 is not rotated, so the resultant bundle of fibers is not twisted. However, the bundle is maintained under tension by a tensioner on the fiber bundle as the fibers are dehydrated, and until it is wound on a collector. Typically, a grooved cylinder is a suitable collector, particularly for wet fibers.

FIG. 16 illustrates details of the nozzle system 1600. Pump 1502 pumps liquid acidified collagen 1620 into the center needle of biaxial needle 1503. Buffer solution, also called sheathing solution, from 1610 is introduced in the direction of flow arrow 1611 into the outer needle of biaxial needle 1503, thus forming collagen microfibers 1504 as the polymerization process proceeds. The collagen fluid is focused by the sheathing fluid 1611 in extensional flow. The detailed view of the needle illustrates how acidified liquid collagen 1620 moves in the direction of the low speed arrows, and then increases in speed, as indicated by high speed arrows 1630 and higher speed arrows 1640. Similarly, sheathing fluid moved in the direction of speed arrows 1611, arrows 1635, and arrows 1645. Flow of the reactants continues in the direction of arrow 1650, where the shading indicates how buffer (sheathing) fluid 1670, which contains phosphate, interacts with the collagen solution and removes water 1680 from the collagen stream.

Once the microfibers 1507 were collected onto device 1508, they were air-dried for half hour and subsequently crosslinked under different experimental conditions. Chemical reagents used during extrusion and crosslinking are included in Table 1 in FIG. 17.

In situ crosslinking (chemical or enzymatic) for the groups shown in Table 2 in FIG. 18 was performed by dissolving the amount shown in FIG. 18 for each crosslinker in acidified collagen mixture for time stated in FIG. 18. Concentrations and times of crosslinking for some materials were obtained from specific references identified in FIG. 18. FIG. 18 summarizes strength comparisons. Conditions in italics were selected for characterization post optimization of collection methods. Microfibers from in situ crosslinked collagen were then extruded on to a two-bar device and kept taut as shown in FIG. 15. FIG. 18 also shows that the cross-linker can be present in an amount between about 5 mM and about 500 mM, typically between about 10 mM and about 500 mM, and more typically between about 25 mM and about 250 mM.

More typically, however, un-crosslinked microfibers may be collected on solid spool 1110 (see FIG. 11) with closely spaced grooves. Microfibers were collected directly onto these grooves while maintaining tautness. Collection onto spools typically is more efficient than the two-bar device. Spools of un-cross-linked microfibers were cross-linked chemically in 70% aqueous ethanol as used for the 2-bar device. Tube containing the microfiber spool in crosslinker solution was placed on rollers, as shown in FIG. 12, and rotated at 1 rpm to ensure uniform crosslinking of microfibers.

For post-extrusion chemical crosslinking, un-crosslinked or in situ crosslinked and taut collagen microfibers that were extruded on two-bar device 1508 or grooved roller 1110 were air dried for half hour and then submerged into a solution of crosslinker in 70% ethanol solution and placed on a rocker at low speed. The aqueous ethanol medium ensured that microfibers remained dehydrated throughout the crosslinking period. After crosslinking, microfibers were stored in a desiccator until further tests were performed.

In some embodiments, collagen fiber is wet or damp when collected. In such cases, the fibers may tend to stick to each other if they are allowed to touch, especially during collection. Thus, in some embodiments, a two- or multi-bar collector device may be advantageously used because it may allow the fibers to dry before being contacted by another fiber. In some embodiments, a grooved roller is particularly useful for collection of wet fibers because fiber-to-fiber contact is precluded, as only 1 fiber is collected in a groove.

In some embodiments, the fiber may be dried by blowing a gas, typically air, over the fiber after it leaves the dehydration bath and before the fiber is collected. The fiber is suspended between the dehydration bath and a collector, which may be a flat cylinder, a bobbin, or any other suitable collector. The fibers need not be kept apart from each other as they are dry.

In some embodiments, the fiber may be dried by passing air at room temperature over the fiber at room temperature and at a speedbag 0.25 m/sec and about 10 m/sec, typically between about 1 m/sec and about 4 m/sec, and more typically about 2 m/sec. The speed of the drying air should not be so high as to rupture, tear, or break, the fiber. The air is passed over for about the time it takes to dry the fiber, typically equal to the time it takes the fiber to travel about 1 meter. The drying air may be moved by fans in an open system or in a recycling system. In some embodiments, the collection device, such as a bobbin or a flat cylinder. The cylinder rotates at a draw speed between about 1 time and about 9 times the formation speed. In such a circumstance, essentially infinitely long fibers may be made.

The dehydrothermal treatment (DHT) for crosslinking microfibers involved dehydrating relaxed extruded microfibers at 110° C. and under vacuum for 1, 3, and 5 days with or without additional crosslinking in glyoxal, as described above.

For UltraViolet Radiation (UVR) mediated crosslinking, methacrylated collagen was used for extrusion. The extruded microfibers were then exposed to a 365 nm emitting UV light source for 20 minutes. These microfibers were then placed in a desiccator or further crosslinked with 10 mM glyoxal in 70% aqueous ethanol.

Mechanical properties of single microfibers were generated using a "discrete fiber" test method wherein the cross-sectional area of individual microfibers and a known quantity of microfibers on a cartridge are averaged to determine the ultimate tensile strength (UTS), modulus, and strain at failure (%), because a single microfiber was too delicate to consistently handle. While two-bar collection setup 1508 led to microfibers being cylindrical, the microfibers collected on the solid, grooved spool were thin and ribbon-like. The ribbon-like collagen fibers have a width between about 10 µm and about 70 typically between about 15 µm and about 60 and more typically between about 20 µm and about 50 The ribbon-like collagen fibers have a thickness between about 4 µm and 20 µm, typically between about 5 µm and about 18 and most typically between about 6 µm and about 17 µm.

Widths were measured from analyzing images obtained at 10 different points on 3 separate, 1.5-inch long, microfibers using an inverted light microscope, such as Axio Vert.A1 Model, Zeiss, Germany, and ImageJ software (NIH Shareware, Bethesda, Md.). Cross-sectional images of microfiber bundles using a Scanning Electron Microscope (SEM) were used to determine the thickness of the microfiber using Image J software. In order to meet the demands of rigorous mechanical testing that would be relevant with regard to the performance of embodiments of collagen microfibers of the disclosure in vivo, a high-throughput method of wet-tensile-testing our microfiber samples, such as that disclosed in Gentleman et al., 2003, may be used.

A bath and sample holding system was used to provide wet-tensile strength mechanical testing of bundles in a cartridge. This system made it possible to provide a 30-minute soak while processing a sample every 5 minutes during soaking of extruded microfiber embodiments of the disclosure. The soaking fluid may be Gibco's Dulbecco's phosphate-buffered saline (DPBS), available from ThermoFisher Scientific. Typically, a minimum of 4 cartridges were mechanically wet tested at room temperature under uniaxial tensile testing on an MTS Criterion Model 42 (Eden Prairie, Minn.) at a pulling rate of 1 mm/s to obtain stress vs strain curves. Discrete-fiber testing was done to generate results quickly while optimizing processing parameters.

The bath and sample holding system includes a bath filled sufficiently to cover the materials being tested in fluid. The fluid may be Gibco's Dulbecco's phosphate-buffered saline (DPBS). During testing, the sample holder was held in fluid by jaws at opposite ends of the tensile tester. Testing was carried out by moving the jaws away from each other.

The UTS of wet embodiments of the disclosure typically is between about 1 MPa and about 800 MPa, typically between about 75 MPa and about 400 MPa, and more typically between about 90 MPa and about 350 MPa, and even more typically between about 100 MPa and about 325 MPa. The modulus of wet embodiments of the disclosure is between about 10 MPa and about 7,500 MPa, typically between about 100 MPa and about 6,000 MPa, and more typically between about 1,000 and 4,000 MPa.

The UTS of dry embodiments of the disclosure typically is between about 25 MPa and about 1,900 MPa, typically between about 100 MPa and about 1,800 MPa, and more typically between about 5000 MPa and about 1,700 MPa, and even more typically between about 1,200 MPa and about 1,700 MPa. The modulus of dry embodiments of the disclosure is between about 14,000 MPa and about 20,000 MPa, typically between about 15,000 MPa and about 19,000 MPa, and more typically between about 15,500 and 18,500 MPa.

Testing to compare certain embodiments of wet and dry fibers showed comparative ranges of Ultimate Tensile Strength of about 1 to about 755 MPa for wet fibers vs. about 25 to about 1650 MPa for dry fibers; a Modulus of Elasticity of about 10 to 7,200 MPa for wet fibers vs. about 15,950 to about 18,600 MPa for dry fibers; a Strain at Break of about 2 to about 41% for dry fibers vs. about 9 to about 14% for dry fibers; and an Average Fiber Diameter of about 14 to about 82 μm for wet fibers vs. about 10 to about 70 μm for dry fibers.

SEM imaging was used to obtain cross-sectional as well as longitudinal microstructural signatures of un-cross-linked and cross-linked extruded microfibers. SEM imaging was performed using a Zeiss Evo 10 microscope (Zeiss) with a 10 kV beam intensity. For cross-sections, microfiber bundles were soaked in DPBS for 30 minutes, dried for an hour on SEM stubs, sputter coated, and imaged.

For TEM, dry microfibers from Telo GLY group (telocollagen cross-linked with glyoxal) were re-hydrated using distilled water. These were then fixed in 2% glutaraldehyde (Electron Microscopy Sciences, PA) and 4% paraformaldehyde (Alfa Aesar, MA) at room temperature for 30 minutes. Subsequently, 2 washes (10 minutes for each wash) using cacodylate buffer (Electron Microscopy Sciences) was done. This was followed by a 30-minute incubation in 1% Osmium Tetroxide (Electron Microscopy Sciences), one wash in cacodylate buffer and 2 washes in distilled water (10 minutes each). Dehydration through a series of ascending ethanol concentrations (once in 30%, 50%, 70% and 95% for 10 minutes and twice in 100% for 10 minutes each wash) was performed; microfibers were then immersed twice in 1:1 mixture of ethanol and propylene oxide (Electron Microscopy Sciences) mixture for 10 minutes, followed by 100% propylene oxide treatment for 10 minutes. These samples were left overnight in 1:1 EPON 812:propylene oxide (Electron Microscopy Sciences). EPON 812 is a glycerol-based aliphatic epoxy resin. Next day, the samples were immersed in 4:1 EPON 812:propylene oxide for 4 hours and transferred to 100% EPON 812 for overnight incubation. Next day, samples were transferred to fresh EPON 812 resin, embedded into bullet capsules (Electron Microscopy Sciences) and polymerized at 60° C. for 12 hours. The molds were thinly sectioned and imaged using TEM (Model No. Jeol 1230, Jeol USA, MA). Alternative methods for determining these values may be used.

Ninhydrin assay may be used to evaluate the amount of free amino groups in cross-linked microfibers. For this, un-cross-linked as well as crosslinked microfibers were cut into lengths ranging from 14-16 cm each. At the same time, various known concentrations of a standard amino acid, glycine (Sigma-Aldrich), were prepared in 0.05% acetic acid according to manufacturer's protocol. The microfiber samples and glycine solutions were heated in ninhydrin solution (Sigma-Aldrich) for 20 minutes followed by cooling to room temperature for at least 1.5 hours. Then, 95% ethanol was added to each of the samples and glycine standards. Optical absorbance of these samples was recorded with an ultraviolet-visible spectrophotometer (SpectraMax i3, Molecular Devices, ODU, Norfolk, Va.) at 570 nm. Other methods of testing may be used.

Absorbance of various known glycine concentrations was used to obtain a standard curve. The amount of free amino groups in un-crosslinked samples ($M_{UX}$) and crosslinked ($M_X$) microfibers is proportional to the optical absorbance of the solution and was obtained from the standard curve of glycine that was generated. In order to calculate Degree of crosslinking, Equation 1 was used, as follows:

$$\text{Crosslinking Degree}(\%) = \left(\frac{M_{UX} - M_X}{M_{UX}}\right) \times 100 \qquad \text{Equation 1}$$

Differential Scanning calorimetry (DSC) and Fourier-Transform Infrared (FTIR) Spectroscopy were used to determine whether amide bonds characteristic of type I collagen were present. Testing of microfibers was performed using a Differential Scanning calorimeter (DSC2500, TA Instruments, DE) and FTIR spectroscopy was performed on Platinum ATR (Brucker, Billerica, Mass.). FTIR spectra was used to confirm the presence of three major peaks of amide bonds characteristic of type I collagen at 1235 cm$^{-1}$, 1560 cm$^{-1}$, and 1650 cm$^{-1}$ wavelengths. Un-cross-linked and cross-linked microfibers were compared to the starting material by assessing shifts in peaks with the Essential FTIR bioinformatics software (Operant, Madison, Wis.).

Extruded microfluidic fibers as single fibers, bundles of 150 microfibers (held together by coated Vicryl 4-0 (Ethicon, NJ) suture and cut to a final size of 10 mm), or on cartridges used for mechanical testing as described above were sealed inside Tyvek pouches with a STERRAD chemical indicator (4MD Medical Solutions, Lakewood, N.J.) and sent for E-beam sterilization (Steri-Tek, Fremont, Calif.) using a 20 KGy+/−2 KGy target dose.

Sterilized glyoxal and DL-Glyceraldehyde crosslinked microfibers were hydrated in tenocyte growth media for 30 minutes and placed in 24 well plates that were pre-coated with Poly(2-hydroxyethyl methacrylate) (pHEMA) (Sigma Aldrich). Twenty-five thousand human tenocytes (ZenBio, NC) (in 100 μl tenocyte growth media) were seeded on sterilized microfibers in triplicates. After seeding, cells were allowed to attach for 1 hour before an additional 500 μl of tenocyte growth media was added. After 12 days, tenocyte attached microfibers were stained with live cellular stain, CellTracker™ Green CMFDA (5-chloromethylfluorescein diacetate) (Thermo Fisher Scientific) following manufacturer's protocol. Samples were then fixed using 4% paraformaldehyde and subsequently stained with a nuclear stain, DAPI (Thermo Fisher Scientific) to visualize attached tenocytes on microfibers using a confocal microscope (Zeiss Axio Observer Z1, Zeiss).

Cytotoxicity (or cell viability) of embodiments of extruded microfibers on human tenocytes was assessed using the CyQuant Lactate Dehydrogenase (LDH) cytotoxicity assay kit (Invitrogen) and MTT assay kit (Sigma Aldrich) following manufacturer's protocol. Briefly, after determining the optimum seeding density for the assay, $7 \times 10^3$ tenocytes were plated on each well of 48 well plates and allowed to grow for 24 hours in tenocyte growth media in a humidified incubator maintained at 37° C. and 5% CO2. Sterilized microfiber bundles were rinsed for 10 minutes in cell culture media and placed on tenocytes in each well. Tenocytes grown on plastic (cells only) were used as positive (for cell survival orviability). Zinc dibutyldithiocarbamate (ZDBC) film and 10 mM glyoxal chemical were used as negative (for cell survival or viability) controls. The effects of Ethicon Vicryl suture were also assessed in this experiment as it was used to hold extruded microfiber bundles together. Wells seeded with tenocytes but containing no samples were set up to evaluate the maximum and spontaneous LDH release as described in the manufacturer's protocol. Samples were incubated for 7 days before evaluating the release of LDH in the media. The % cytotoxicity using LDH assay was calculated following manufacturer's protocol. The % Cell Survival was then calculated as 100% Cytotoxicity. In embodiments of the disclosure, % cell survivability is at least about 94%, typically at least about 95%, more typically at least about 96%, and most typically at least about 97%. It is also possible to achieve 98% or 99% cell survivability. The % Cell viability using MTT assay was calculated following manufacturer's protocol. In embodiments of the disclosure, the % Cell viability is at least about 70%, typically at least about 80%, more typically at least about 85%, and most typically at least about 90%. Other suitable test methods are available The health and viability of live tenocytes growing with extruded microfiber embodiments of the disclosure was also assessed using the AlamarBlue™ assay (BioRad, Hercules, Calif.) as per manufacturer's protocol.

Embodiments of cross-linked microfiber bundles were subcutaneously implanted into rats. All surgical procedures were conducted according to a protocol approved by Institutional Animal Care and Use Committee (IACUC), Old Dominion University, Norfolk, Va. Per ISO 10993-6, n=3 crosslinked collagen microfiber bundles (prepared and sterilized as described above) or collagen coated FiberWire® (suture control) were implanted subcutaneously in female Sprague Dawley rats. Rats were anesthetized with isoflurane inhalation. Flanks were shaved, and Nair depilatory cream was applied to remove hair from surgical site. Incisions were made dorsally in the flank area and a hemostat was used to create a pocket for implants. Once scaffolds were placed in the pocket, the incision was closed using suture. After 4 weeks, the rats were humanely euthanized for tissue collection.

Harvested microfiber explants at 4 weeks were fixed in 4% paraformaldehyde (Alfa Aesar) for 24 hours then transferred to DPBS (Thermo Fisher Scientific). The samples were sectioned to obtain 5 µm thickness and serial sections were stained with hematoxylin & eosin (H&E) as well as Masson's Trichrome at IDEXX (West Sacramento). Polarized light microscopy was used to image collagen organization in the tissues surrounding the implants.

Immunolabeling was also performed on serial sections to detect the presence of CCR7 (M1) and CD163 (M2) macrophage phenotypes in native tissues surrounding our implants using standard protocols provided by antibody manufacturers. Briefly, after deparaffinization, antigen retrieval (20 minutes boiling in 10 mM Citrate Buffer pH 6), permeabilization and blocking with 2.5% horse serum, slides were stained for either CD163 (M2 macrophage phenotype), or CCR7 (M1 macrophage phenotype). The M2 macrophage marker, mouse anti-rat CD163 (#MCA342GA, BioRad, CA), was diluted to 1:30 for an overnight incubation in humidified chamber. Post incubation, slides were washed in PBS and incubated with a goat anti-mouse secondary antibody (#A-11005, Thermo Fisher Scientific) at a 1:50 dilution for 1-hour in the dark at room temperature. CCR7, a M1 macrophage marker, was diluted at 1:50 in PBS for an overnight incubation (#MA5-31992, Thermo Fisher Scientific). Next day, after PBS wash steps (3 times), a goat anti-rabbit fluorescent antibody (#A32740, Thermo Fisher Scientific) was applied to the slides at a concentration of 1:200 for 1-hour in the dark at room temperature. For primary controls, serum-blocked slides were either stained with IgG Mouse (1:30) (Thermo Fisher Scientific) and goat anti-mouse secondary antibody (1:50) or IgG Rabbit (1:200) (Thermo Fisher Scientific) and goat anti-rabbit secondary antibody (1:200). For secondary controls, serum-blocked slides were stained with only the secondary fluorescent antibodies. All antibodies were diluted in blocking serum. All slides were stained for the nucleus with DAPI for 5 minutes, washed in PBS and mounted using VectaMount (Vector Labs, CA) for visualization and analysis.

The immunolabeled slides were examined and imaged using an inverted light microscope (Axio Vert.A1 Model, Zeiss). Fluorescence images were acquired for the test and control slides (data not shown) under same exposure conditions. The images for the test samples were evaluated. Quantitative analysis was performed to obtain the number of cells expressing M1 only, M2 only, M1 and M2, and/or no M1/M2 phenotype. Here 4-5 areas per image (3 images were analyzed per test sample) of approximately 20-30 µm at the interface of the implants and native tissue (2-3 cell layers) were analyzed using a high-power microscope field (40× magnification). The total number of cells was determined by counting DAPI stained nuclei. The number of cells labeled positively for each marker(s) was also counted. The proportion of cells that were labeled with the specific marker(s) was determined as a percentage of total number of cells in that region.

Embodiments of the disclosure also were subjected to long term stability testing. Telo GLY microfibers were de-spooled under tension onto cartridges. Six sterilized cartridges were hydrated and mechanically tested as described above to obtain mechanical properties of the microfibers prior to incubating the remainder of the sterilized cartridges in a petri dish containing Eagle's Minimum Essential Medium (EMEM) (ATCC, VA) supplemented with 1% Gibco® Antibiotic-Antimycotic (ABAM) (Thermo Fisher Scientific) to suppress bacterial and fungal contamination in an incubator maintained at 37° C. and 5% CO2. Throughout the duration of the experiment, it was ensured that the cartridges were always submerged in sterile contamination-free media and hence remain hydrated. Six soaked cartridges were removed at 1 week, 1 month, 3 months, and 6 months to perform MTS testing. Simultaneously, microfiber diameters were measured (as described above) to determine the extent of swelling of the microfibers overtime.

An unpaired two tail t-test was used to assess any significant differences in a property or characteristic between any two groups. A two-way ANOVA followed by the post-hoc Tukey's Multiple Comparison Test also were used to assess differences in UTS for different crosslinker groups in Table 1 in FIG. 17. Ordinary one-way ANOVA followed by Dunnett's multiple comparisons test also was performed to assess differences in health and viability, as described in additional detail below. A priori, p values <0.05 were defined as significant. All tests were performed using GraphPad Prism 7, and all parameters are expressed as Mean±Standard Error of the Mean (S.E.M.).

Additional Examples

Examples were obtained by carrying out embodiments of the disclosed products and methods. A robust microfluidic extrusion setup of FIG. 15 and FIG. 16 was designed and used to consistently generate collagen microfibers for subsequent testing. This approach yielded continuous microfiber production without defects for crosslinking.

To strengthen and stabilize the collagen microfibers, a wide range of conventional, novel, and combination crosslinking conditions were screened. Table 2 in FIG. 18 shows a summary of crosslinkers and mean UTS of 50 types of crosslinked microfibers as compared to the un-crosslinked microfibers using the testing method described above. This data showed different crosslinkers/crosslinking protocols (crosslinking in situ or post extrusion, range of crosslinker concentrations and time of crosslinking) affected the UTS of the microfibers to varying degrees. The crosslinking condition that had significantly high mean UTS amongst all the conditions tested with that crosslinker has been starred ($p < 0.01$) in Table 2 in FIG. 18.

As shown in FIG. 18, crosslinking procedures with chemicals post extrusion, such as glyoxal (10 mM and 72 hours post extrusion, 121.2±7 MPa) and DL-Glyceraldehyde (25 mM and 72 hours post extrusion, 128±12 MPa), resulted in microfibers with UTS nearly 20-fold higher than the un-crosslinked microfiber (6.1±1 MPa). Notably, crosslinking using EDC and EDC/NHS on microfluidic microfibers using this extrusion setup yielded UTS values (16.6±2 MPa and 30.2±1 MPa respectively), which is significantly lower than the glyoxal and DL-Glyceraldehyde groups described above. In situ crosslinking using chemical crosslinkers such as choline bitartrate (1 mM or 100 mM), EGCG (200 μM and 1 mM) and D-sorbitol (200 mM) resulted in a significant decrease ($p < 0.01$) in UTS compared to un-crosslinked microfiber. Physical crosslinking techniques such as DHT (3 days, 16.2±1 MPa) post extrusion also yielded microfibers stronger than the un-crosslinked microfiber, but was weaker than the chemical crosslinking groups using glyoxal and DL-Glyceraldehyde described above. UVR treatment (1.9±0.2 MPa) of methacrylated collagen microfibers post extrusion also yielded fibers significantly weaker than un-crosslinked collagen microfibers ($p < 0.01$).

Since crosslinking of extruded microfibers using glyoxal were amongst the highest in UTS, further crosslinking of some of the in situ (L-Lysine or D-Sorbitol) or otherwise crosslinked fibers (DHT and UVR) was carried out with 10 mM glyoxal for various time points. Additional crosslinking with glyoxal increased the UTS of all these groups with most significant increase ($p < 0.01$) observed for L-Lysine (10 mM, 2 hours)/Glyoxal (10 mM, 24 hours) (96.9±5 MPa) and UVR (0.3 hours)/Glyoxal (10 mM, 24 hours) (86.6±10 MPa) groups.

Figure 19:
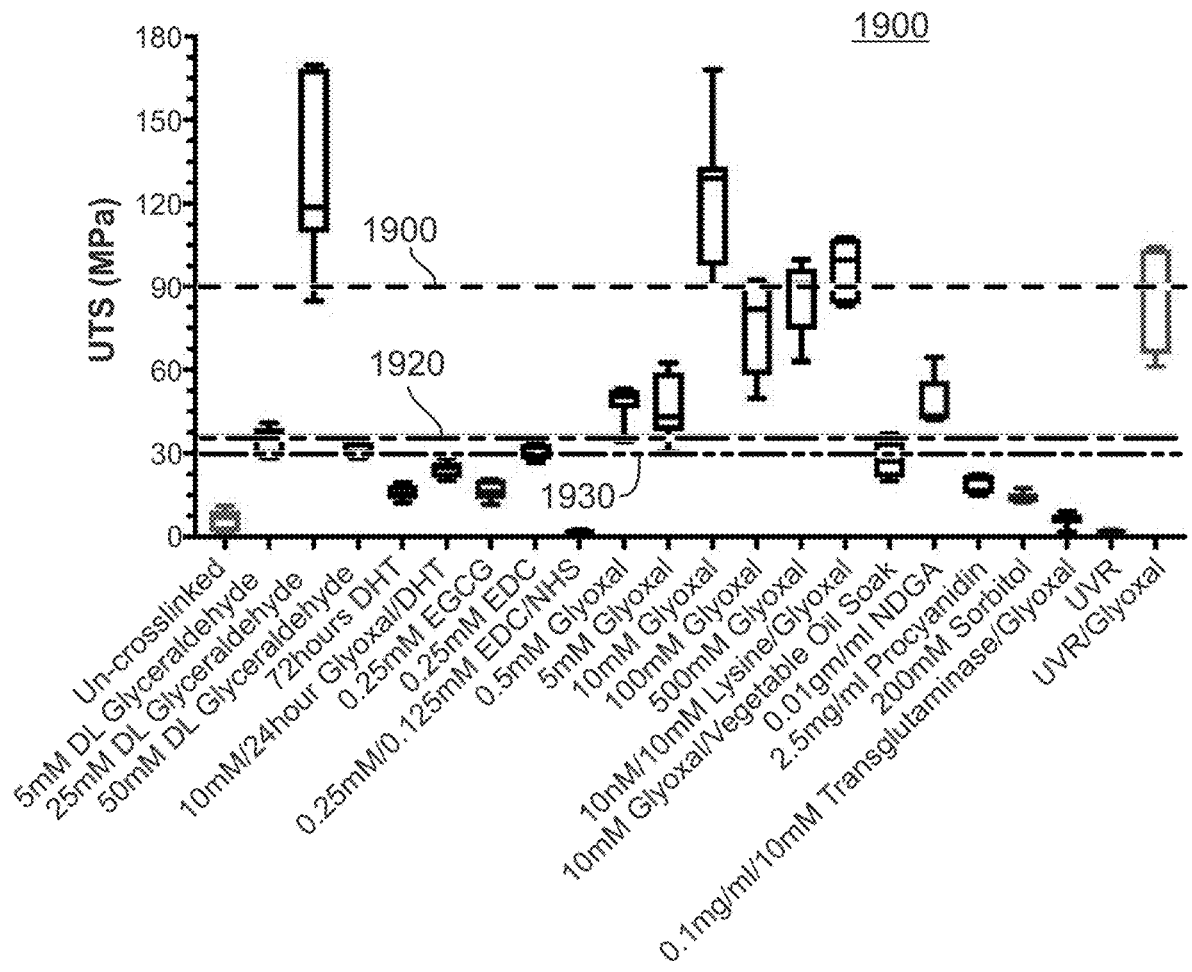
FIG. 19 is a graph summarizing a mechanical property relevant to the disclosure.
Figure 20:
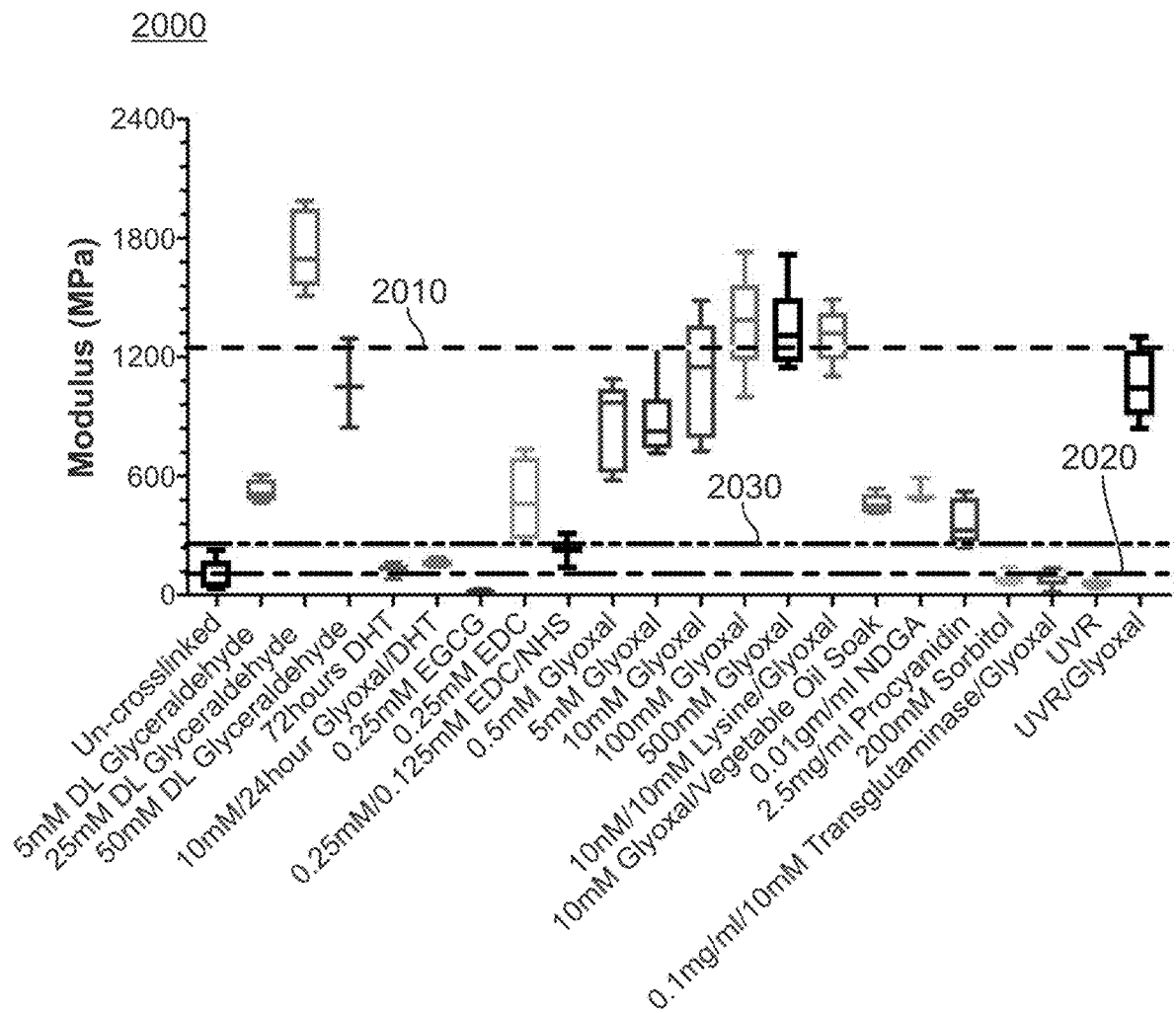
FIG. 20 is a graph summarizing another mechanical property relevant to the disclosure.
Figure 21:
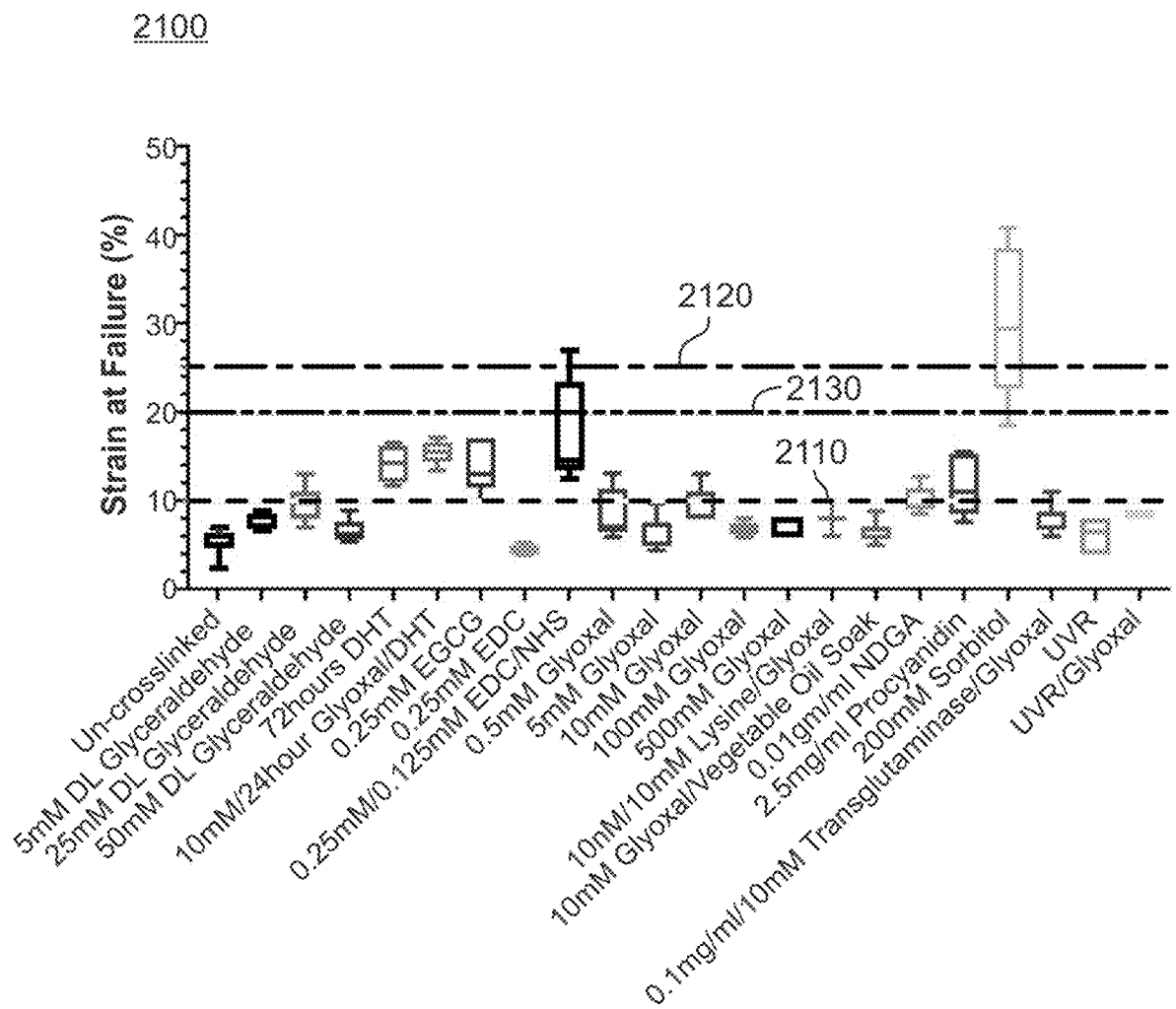
FIG. 21 is a graph summarizing still another mechanical property relevant to the disclosure.
Figure 23:
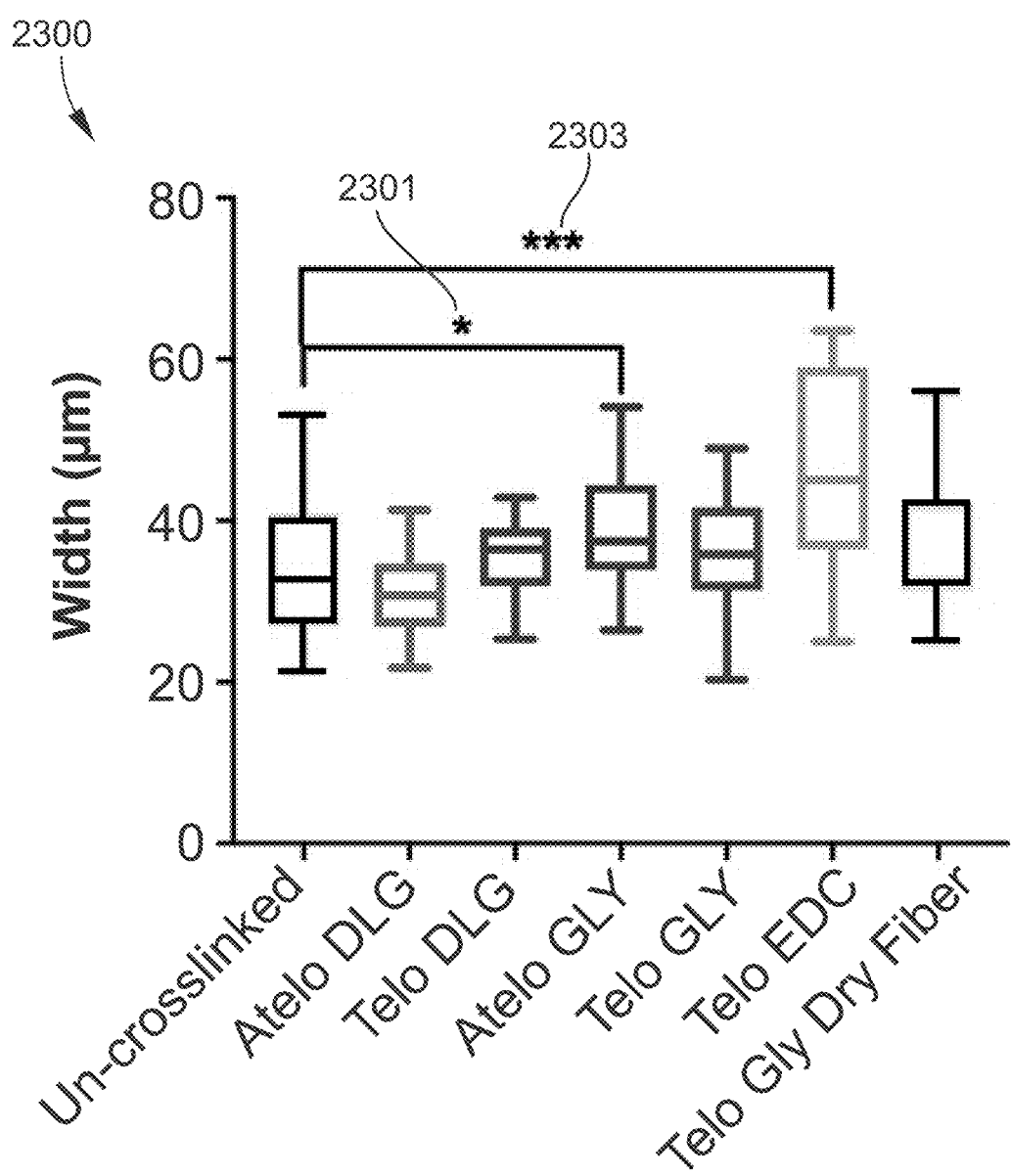
FIG. 23 is a graph summarizing the width of embodiments of the disclosure.
Figure 24:
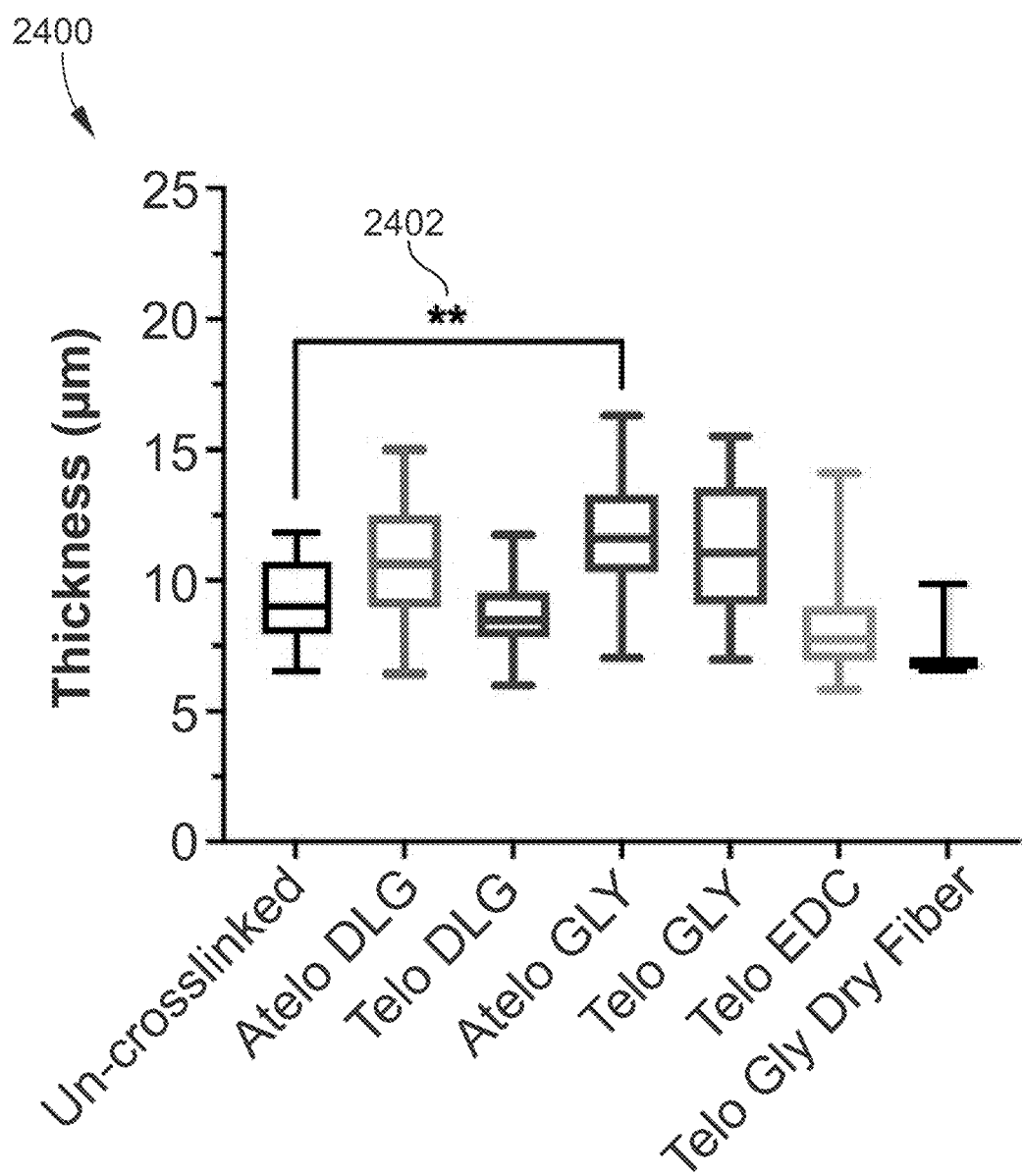
FIG. 24 is a graph summarizing the thickness of embodiments of the disclosure.
Figure 25:
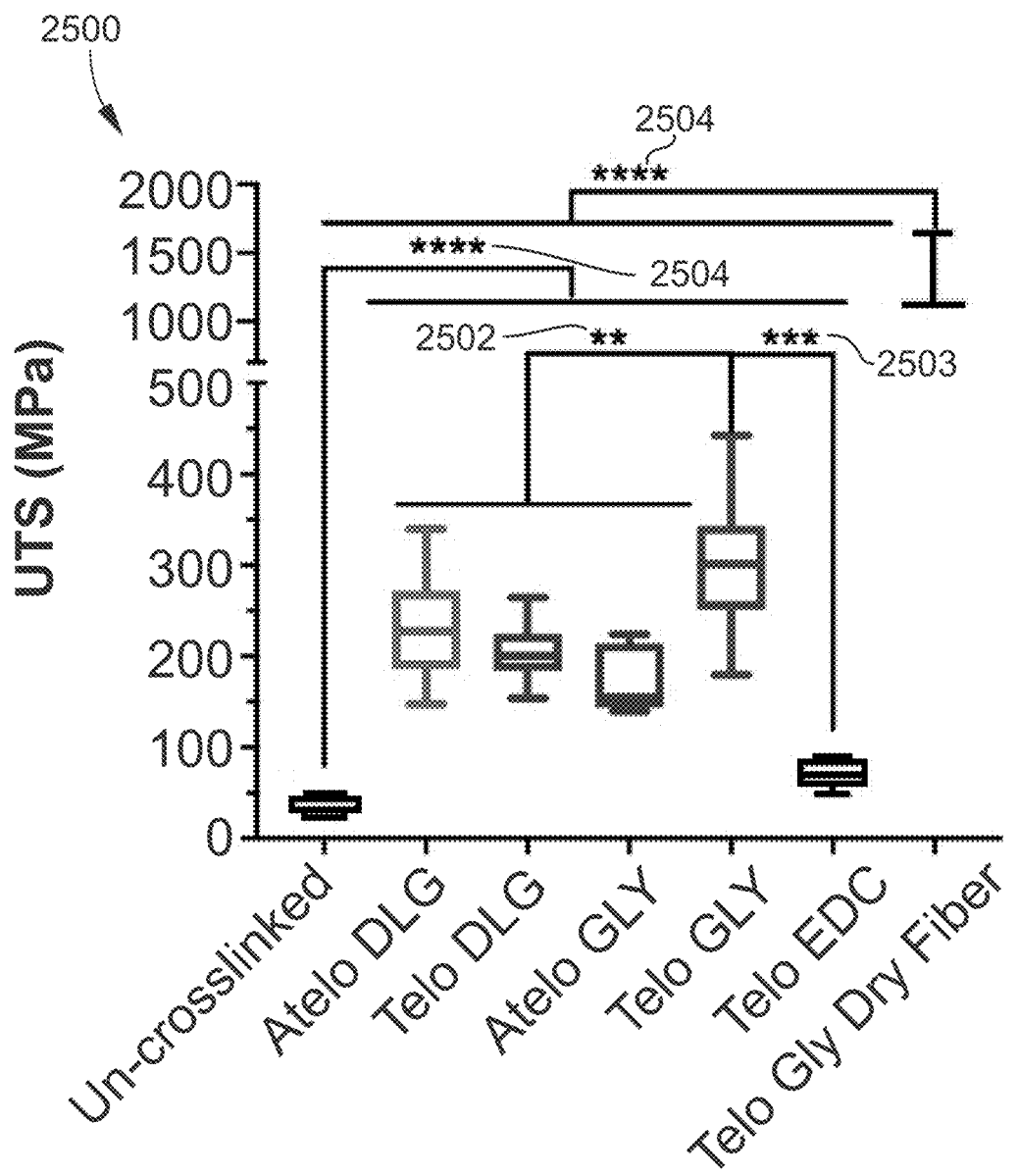
FIG. 25 is a graph summarizing a mechanical property of embodiments of the disclosure.
Figure 26:
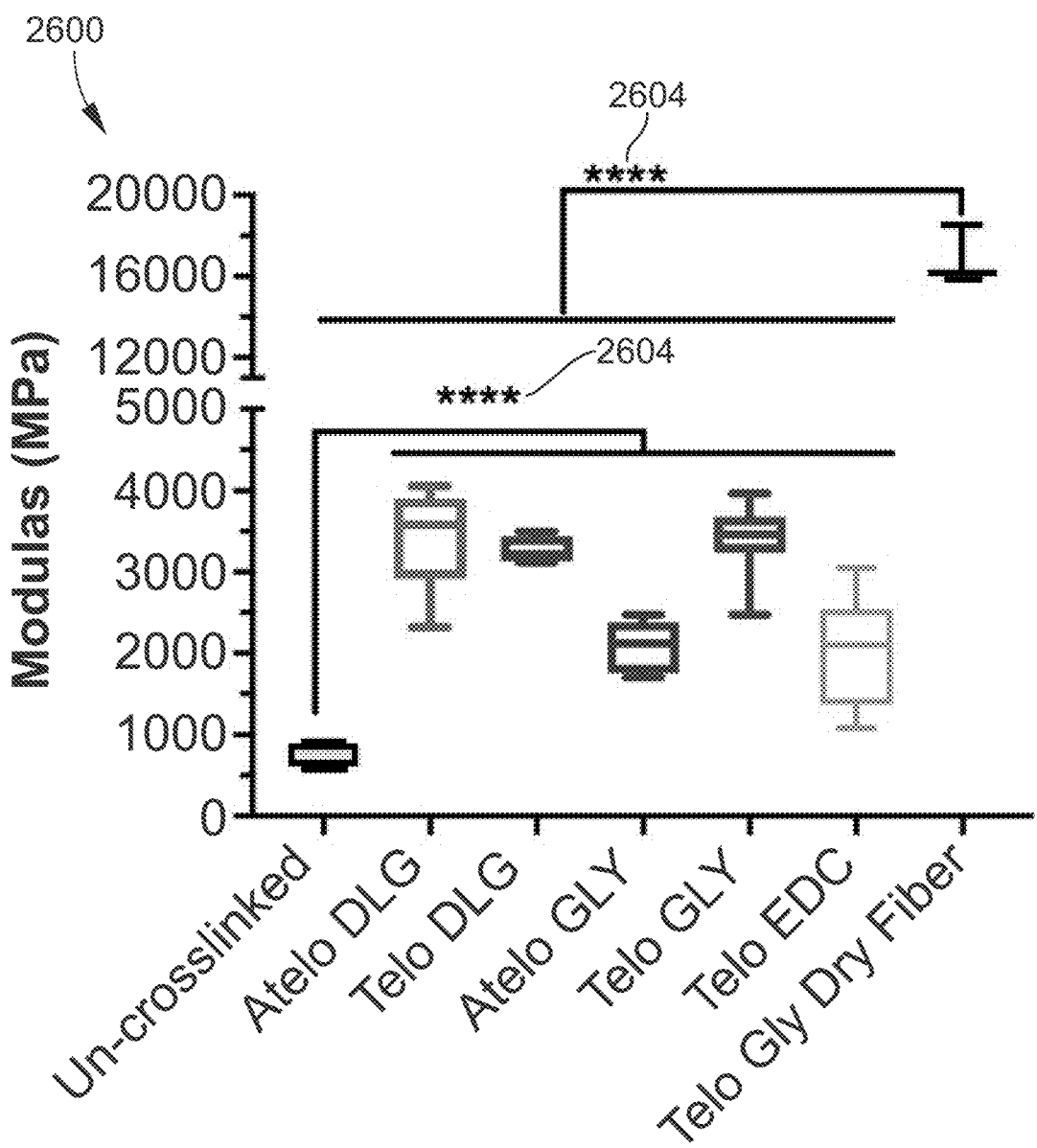
FIG. 26 is a graph summarizing another mechanical property of embodiments of the disclosure.
Figure 27:
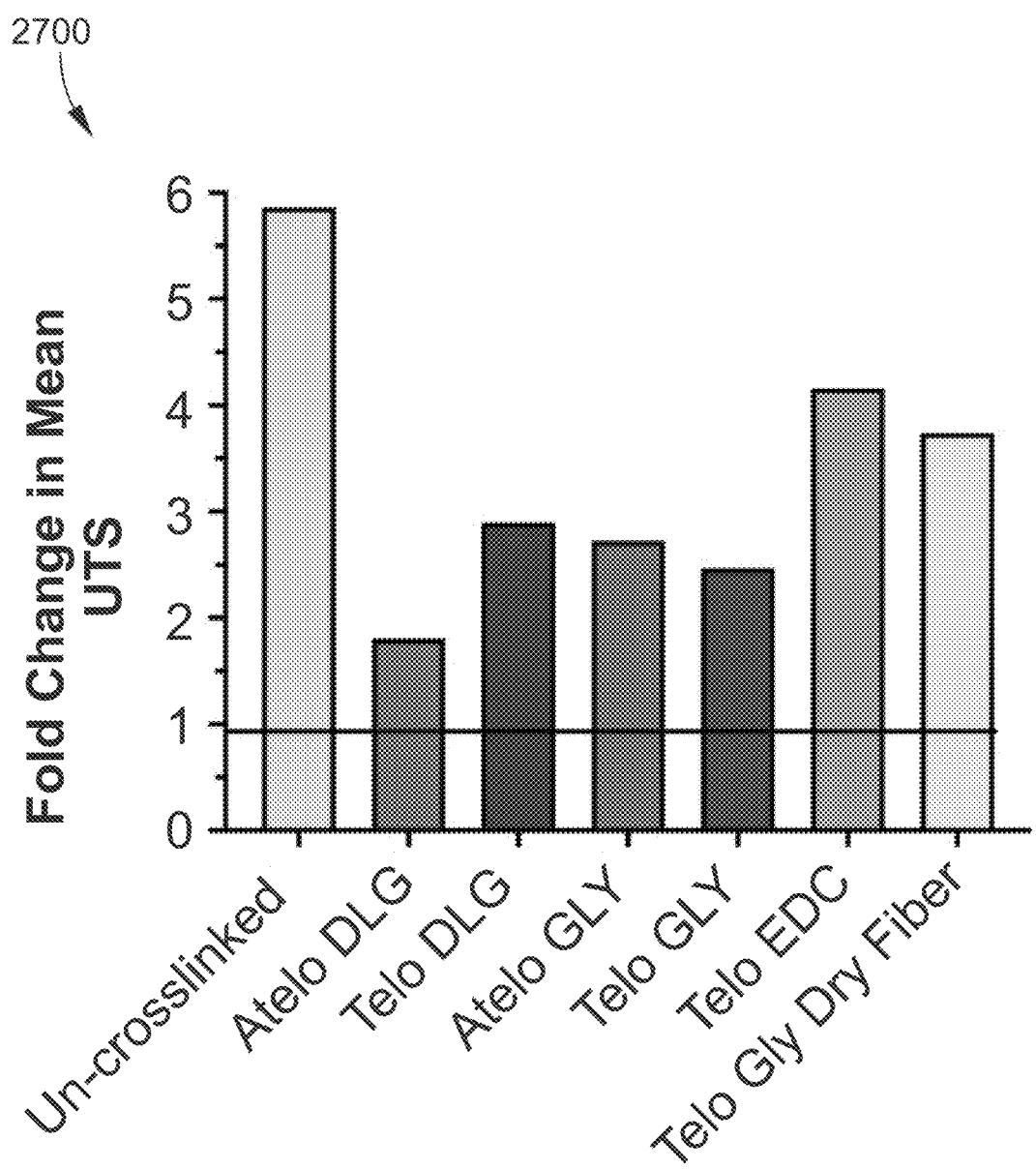
FIG. 27 is a graph summarizing a relationship of a mechanical property of embodiments of the disclosure.
Figure 28:
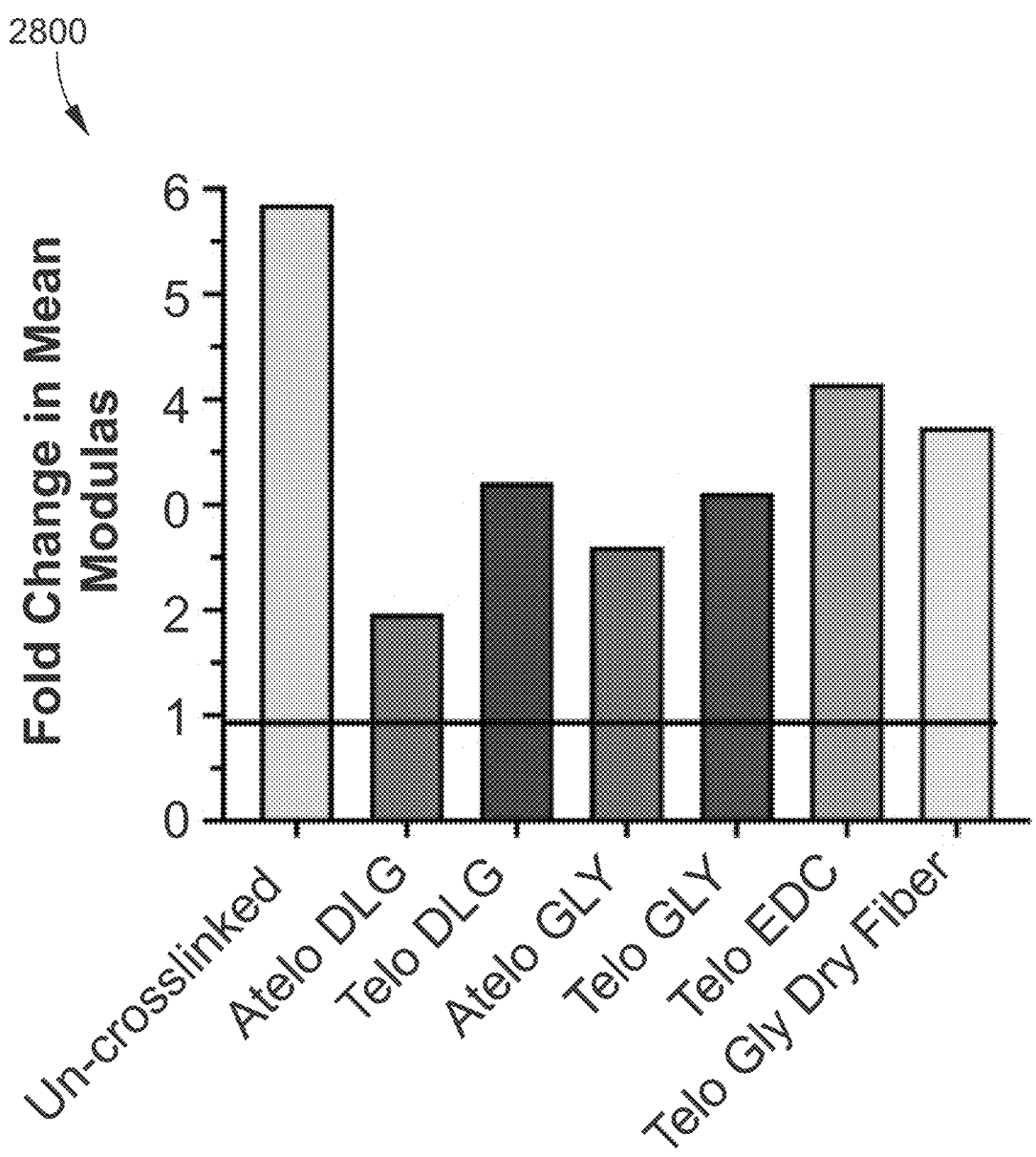
FIG. 28 is a graph summarizing a relationship of another mechanical property of embodiments of the disclosure.

Turning now to FIG. 19, FIG. 20, and FIG. 21, the mechanical properties of representative microfibers from crosslinker groups tested in Table 2 in FIG. 18 were compared to values reported for human ACL (Noyes and Grood, 1976; Peters et al., 2018), Achilles tendon (Wren et al., 2001) and dermis (Gallagher et al., 2012). FIG. 19 sets forth the UTS, MPA, in graph 1900. Graph 2000 in FIG. 20 summarizes Modulus I MPa, and graph 2100 in FIG. 21 is directed to Strain at Failure, %. The ACL values are shown as line 1930, line 2030, and line 2130. The AT values are shown as line 1910, line 2010, and line 2110, and the dermis values are shown as line 1920, 2020, and 2120. Each result relates to a single microfiber. Results illustrated in FIG. 19 revealed that mean UTS of collagen microfibers for some of the crosslinking groups, notably, 10 mM glyoxal with or without 10 mM L-Lysine in situ and 25 mM DL-Glyceraldehyde are equal to or greater than reported UTS of human ACL, AT, and dermis.

These charts reveal that the mechanical properties of the microfibers extruded as described above can be tuned to match and/or exceed those for human Anterior Cruciate Ligament (ACL), human Achilles Tendon (AT), and human dermis by changing crosslinking scenarios. The data is obtained from least 4 identical replicates and error bars indicate S.E.M.

Examples 3 Through 6

Comparative Examples 1, 2, and 3

Four crosslinking conditions shown in italics from the initial screen shown in Table 2 in FIG. 18 and FIG. 19, FIG. 20, and FIG. 21, factoring salient considerations such as mechanical performance, processing time, and/or cost, for further evaluation. The following fibers are exemplified herein:

Example 3 is telocollagen cross-linked with 10 mM glyoxal for 72 hours (Telo GLY). Example 4 telocollagen cross-linked with 25 mM DL-Glyceraldehyde for 24 hours (Telo DLG). Example 5 is atelocollagen cross-linked with 10 mM glyoxal for 24 hours (Atelo GLY). Example 6 is atelocollagen cross-linked with 25 mM DL-Glyceraldehyde for 72 hours (Atelo DLG). Comparative Example 1 is telocollagen cross-linked with 0.25 mM EDC for 24 hours (Telo EDC). These groups were compared to un-crosslinked microfibers (Comparative Example 2) and dry Telo GLY fibers (Comparative Example 3). Telo EDC group (Comparative Example 1) was used for comparison as it is a commonly used benign crosslinker in the field (Cornwell et al., 2007; Enea et al., 2011; Ahmad et al., 2015). Additionally, a high draw collection (high collection speed compared with raw material feed) onto a grooved solid spool 1110, as compared with two-bar device 1508, was used to generate thin, ribbon-like microfibers shown in FIG. 22 to further optimize material properties.

FIG. 22 shows images of Example 3 Telo GLY microfiber (s) depicting ultrastructural features. Frame A is a light microscopy image of a single dry extruded crosslinked microfiber. Frame B and frame C are SEM images of a dry single microfiber at different magnifications. Frame D shows a cross-section of bundled microfibers soaked for 30 minutes in PBS. Frame D reveals structural details and evidence that extrusion using an embodiment of a novel microfluidic setup disclosed herein and shown in FIG. 15 and FIG. 16, followed by the crosslinking strategy, manufactured consistent, uniform, and thin ribbon-like microfibers, as shown by arrows 2206. Arrow 2201 and arrow 2202 in frame B indicate crevice and ridges along the longitudinal axis of dry microfiber. Arrow 2204 and arrow 2205 in frame C show the fibrous sub-fiber structure of wet microfiber. Frame E, frame F, and frame G represent longitudinal TEM images of extruded microfibers.

Optimization of crosslinking chemistry and changes in collection methods led to significant differences in mechanical properties, as summarized in FIG. 23, FIG. 24, FIG. 25, FIG. 26, FIG. 27, and FIG. 28. Tensile testing was carried out in the bath and sample holding system described above. Width and thickness of DPBS soaked ribbon-like collagen microfibers FIG. 23 and FIG. 24 measured from representative images such as those shown for Example 3 in FIG. 22, frame A, frame B, and frame C, were used calculate the improved UTS, graph 2500 in FIG. 25, and modulus on graph 2600 in FIG. 26. Example 3, Example 4, Example 5, and Example 6 were similarly tested, as were Comparative Example 1, Comparative Example 2, and Comparative Example 3.

When compared to the wet un-crosslinked (34.1±2 µm) ribbon-like collagen microfibers, wet Atelo GLY (39.2±1 µm) and Telo EDC (46.4±2 µm) ribbon-like collagen microfibers showed a significantly higher width (p<0.05), as indicated by indicator 2402. Wet Atelo GLY ribbon-like collagen microfibers were also significantly thicker (11.9±0.5 µm) than the un-crosslinked ribbon-like collagen microfibers (9.2±0.5 µm) (p<0.01), as indicated by indicator 2301 in FIG. 23 and indicator 2303 in FIG. 23. Thickness of Telo GLY (11.1±0.5 µm), Telo DLG (8.6±0.2 µm) and Atelo DLG (10.9±0.4 µm), and widths of Telo GLY (36.1±0.7 µm), Telo DLG (35.4±0.8 µm) and Atelo DLG (31.1±1 µm) ribbon-like collagen microfibers upon soaking in DPBS, were similar to that for the un-cross-linked ribbon-like collagen fiber. The most significant change in UTS shown in graph 2500 of FIG. 25 was observed for un-crosslinked ribbon-like collagen fibers; mean UTS, identified as indicator 2504, and modulus, identified in graph 2600 of FIG. 26 as indicator 2604, increased from 6.1±1 MPa and 119.8±23 MPa to 35.8±3 MPa and 701±53 MPa. Ribbon-like collagen microfibers from groups such as Telo GLY (121±7 MPa UTS and 1103±63 MPa modulus to 299±15 MPa and 3431±86 MPa respectively) and Atelo DLG (128 MPa UTS and 1734±79 MPa modulus to 231±18 MPa and 3408±185 MPa respectively) demonstrated at least a 2-fold increase in mean UTS, as shown in graph 2700 in FIG. 27, and modulus, as shown in graph 2800 in FIG. 28. There was no change in strain at failure (%) for all groups tested.

There was a significant increase in tensile properties of all the extruded ribbon-like collagen microfibers from a grooved solid spool. Un-cross-linked ribbon-like collagen microfiber group demonstrated the highest fold change in mean UTS, and modulus compared to other crosslinker groups. Graph 2700 in FIG. 27 demonstrates the significant fold change of UTS in comparison to the data reported in FIG. 19, FIG. 20, and FIG. 21, and graph 2800 in FIG. 28 demonstrates the significant fold change in modulus in comparison to the data reported in Figure FIG. 19, FIG. 20, and FIG. 21 for each of Example 3 through Example 6 and Comparative Example 1 through Comparative Example 3.

An unpaired two tail t-test was used to assess any significant differences between any two groups in FIG. 23, FIG. 24, FIG. 25, FIG. 26, FIG. 27, FIG. 28, FIG. 29, FIG. 30, FIG. 31, FIG. 32, FIG. 33, FIG. 37, FIG. 38, and FIG. 39. Two-way ANOVA followed by the post-hoc Tukey's Multiple Comparison Test and unpaired two tail t-test were used to assess differences in UTS for different cross-linker groups in Table 1 in FIG. 17. Ordinary one-way ANOVA followed by Dunnett's multiple comparisons test was performed to assess differences in FIG. 31, FIG. 32, and FIG. 33, described in additional detail below. A priori, p values <0.05 were defined as significant. All tests were performed using GraphPad Prism 7, and all parameters are expressed as Mean±Standard Error of the Mean (S.E.M.).

Results shown as Mean±S.E.M. and is representative of 3 replicates from 2 or more separate experiments. For indicator 2301, p<0.05. For indicator 2402 and indicator 2502, p<0.01. For indicator 2303, p<0.005. For indicator 2504 and indicator 2604, p<0.0001.

For embodiments of the disclosure, microfiber ultrastructure was determined using light microscope, SEM, and TEM imaging. Other types of imaging may be used. In Example 3, glyoxal cross-linked telocollagen microfibers were characterized. Light microscopy imaging, shown in frame A of FIG. 22, and SEM imaging in frame B of FIG. 22, confirmed homogenous width of dry microfiber along the longitudinal axis. FIG. 22, frame B, and high magnification SEM (frame C of FIG. 22) imaging of longitudinal section revealed parallel alignment of ridges and crevices within the dry microfiber, as shown by FIG. 22, frame D. Frame D of FIG. 22 highlights cross-sectional features of DPBS soaked extruded crosslinked microfiber bundle using SEM. These images reveal ultrastructural features of an external smooth surface with apparent fibrous sub-fiber structure, as shown at arrows 2206. This demonstrates that extruded crosslinked microfibers are consistent, thin, and ribbon-like. Further evidence that collagen alignment from the molecular-through nano-scale in native connective tissue is recapitulated in our crosslinked microfibers is revealed from TEM imaging, frame E, frame F, and frame G of FIG. 22.

To biochemically assess the degree of crosslinking, biochemical, and biophysical characterization of embodiments of crosslinked microfibers, a ninhydrin assay was used. The results are set forth in graph 2901 in FIG. 29. Example 3, Telo GLY (86±1%) and Example 6, Atelo DLG (82±3%) microfibers demonstrated significantly higher degree of crosslinking compared to Example 5, Atelo GLY (68±4%) and Example 4, Telo DLG (59±6%), highlighting that higher time of crosslinking improved crosslinking efficiency.

Primary and secondary protein structure of the extruded collagen microfibers also was assessed. SDS-PAGE analysis of the acidified starting material confirmed the presence of primary alpha, beta and gamma chains of collagen. However, due to the inability of the microfibers to be dissolved in acid, it was not possible to detect any collagen in the microfiber acid extracts.

Figure 29:
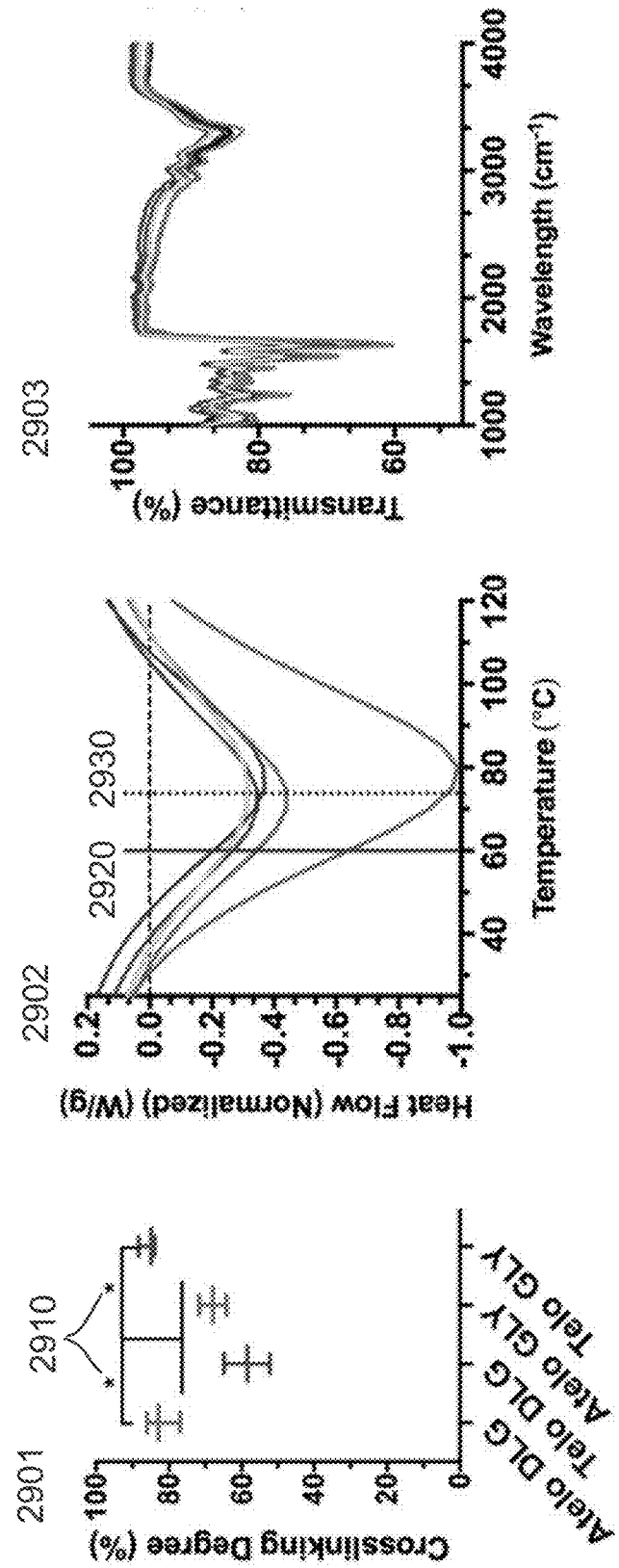
FIG. 29 is graphs summarizing properties of embodiments of the disclosure.

Biophysical characterization using differential scanning calorimetry (DSC) measurements on extruded microfibers revealed an insignificant increase in melting temperatures between the un-crosslinked and the crosslinked microfiber groups, as depicted in graph 2902 in FIG. 29 for the same samples tested for graph 2901. However, the average melting temperature of all the extruded microfibers (74±3° C.) (line 2930 on graph 2902) was significantly higher than that for the human AT (line 2920 on graph 2902) (60° C.) (Wiegnad, Patczai and Lörinczy, 2017), indicative of greater overall structural stability (Sanchez-Ruiz, 1995). FTIR spectra in graph 2903 of FIG. 29 showed no significant peak shifts in the amide I (~1650 $cm^{-1}$), amide II (~1560 $cm^{-1}$), amide III (~1235 $cm^{-1}$), amide A (~3285 cm') and amide B (~2917 $cm^{-1}$) regions, indicating that the secondary structure of microfibers was unchanged after the extrusion as well as the crosslinking process used in this disclosure. Data in graph 2901 is shown as Mean±S.E.M. and is representative of 3 replicates from 2 separate experiments. In graph 2901, indicator 2910 depicts p<0.05.

Figure 30:
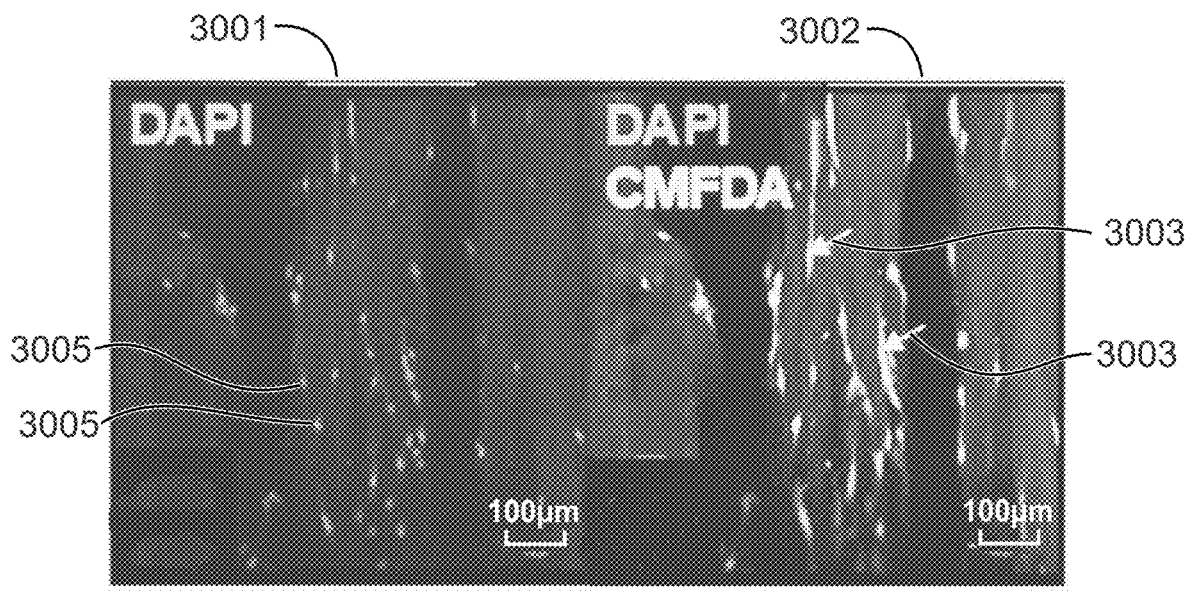
FIG. 30 is images of embodiments of the disclosure.
Figure 31:
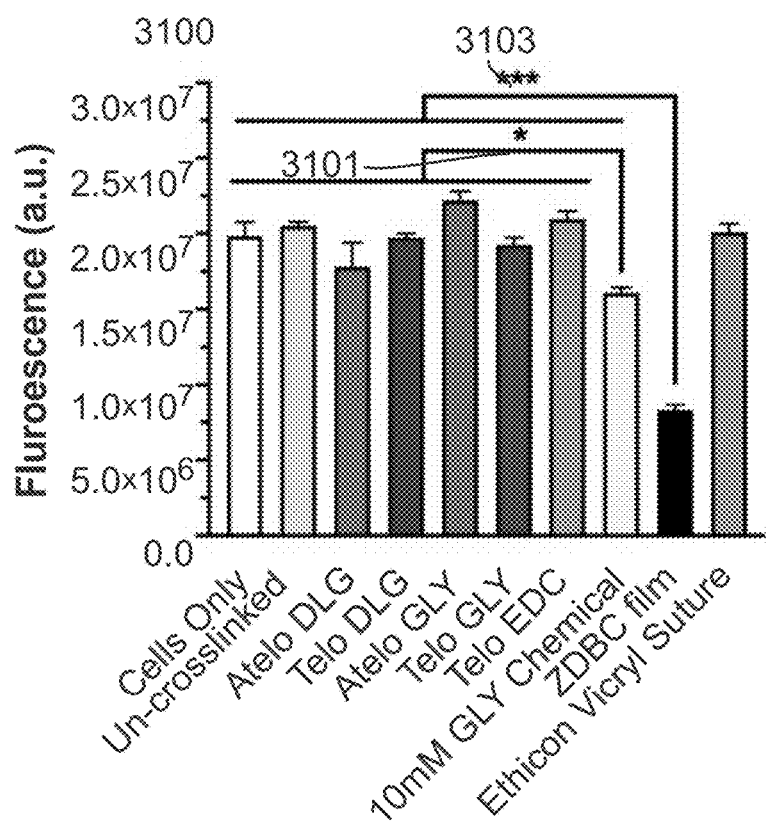
FIG. 31 is a graph summarizing a property of embodiments of the disclosure.
Figure 32:
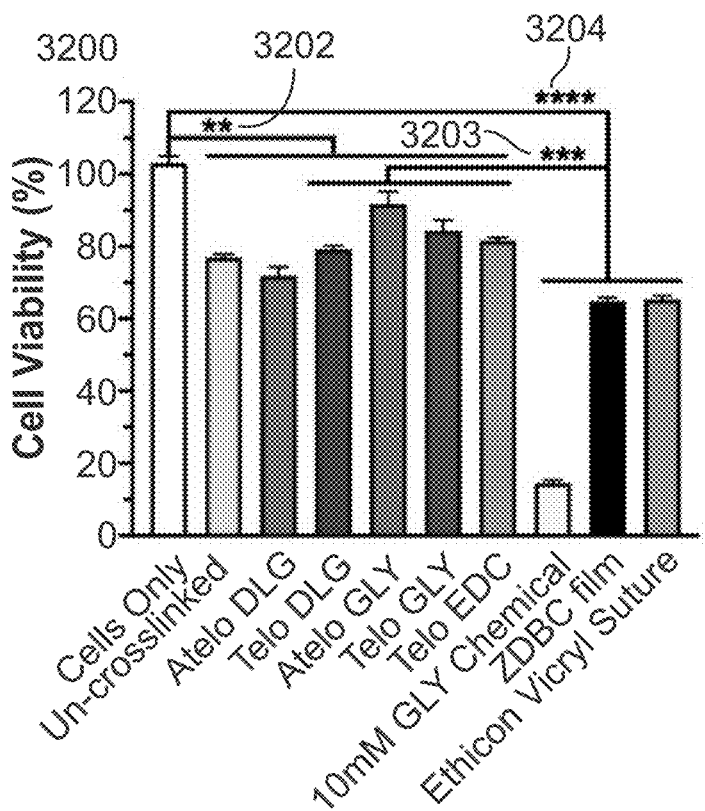
FIG. 32 is a graph summarizing another property of embodiments of the disclosure.
Figure 33:
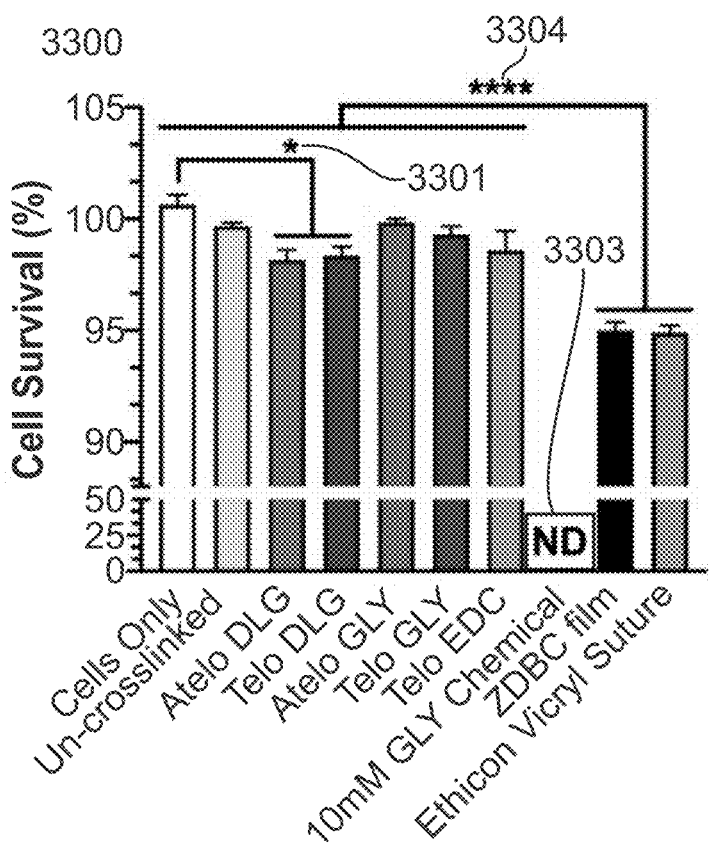
FIG. 33 is a graph summarizing still another property of embodiments of the disclosure.

Cellular attachment, metabolic activity, and cytotoxicity of the extruded microfibers also were determined for embodiments of the disclosure, as shown in illustrations 3001 and 3002 of depiction 3000 in FIG. 30, and in FIG. 31, FIG. 32, and FIG. 33. These figures include Example 3 through Example 6, Comparative Example 2, and other samples. Human tenocytes were used to assess collagen fiber cytocompatibility, as described above. The attachment of tenocytes on Telo GLY microfibers with elongated morphology (Example 5) is shown in illustration 3001 in FIG. 30. About 70% of tenocytes seeded on the Telo GLY microfibers remained attached after 12 days. No significant change in tenocytes metabolic activity over 7 days was noted by AlamarBlue fluorescence, as summarized in FIG. 31 for Example 3 through Example 6, Comparative Example 1, and other samples, when compared to the positive control (Cells only group). However, metabolic activity for cells growing with microfibers from selected fiber groups was significantly higher (p<0.05) than that for negative controls (10 mM glyoxal chemical and ZDBC film). As illustrated in FIG. 32, viability of tenocytes incubated with microfibers was between 75% to 85% compared to tenocytes growing on plastic (100%) when assayed using the MTT reagent. The negative controls (10 mM GLY chemical and ZDBC film) demonstrated significantly lower (p<0.005) tenocyte survival than the "Cells Only", Telo DLG (Example 4), Atelo GLY (Example 5), and Telo GLY (Example 3) groups. Similar results were observed using LDH assay (FIG. 33), wherein the all the extruded microfiber groups except for Atelo DLG and Telo DLG elicited tenocyte viability similar to the "Cells Only" group. As indicated at indicator 3303 of FIG. 33, at the end of 7 days, the 10 mM GLY chemical group did not have enough tenocytes (ND) to be assayed by LDH release into the media. A commercially available coated Vicryl suture from Ethicon, typically recommended in wound closure, provided a comparison. Results indicated that microfiber embodiments of the disclosure exhibited significantly lower cytotoxicity (p<0.005) than the suture using both LDH and MTT assays (FIG. 32 and FIG. 32). Overall, multiple assays were used to establish cytocompatibility of the extruded microfibers.

In particular, image 3001 and image 3002 show representative confocal images of human tenocytes attached to Telo GLY microfibers (Example 3), with DAPI (arrows 3005) and live cell stain (CMFDA, as shown at arrows 3003), respectively, showing cytoplasmic extensions and elongated nuclei. FIG. 31 shows no significant change in metabolic activity of human tenocytes incubated with the crosslinked microfibers assayed using AlamarBlue after 7 days of incubation compared to the cells only group. Metabolic activity was significantly lower in tenocytes incubated with negative controls (ZDBC film and 10 mM GLY chemical) and Vicryl suture in comparison to the microfiber groups. MTT assay results summarized in FIG. 32 revealed a decrease in viability for tenocytes incubated with the microfiber groups compared to the cells only group, but a significant increase compared to negative controls. On the other hand, LDH assay results shown in FIG. 33 show a significant decrease in cell survival for the Atelo DLG (Example 6) and Telo DLG (Example 4) microfiber groups as well as the negative controls. Both MTT and LDH assays were performed at 7 days post incubation with tenocytes. All data in FIG. 32 and FIG. 33 was normalized to the cells only group. (ND) at indicator 3303 indicates that the 10 mM Glyoxal chemical treatment group had a significant arrest in proliferation resulting in insufficient number of cells to detect LDH at the end of the assay timepoint. In these figures, indicator 3101 and indicator 3301 show p<0.05, indicator 3202 shows p<0.01, indicator 3103 and indicator 3203 identifies p<0.005, and indicator 3204 and indicator 3304 identify p<0.0001).

To assess biocompatibility of extruded microfiber embodiments of the disclosure, sterilized microfiber bundles of the selected 4 cross linker groups of Example 3 through Example 6 (Atelo DLG, Telo DLG, Telo GLY and Atelo GLY) were subcutaneously implanted in rats per ISO 10993-6. Microfiber bundles implanted from each of the 4 cross-linker groups in FIG. 23, FIG. 24, FIG. 25, FIG. 26, FIG. 27, and FIG. 28, and the suture control (collagen coated FiberWire®) group elicited a distinct host tissue response characterized by different extents of cellular infiltration, vascularization, collagen deposition and tissue remodeling shown in FIG. 34, FIG. 35, and FIG. 36. Amongst these, glyoxal cross-linked microfiber groups (Telo (GLY), Example 3, or Atelo (GLY) Example 5) showed lower pro-inflammatory response in comparison to DL-Glyceraldehyde (Telo DLG, Example 4, or Atelo DLG, Example 6) cross-linked groups. Representative H & E staining images of the Telo GLY (Example 3) group shown in transverse image 3401 and longitudinal image 3402 of FIG. 34 demonstrated significantly high cellular infiltration compared to the suture control shown in FIG. 36, including transverse image 3601 and longitudinal image 3602. The suture control in FIG. 36 elicited an intense inflammatory response at 4 weeks compared to the microfiber implants.

Figure 35:
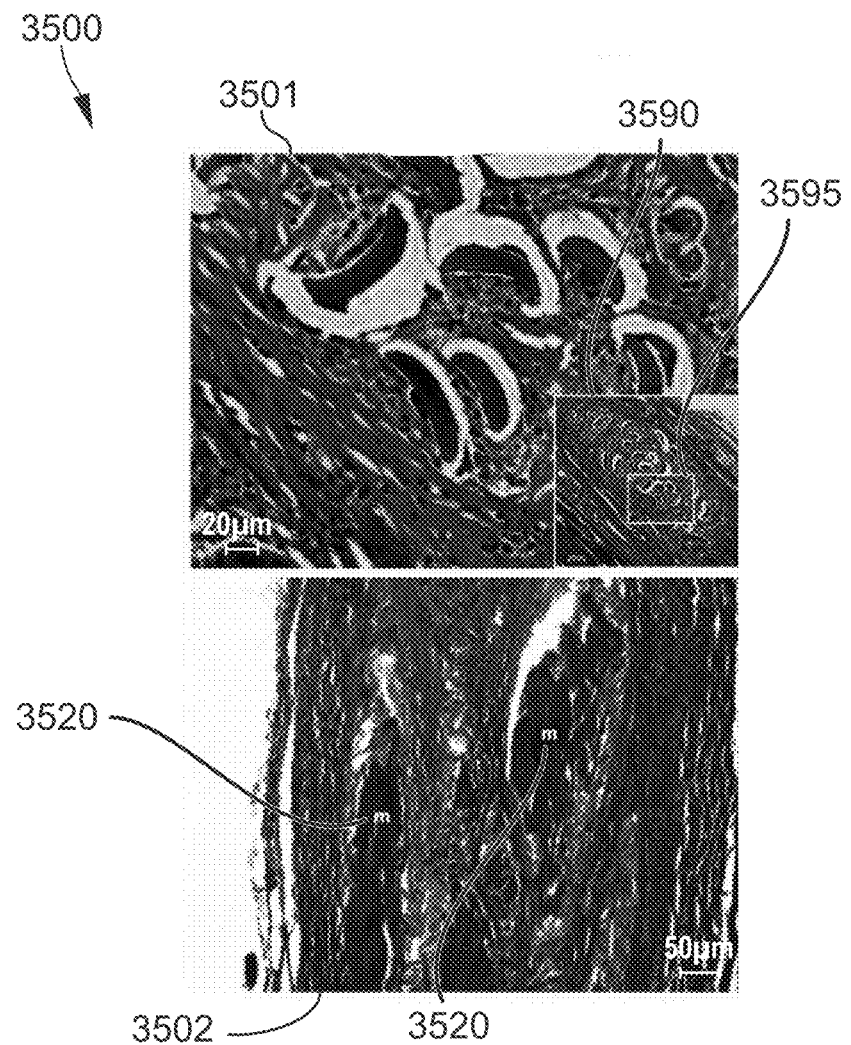
FIG. 35 is magnified images of a microfiber product.

Deposition of newly formed collagen was visualized by Masson's Trichrome staining in native tissue surrounding the Telo (GLY) (Example 3) microfiber implants in image 3501 of FIG. 35. Longitudinal section stained with Masson's Trichrome is as shown in image 3502 of FIG. 35, as well as polarized light imaging of image 3602 of FIG. 36, show deposition of newly formed collagen around the microfibers in an organized fashion.

Figure 34:
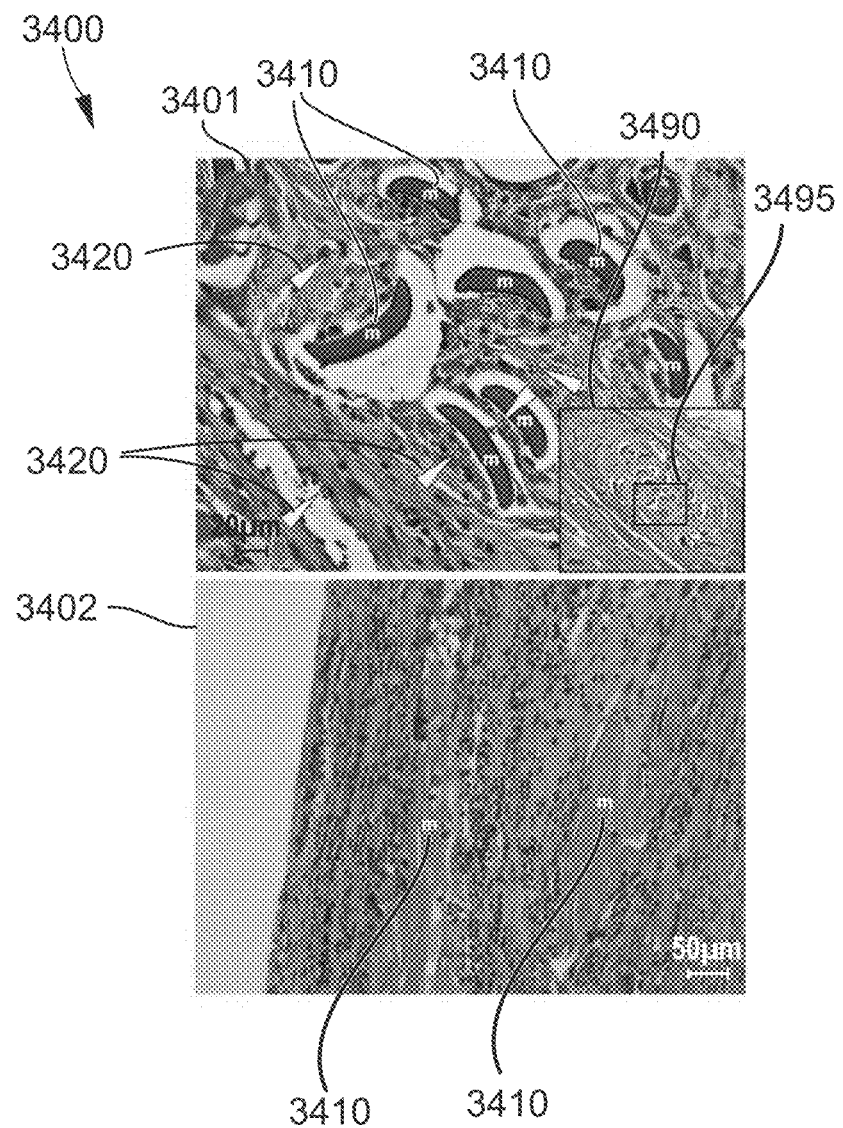
FIG. 34 is magnified images of an embodiment of the disclosure.

Blood vessels and capillaries were identified within the microfiber implants and in surrounding tissues as observed in higher magnification cross-sectional images of H & E stained sections (arrows in image 3401 of FIG. 34).

Figure 36:
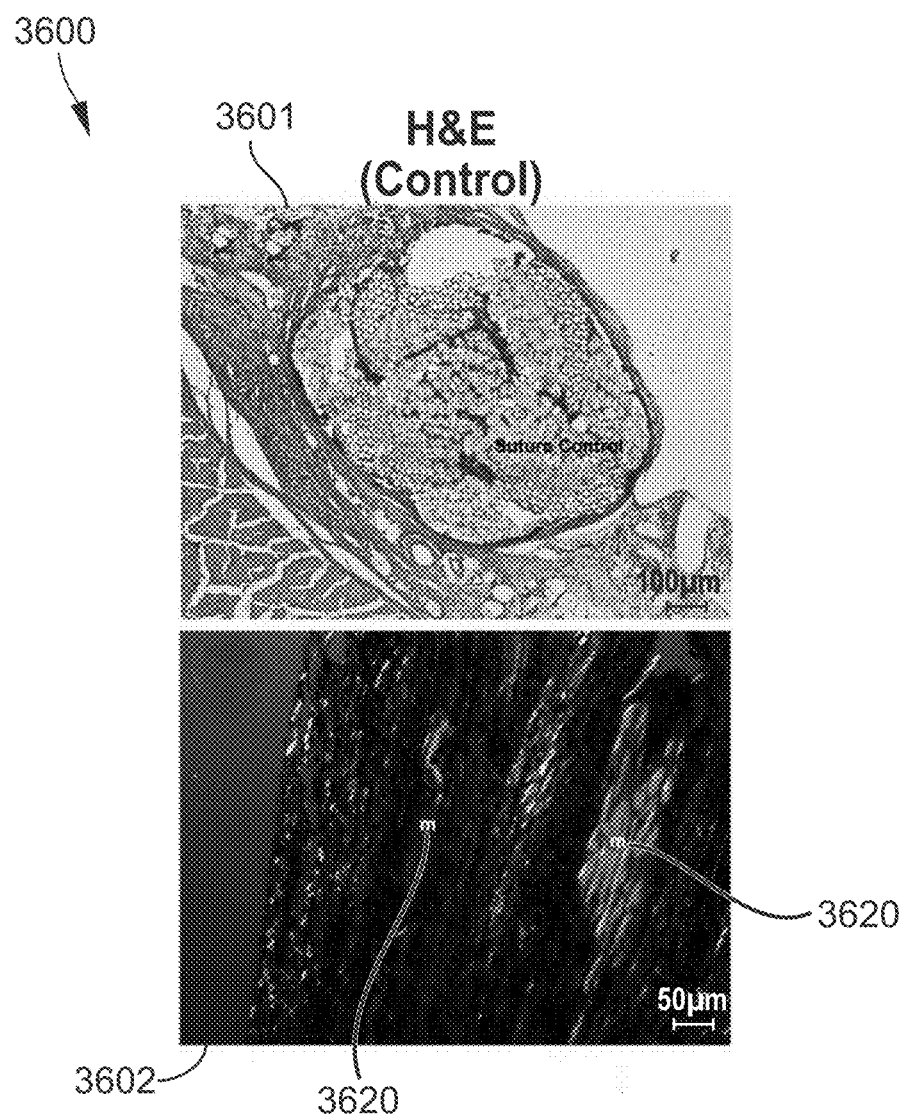
FIG. 36 is magnified images of a control microfiber product.

FIG. 34, FIG. 35, and FIG. 36 are representative images of rat subcutaneous implants at 4 weeks for the Telo GLY (Example 3) group. Image 3401 and image 3501 show microfibers m, identified by arrows 3410, on stained slides illustrating transverse sections of H&E in FIG. 34 and Masson's Trichrome in FIG. 35. Inset 3490 shows the entire section of the H&E implant, and inset 3495 shows the portion depicted in image 3401. Similarly, inset 3590 shows the entire section of the Masson's Trichrome implant, and inset 3595 shows the portion depicted in image 3501. Both image 3401 and image 3501 illustrate significant cellular infiltration. Arrows 3420 in FIG. 34 point at blood vessels within the implants. Image 3601 shows negligible cellular infiltration in control samples, collagen coated FiberWire® using H&E staining. Image 3402 shows H&E and image 35032 shows Masson's Trichrome staining for longitudinal sections of the microfibers' implant. Polarized light image 3602 in FIG. 36 shows aligned microfibers as well as newly formed collagen surrounding the implants. Image 3402, image 3502, and image 3602 demonstrate the formation of new aligned collagen in native tissue surrounding the implants. The legend "Suture Control" on image 3601 identifies the collagen coated FiberWire®.

Figure 37:
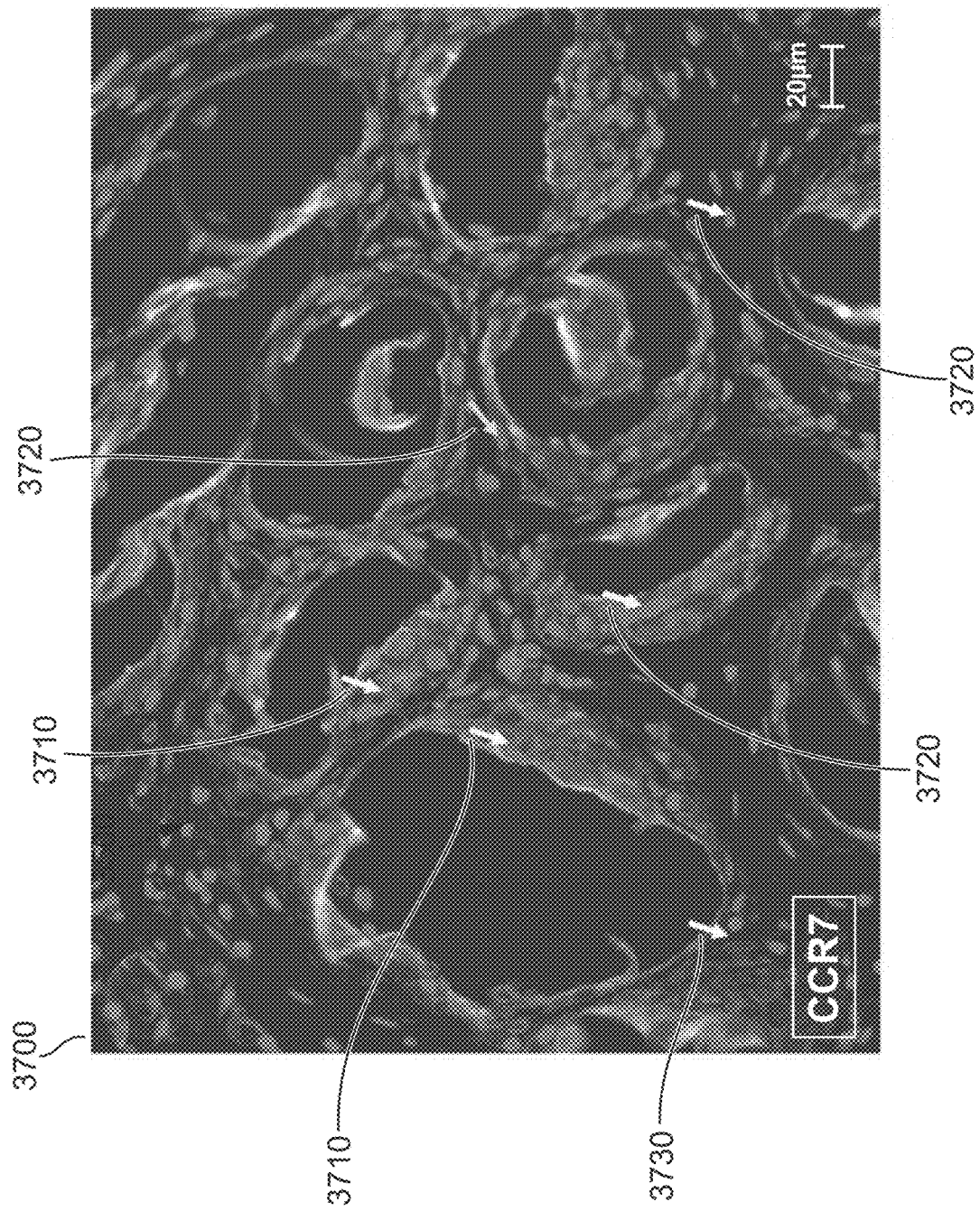
FIG. 37 is an image of features of an embodiment of the disclosure.
Figure 38:
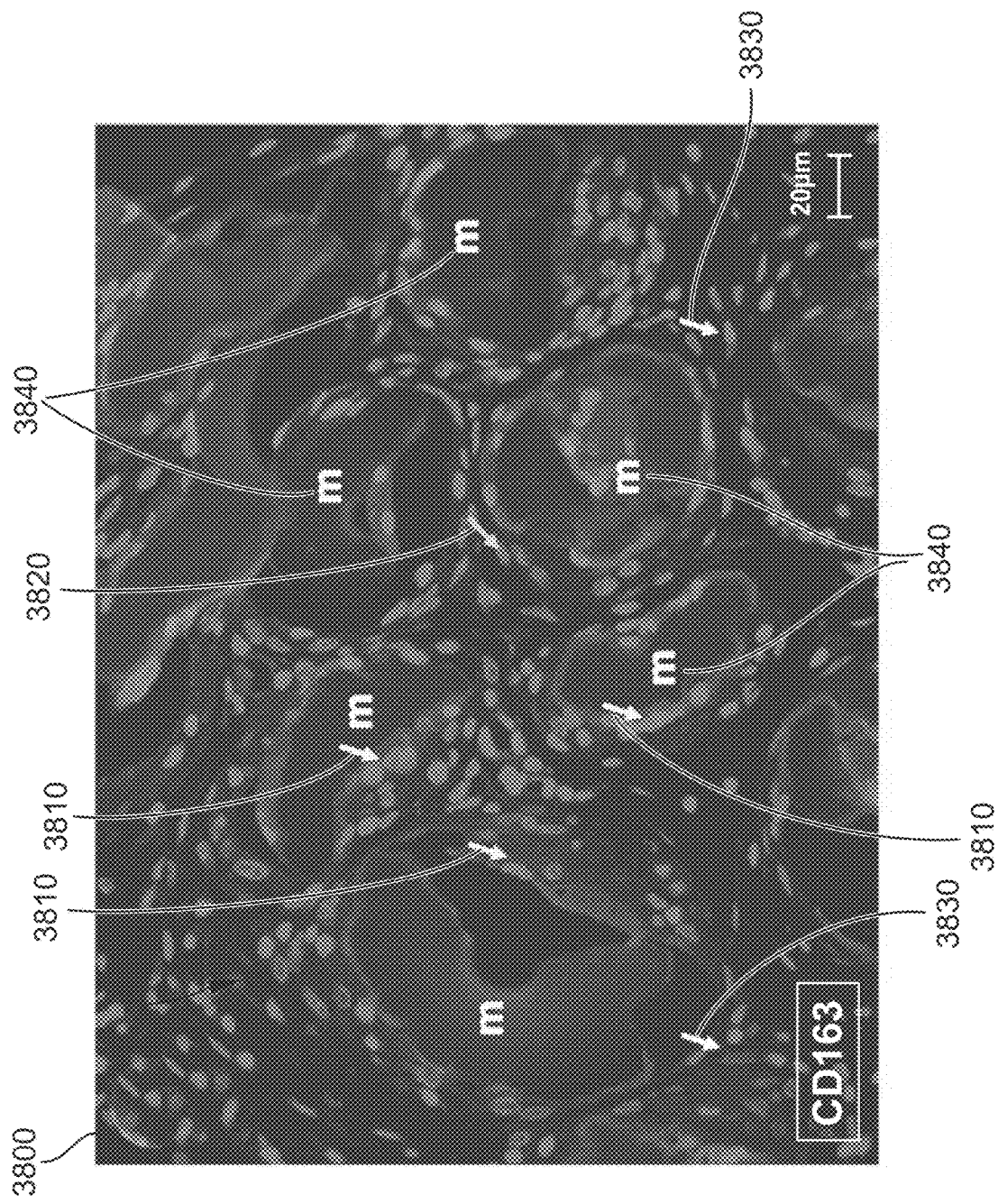
FIG. 38 is an image of features of an embodiment of the disclosure.
Figure 39:
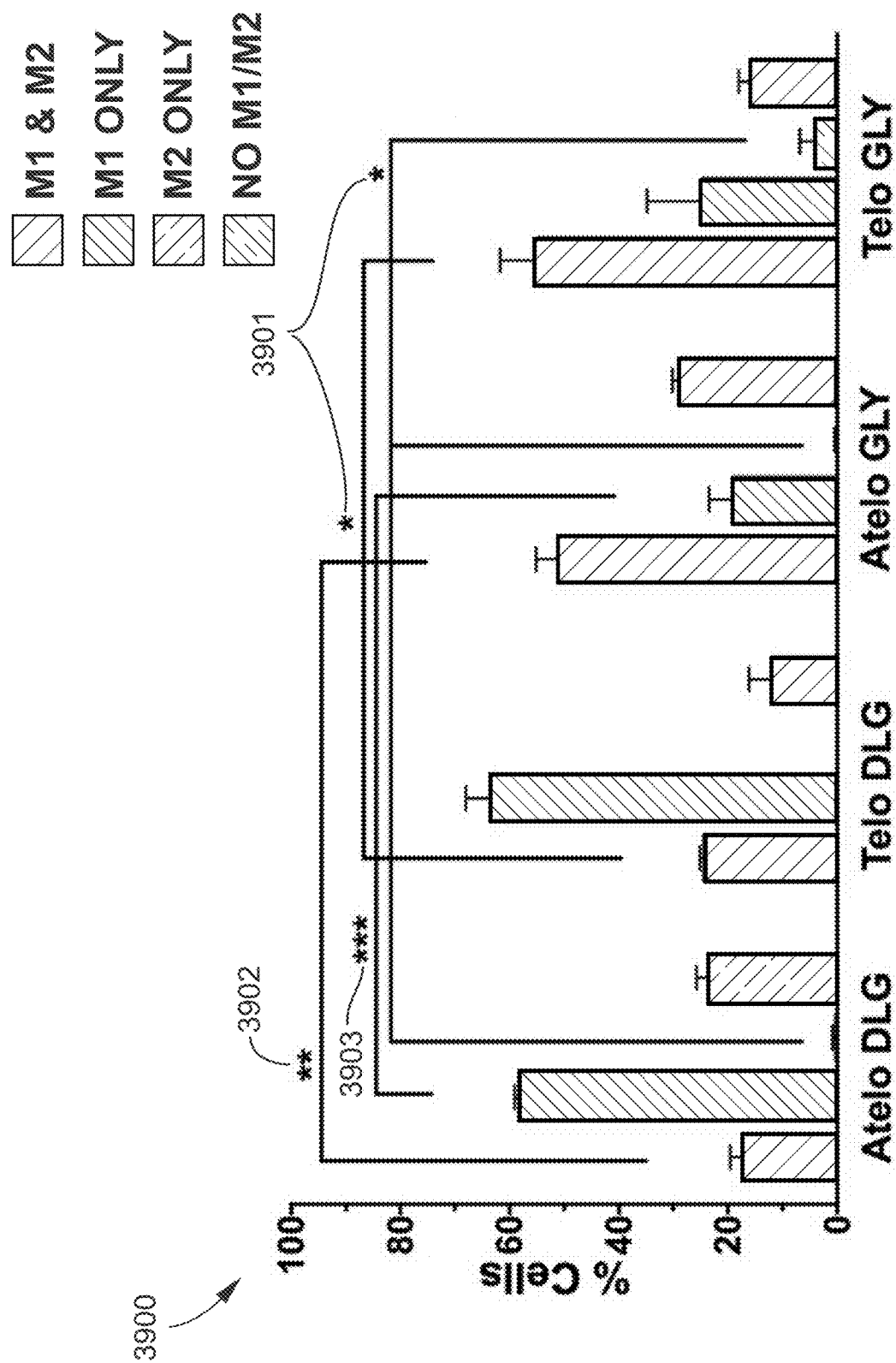
FIG. 39 is a graph summarizing features of embodiments of the disclosure.

Immunostaining was used to determine extents of macrophage polarization in native tissue around microfiber implants from 4 crosslinker groups, FIG. 37 and FIG. 38 are representative immunofluorescent images showing expression patterns of CCR7 (M1) (image 3700 on FIG. 37) and CD163 (M2) (image 3800 on FIG. 38) macrophage phenotype in the native tissue of rats surrounding Telo GLY (Example 3) microfiber implants at 4 weeks. FIG. 38 shows quantitation of the percentage of macrophages that expressed both M1 and M2, M1 only, M2 only, or no M1/M2 phenotype. Glyoxal cross-linked groups (Telo (GLY), Example 3, and Atelo (GLY), Example 5) demonstrated significantly higher proportion of macrophages expressing M1 and M2 phenotype (about 40%) compared to the DL-Glyceraldehyde cross-linked groups (Telo DLG, Example 4, and Atelo DLG, Example 6), as shown in graph 3900 of FIG. 39. Furthermore, between the Telo (GLY), Example 3, and Atelo (GLY), Example 5, groups, Telo GLY implants elicited a small subset of cells expressing M2 only phenotype (6%), while the rest of the groups had negligible M2 only phenotype; Atelo GLY (0.2%), Telo DLG (0%) and Atelo DLG (0%) (FIG. 39). There was a significantly higher proportion of cells with M1 phenotype in the DL-Glyceraldehyde crosslinked groups; Telo DLG (64%) and Atelo DLG (58%) compared to the glyoxal crosslinked groups; Telo GLY (24%) and Atelo GLY (19%). Staining with appropriate controls, as described above, revealed negligible non-specific background staining (not shown). Sectioning artifacts of the suture control samples, and significant background staining, made it difficult to perform this analysis on these samples.

Representative immunofluorescent image 3700 and image 3800 show examples of the host macrophage response to the Telo (GLY), Example 3, microfibers, identified as m at arrows 3840, at 4 weeks. Arrows 3710 and arrows 3810 indicate examples of cells expressing both M1 and M2. Arrow 3720 and arrow 3820 indicate examples of cells expressing M1 only. Arrows 3730 and arrows 3830 indicate cells expressing M2 only phenotype. Arrows 3840 point to microfiber bundles, identified by m. Graph 3900 of FIG. 39 shows the % of cells expressing M1 and M2, M1 only, M2 only, or no M1/M2 phenotype for the 4 groups of cross-linked microfibers. Results from this analysis show initiation of pro-regenerative M2 macrophage phenotype in all microfiber groups tested. Glyoxal cross-linked fiber groups showed higher proportion of cells with M1 and M2 phenotype compared to the DL-Glyceraldehyde cross-linked fiber groups. Furthermore, Telo GLY group had a small but significant subset of M2 only macrophages. In graph 3900, indicator 3901 identifies $p<0.05$, indicator 3902 indicates $p<0.01$, and indicator 3903 indicates $p<0.005$).

Figure 40:
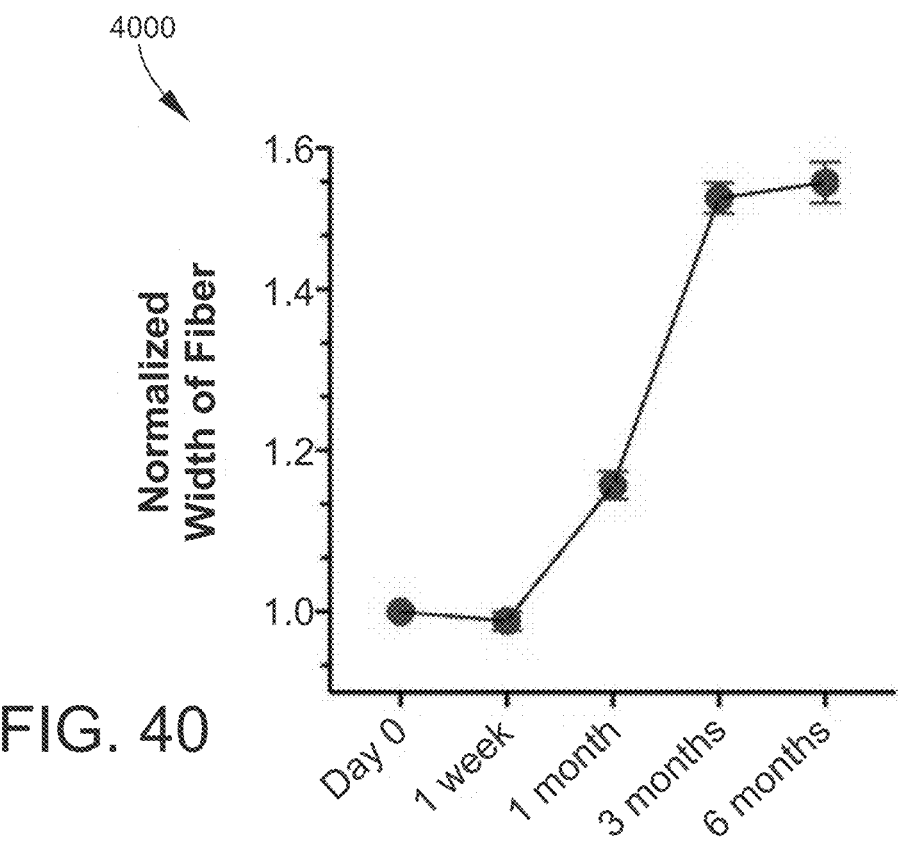
FIG. 40 is a graph summarizing how size of an embodiment of the disclosure changes with time.
Figure 41:
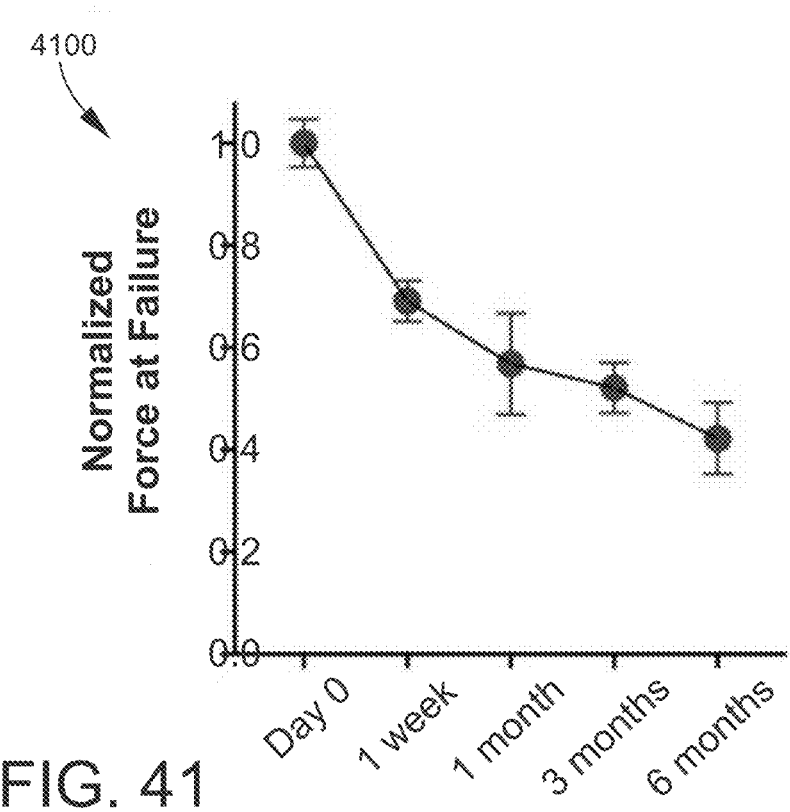
FIG. 41 is a graph summarizing how a mechanical property of an embodiment of the disclosure changes with time.
Figure 42:
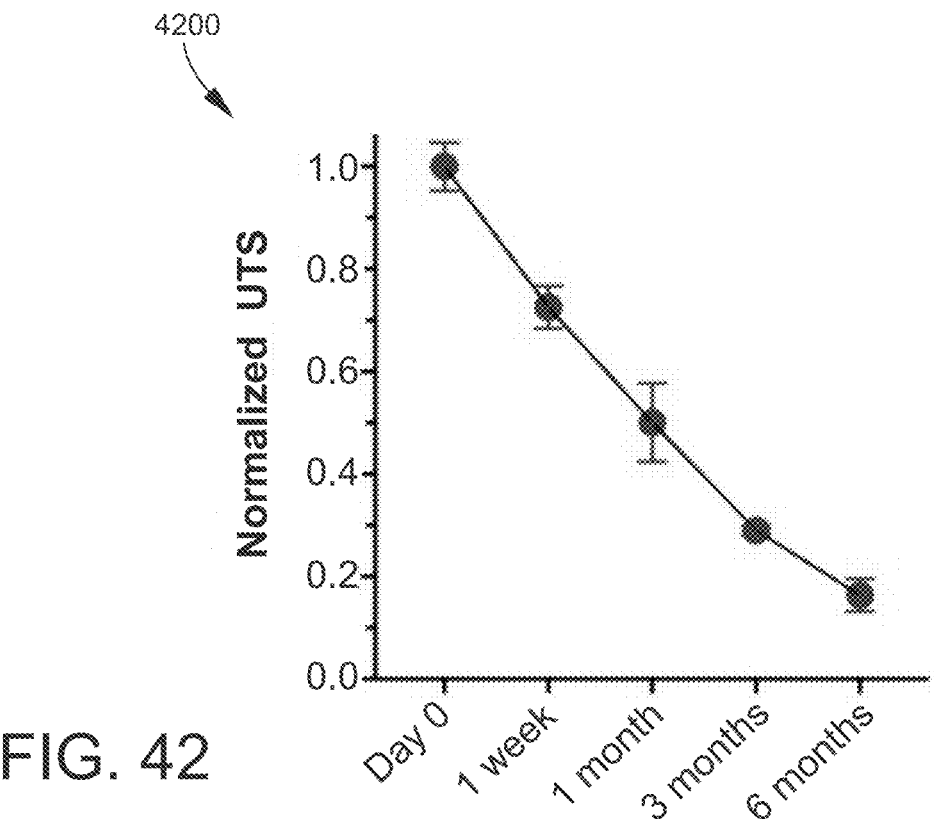
FIG. 42 is a graph summarizing how another mechanical property of an embodiment of the disclosure changes with time.
Figure 43:
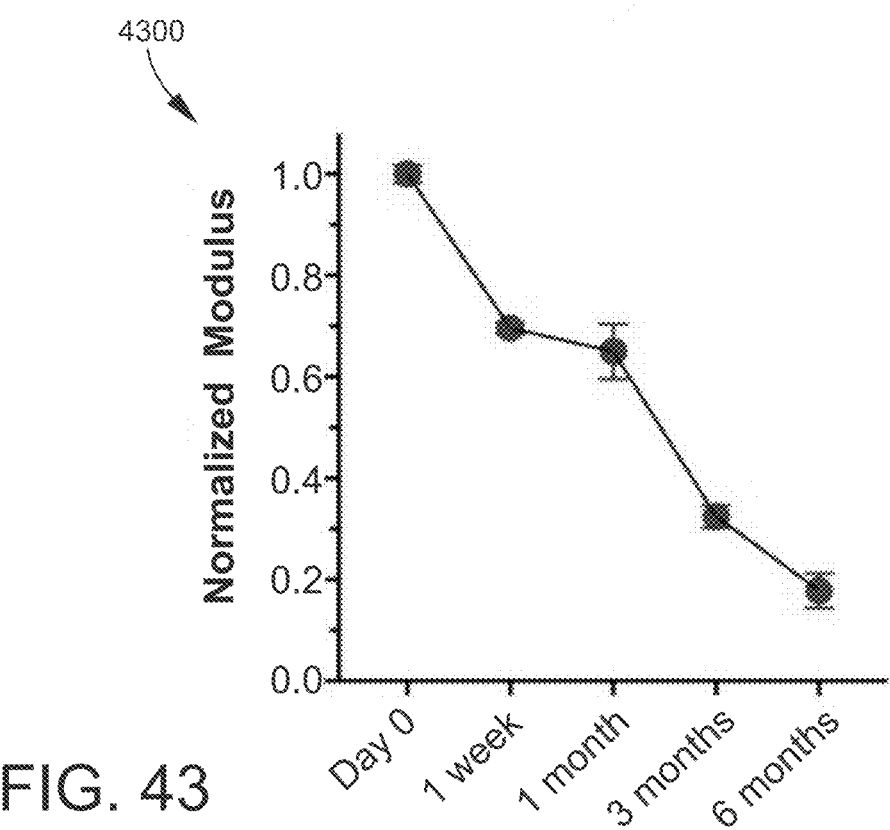
FIG. 43 is a graph summarizing how yet another property of an embodiment of the disclosure changes with time.

The effect of long-term hydration was determined for embodiments of the disclosure of microfibers in culture media on mechanical properties and degree of swelling. Because Telo (GLY), Example 3, microfibers showed optimal mechanical properties, cytocompatibility, and biocompatibility, this group was further tested for long-term stability mimicking in vitro physiological conditions. Incubation in EMEM (Eagle's Minimum Essential Medium) led to increase in microfiber width by 53% (36.4±1.1 µm, Day 0 to 56.0±1.6 µm, 6 months) in 6 months as shown by graph 4000 in FIG. 40. This graph shows the degree of swelling of wet microfibers over time. The swelling was accompanied by a significant loss in mechanical properties. Graph 4100 in FIG. 41 shows that mean force at failure decreased by 54% from its initial value in 6 months. Mean UTS (graph 4200 in FIG. 42) and modulus (graph 4300 in FIG. 43) also reduced by 82% from the starting timepoint in 6 months. There was no significant change in strain at break (%) between Day 0 and 6 months of incubation (graph 4400 in FIG. 44).

Therefore, FIG. 40, FIG. 41, FIG. 42, FIG. 43, and FIG. 44 show that Telo GLY microfibers were stable and did not dissolve when incubated in conditions mimicking in vitro biological environment (sterile cell culture media in a humidified incubator maintained at 37° C. and 5% CO2) for up to 6 months.

Figure 44:
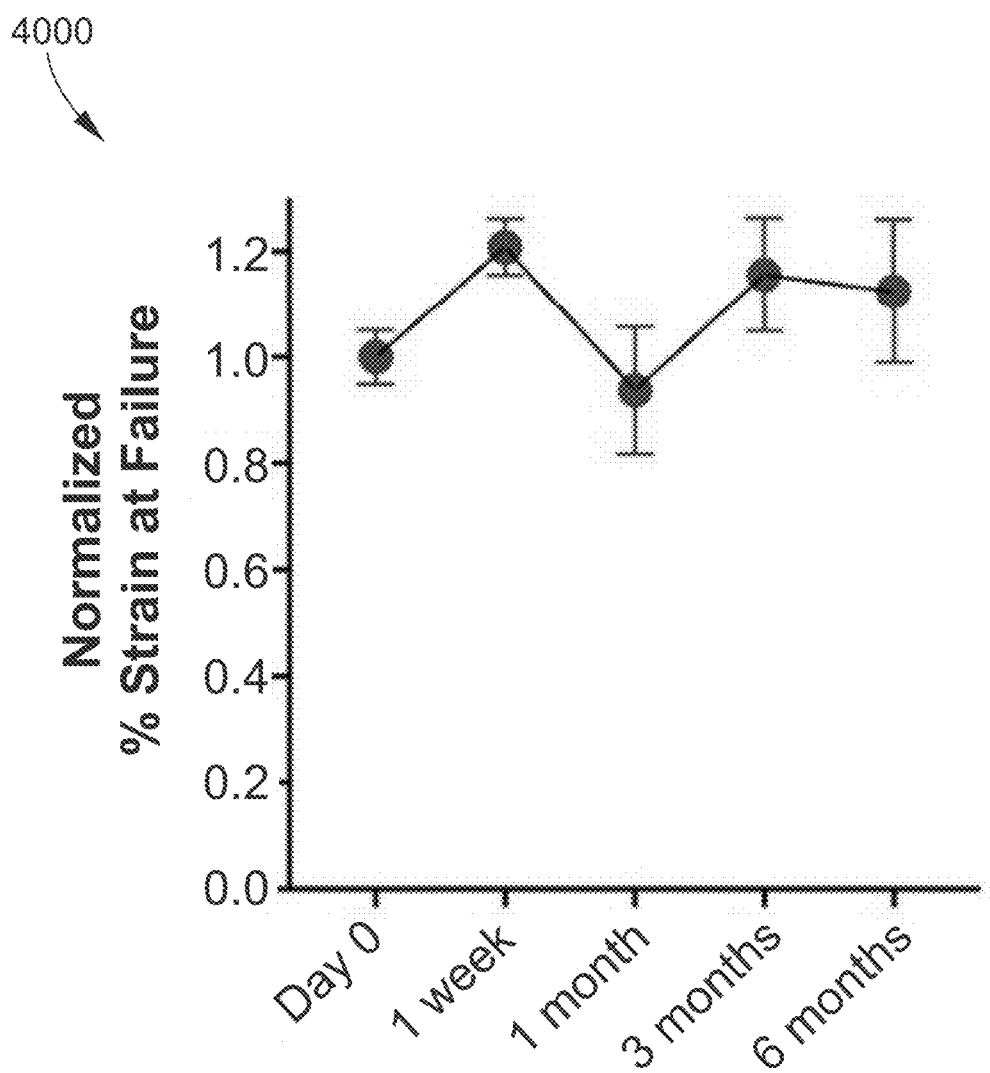
FIG. 44 is a graph summarizing how still another property of an embodiment of the disclosure changes with time.

As can be seen from the figures, mechanical stability of Telo GLY microfibers incubated in sterile EMEM and under tension assessed after 1 week, 1 month, 3 months and 6 months in a humidified incubator at 37° C. and 5% CO2 shows that Telo GLY microfibers at the end of 6 months swell by 50% (FIG. 40), lost 60% of the Force at Failure (FIG. 41), lost 80% of UTS (FIG. 42), and lost 80% of Modulus (FIG. 43) compared to Day 0. However, there was no significant change in % Strain at failure at the end of 6 months (FIG. 44). All the values depicted in these figures have been normalized to a value of 1 for Day 0. The continuous lines in these figures have been drawn by inspection only to serve as a guide to the reader. Data shown as mean±S.E.M. and is representative of at least 5 replicates.

SDS-PAGE was used to compare the collagen starting materials (lyophilized telo- or atelo-collagen), un-cross-linked, and cross-linked microfibers. Collagen starting materials readily dissolved in 50 mM HCl after overnight agitation. However, the extruded microfibers did not go into solution at a concentration of 0.5 mg/ml and so provided no bands. To confirm the presence or absence of collagen in acid extracts of microfibers, these extracts were run with the solution of starting material and a pre-stained molecular weight marker (HiMark, Invitrogen, CA) on a gradient gel (3%-8%) (Invitrogen). SimplyBlue™ (Invitrogen, CA) was used to stain gels followed by rinses with deionized water to de-stain them. The gels were then imaged under white light to view all visible protein bands. Thus, SDS-PAGE shows that the extruded fiber from groups with maximum UTS and un-cross-linked fibers were resistant to acid hydrolysis when compared to the acidified starting materials that show type I collagen fingerprint with bands characteristic of monomeric regions at about 115 kDa, dimeric regions at about 230 kDa, and trimeric regions at about 460 kDa regions.

FIG. 45 summarizes mechanical tensile properties of some of the best performing (hydrated) cross-linked collagen fibers published in literature, compared to an embodiment of the disclosure.

In summary, this disclosure is directed to a novel microfluidic extrusion process to manufacture type I collagen microfibers with precision, consistency, and scalability as biocompatible fibers to be used in indications ranging from natural sutures to engineered connective tissue. This disclosure reveals the biomanufactured glyoxal crosslinked telocollagen microfiber embodiments of the disclosure demonstrate dry and wet-tensile properties superior to prior crosslinked collagen extruded microfibers (Paul and Bailey, 2003; Caruso and Dunn, 2004; Zeugolis, Paul and Attenburrow, 2009; Enea et al., 2011).

While many prior studies do not report whether tensile testing was performed on hydrated fibers or provide arguably misleading results for dry fibers, or does not disclose how the fibers were wetted if fully hydrated, results of embodiments of the disclosure herein provide dry and hydrated properties of optimized crosslinked fibers with a detailed methodology for testing, which is critical for comparisons and growth within the field.

Collection of fibers on a grooved drum led to significant alterations in structural and hydrated mechanical properties of all the crosslinked microfiber (see FIG. 22, FIG. 23, FIG. 24, FIG. 25, FIG. 26, FIG. 27, and FIG. 28). Mechanically, this improved strength may be related to tempering, thinning, and improved molecular alignment to the ribbons which were once fibers, resulting in fiber tensile properties stronger than the ACL, Achilles tendon, dermis, or any other soft connective tissue.

In embodiments of the disclosure, determining the degree of crosslinking mechanism efficiency is emphasized. Insufficient crosslinking can lead to lower tensile strengths while overuse of chemical crosslinker can lead to residues of crosslinker on the surface of the microfibers resulting in cytotoxicity. The ninhydrin assay (FIG. 36) revealed that groups with maximum crosslinking degree were those that were crosslinked for 72 hours (Telo GLY and Atelo DLG), which also correlated with a significant increase in tensile strength. The chemistry of crosslinking using aldehydes involves the formation of Schiff's base type compounds with functional amino groups in collagen, leading to strong molecular bonds (Fathima et al., 2004).

Chemical analysis of embodiments of extruded microfibers revealed that these were further resistant to acid hydrolysis. The microfluidics apparatus, or setup, disclosed herein generated microfibers with chemical stability higher than the lyophilized starting material suggesting tight packing of the collagen molecules in the microfibers resulting in a stable higher order structure and suggests low internal moisture content. Such higher order structure has been reported in native connective tissues (Benjamin, Kaiser and Milz, 2008; Wang, Guo and Li, 2012). Integrity of the secondary structure in the extruded microfibers was confirmed from FTIR analysis shown in FIG. 29 which also suggested that neither the extrusion process nor the crosslinking technique denatured the collagen.

While crosslinking of collagen in a biomimetic might help improving tensile properties, degradation of chemicals (e.g. glutaraldehyde) used for crosslinking can be toxic (Gough, Scotchford and Downes, 2002; Umashankar, Kumari and Mohanan, 2012). Amongst other chemicals that exhibit somewhat less cytotoxicity, EDC or EDC/NHS as crosslinker has been a popular basic research choice for collagen microfibers (Enea et al., 2011; Ahmad et al., 2015; Shepherd et al., 2015). However, there is only a negligible improvement in tensile strength and noted toxicity with these classic crosslinkers, making them poorly suited for use in connective tissue repair. We show in this study the development of mechanically superior extruded collagen microfibers chemically crosslinked with either glyoxal or glyceraldehyde, which are highly cytocompatible (see FIG. 30, FIG. 31, FIG. 32, and FIG. 33) and biocompatible in vivo as shown in FIG. 34, FIG. 35, and FIG. 36), per standardized ISO 10993 testing as is commonly required for USFDA approval. Furthermore, collagen microfibers cross-linked with glyoxal are resistant to acid hydrolysis, demonstrate ultrastructural features down to the near molecular level, and remain stable in cell culture media for at least 6 months with the ability of a single microfiber to retain around between about 30% and about 50%, typically about 40%, of their initial load carrying capacity and a UTS value higher than native ACL (see FIG. 40, FIG. 41, FIG. 42, FIG. 43, and FIG. 44).

Augmenting suture repair of ACL or Achilles tendon with collagen based microfibers or using a collagen-based braided suture in wound healing as described herein requires the collagen-based material not only to support the tissue mechanically but also to promote tissue remodeling at a reasonable rate (Dunn, Avasarala and Zawadsky, 1993). Therefore, for biomedical application, in vitro and/or in vivo biocompatibility tests are critical to establish the effects of these chemically crosslinked microfibers on cytotoxicity, inflammatory response, and regenerative response. Embodiments of extruded microfiber bundles of the disclosure were cytocompatible and demonstrate minimal toxicity to human tenocytes. Microfluidic extruded microfibers of the disclosure further supported the attachment of human tenocytes and assumed the elongated shape as observed on connective tissue (Benjamin, 2010). Biocompatibility has been defined as the ability of an implant to "locally trigger and guide non-fibrotic wound-healing, reconstruction and tissue integration" (Ratner, 2011). Cross-linked microfiber bundle implants following subcutaneous implantation in rats for 4 weeks manifested low (glyoxal groups) to moderate (glyceraldehyde groups) inflammatory response, with the glyoxal-telocollagen group demonstrating initiation of a pro-regenerative response. Additionally, long-term stability data and rat histology images indicated stability of the microfibers for up to at least 6 months in vitro and 4 weeks in vivo. Thus, embodiments of the disclosure are able to maintain strength in vivo for at least about 1 month and in vitro for at least about 3 months, and up to about 6 months.

Macrophages are a heterogenous mix of mononuclear cells that are activated in the host as a response to tissue damage (Mosser, 2003; Gordon and Taylor, 2005) such as, during implantation of materials. Macrophage phenotype polarization at the interface of the implant and the host tissue (Kasner et al., 2009; Brown et al., 2012) is important in determining the potential of the host to overcome pro-inflammatory signals and transition towards tissue repair and remodeling in response to the surgical implant. Macrophage phenotype has been broadly characterized as M1, or "classically" activated, possessing pro-inflammatory signals and M2, or "alternatively" activated, possessing immunoregulatory or tissue remodeling characteristics (Mills et al., 2000). However, it is important to note that activated macrophages possess plasticity in a way that they are able to switch from M1 to M2 and from M2 to M1 phenotypes easily. This plasticity is triggered by changes in the local microenvironment (Porcheray et al., 2005; Stout et al., 2005). Due to this, macrophages may also adopt transitional characteristics of both M1 and M2 phenotype (Brown and Badylak, 2013). In embodiments of the disclosure, the proportion of cells exhibiting M1, M1 and M2, or M2 phenotypes were determined. These determinations suggest the following: (1) at 4 weeks of implantation the glyoxal crosslinking groups had cells with more M1 and M2 or M2 only phenotype indicating that a tissue remodeling response had been initiated by the host at 4 weeks. This suggests that the microfibers from the glyoxal groups were most biocompatible. To the best of our knowledge, such in depth analysis of immunologic response has not been performed using crosslinked collagen microfibers.

Incorporation of collagen into sutures for wound healing has been a challenge. However, this disclosure provides a method and apparatus for manufacture of effective products. A collagen coated FiberWire® non-resorbable suture (the only collagen based synthetic suture available in the market) was used as control for investigation herein. This FiberWire® showed limited cellular infiltration leading to very little ingrowth or regeneration of native tissue around the implants. In contrast, glyoxal cross-linked collagen microfiber embodiments of the disclosure in the form of suturelike bundles showed significant cellular infiltration with newly-formed collagen in the surrounding tissue, indicative of regenerative healing.

Embodiments of the disclosure illustrate that microfluidic extrusion of type I clinical quality collagen fibers cross-linked with glyoxal exhibit exemplary tensile strength, structural stability, cytocompatibility, and biocompatibility, exceeding prior reported pure collagen made by other biomanufacturing processes. Using glyoxal to stabilize collagen fibers presents a clinically relevant, safe, and effective method for additive biomanufacturing of collagen microfibers. These optimized collagen microfibers can readily be manufactured into diverse biomedical applications ranging surgical suture, ligament internal braces, tissue engineered ligaments, tendons, and other strong, fibrous tissues, designed for significantly improving human health.

Example 7

Collagen solution and formation buffer were prepared. Clinical grade lyophilized atelocollagen (Symatese, France) in an amount sufficient to form a solution having a concentration of 1.6% (w/v) was dissolved in 0.05 M acetic acid in a closed polypropylene container. The solution was stirred overnight at room temperature at 180 rpm. The total volume of the solution was less than half of the volume of the container to ensure uniform mixing. On the next day, the acidified collagen mixture was spun down in a centrifuge at 730 g for 5 minutes. The solution was degassed for 2 minutes and spun down for 10 minutes at 730 g to remove bubbles. The resultant acidified atelocollagen was pulled up into eight 20 mL syringes (Hsw® Norm-Ject® Sterile Luer-Lock Syringes, VWR) to be used directly with high-output collagen microfiber extrusion equipment illustrated in FIG. 46.

To prepare the formation buffer, to 100 ml of Milli-Q water, 10 gm PEG (polyethylene glycol) (35 KDa, Chem-Cruz), 0.686 gm TES (N-Tris(hydroxymethyl)methyl-2-aminoethanesulfonic acid) (Sigma Aldrich), 0.790 gm Sodium Chloride (Sigma Aldrich), 0.414 gm Sodium Phosphate Monobasic (Baker Analyzed), and 1.21 gm Sodium Phosphate Dibasic (Sigma Aldrich) were added. This mixture was stirred overnight at room temperature in a glass beaker on a stir-plate at 400 rpm. On the next day, the pH of this solution was adjusted to 8 by adding 10 M Sodium Hydroxide (Sigma Aldrich) and the solution then was filtered using a 0.45 μm filter.

On the day of the extrusion, to 800 ml of Milli-Q water, 200 ml of ethanol (Fisher Scientific) was mixed to obtain a 20% ethanol solution for the dehydration bath.

FIG. 46 shows a portion of system 4600, in which the acidified atelocollagen was processed. A syringe array pump was mounted to cooperate with rotatable plate 4601 and all 8 syringes. Example fiber bundles were made with and without twisting. The fiber bundle travelled through the formation bath and became stronger as the buffering solution neutralized the acid and formed fibrils. The twisted and non-twisted bundles then entered the 20% aqueous ethanol dehydration bath, which removes water and further strengthens the fiber. A tensioning rig keeps constant tension on the fiber bundle until the bundle is deposited onto a grooved spool (not shown) at the end of the bath. The tension in the fibers aided in drawing and organizing the collagen for strength and stability. The spooled collagen then was dried, crosslinked in glyoxal, and used for forming 3D grafts.

For post-extrusion chemical crosslinking, un-crosslinked taut collagen fiber bundles were collected on big grooved spools were air dried for half hour and then submerged into a solution of crosslinker in 70% ethanol solution in a large acrylic tube and then placed on a rocker at 1 rpm. The aqueous ethanol medium ensured that microfibers remained dehydrated throughout the crosslinking period. After crosslinking, microfibers were stored in a desiccator until further tests were performed.

The chemical crosslinker used was glyoxal, a dialdehyde, at a concentration of 10 mM. The chemistry of crosslinking using aldehydes involves the formation of Schiff's base type compounds with functional amino groups in collagen, leading to strong molecular bonds.

Mechanical properties of the thus-produced single fiber bundles were generated using a "discrete fiber" test method wherein the cross-sectional area of individual fiber bundles and a known quantity of fiber bundles on a cartridge were averaged to determine the ultimate tensile strength (UTS), modulus, and strain at failure (%). Diameters of fibers were measured from analyzing images obtained at 10 different points on 3 separate, 1.5-inch long, fiber bundles using an inverted light microscope (Axio Vert.A1 Model, Zeiss, Germany) and ImageJ software (NIH Shareware, Bethesda, Md.).

Figure 55:
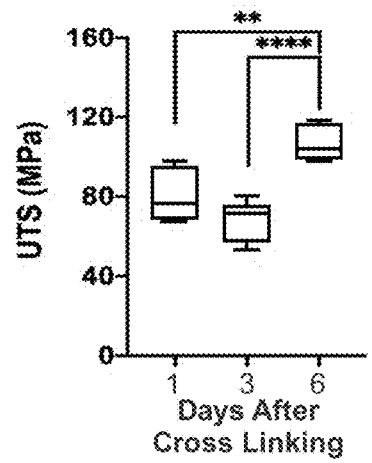
FIG. 55 summarizes the properties and characteristics of an embodiment of the disclosure.
Figure 56:
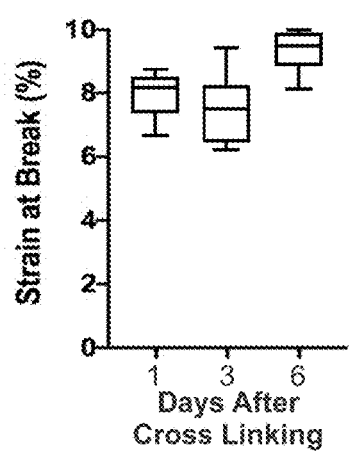
FIG. 56 summarizes the properties and characteristics of an embodiment of the disclosure.

FIG. 47 through FIG. 51 show results from mechanical testing of the fiber bundles under different test conditions, i.e., for non-twisted fibers and for twisted fibers. There were no significant differences between fiber types. FIG. 52 through FIG. 56 show results from mechanical testing of non-twisted fiberbundles after cross-linking in glyoxal at various times. There were differences at levels $p<0.01$ () in peak load (FIG. 53) and UTS (FIG. 55) and at $p<0.001$ (**) in modulus (FIG. 54) and UTS (FIG. 55).

Figure 57:
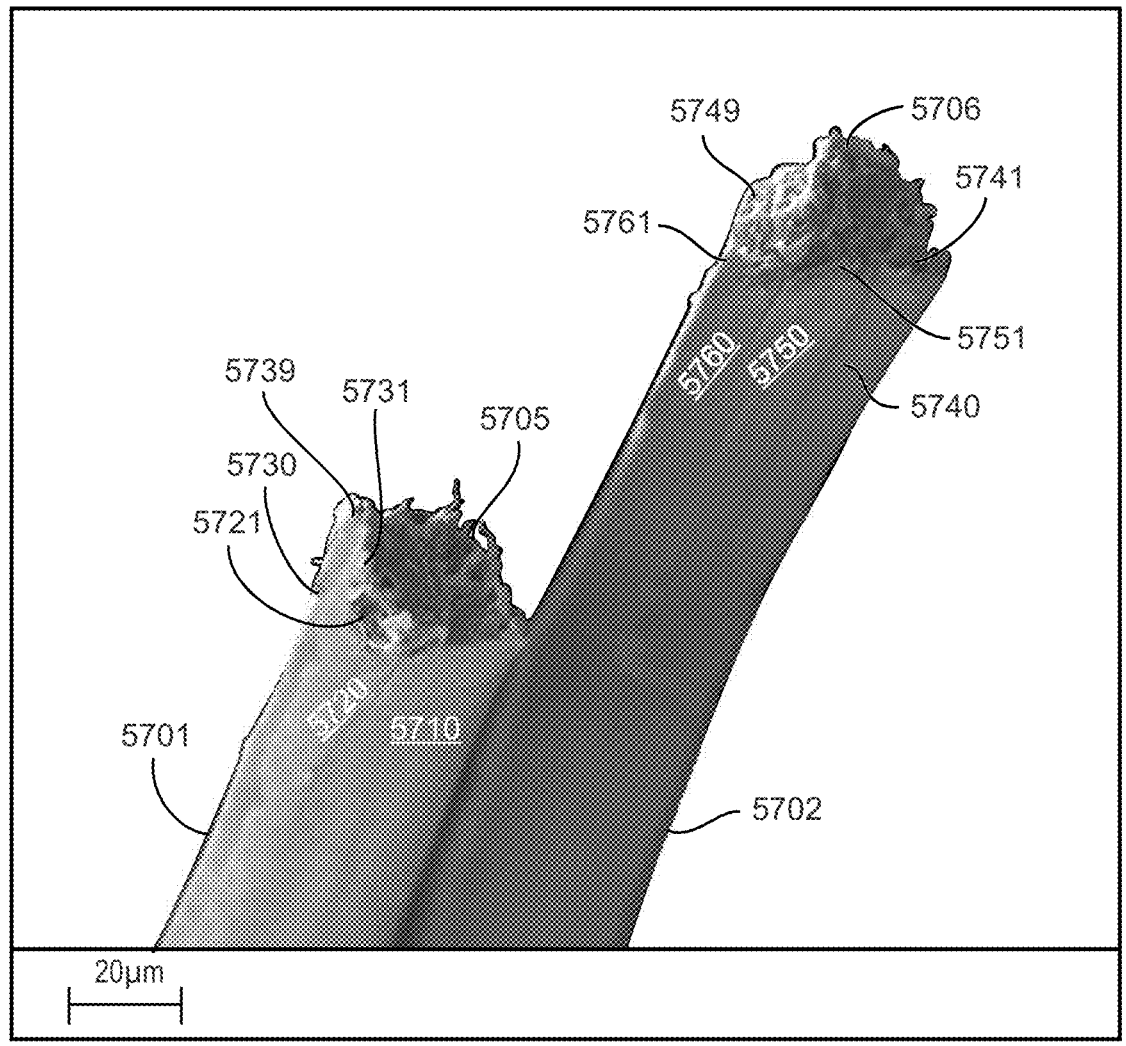
FIG. 57 is an SEM image of an embodiments of the disclosure.

FIG. 57 is a cross-sectional image of microfiber bundles obtained using a Scanning Electron Microscope (SEM). FIG. 57 illustrates the structure of two multi-fiber bundles. First bundle 5701 and second fiber bundle 5702 comprise 8 fibers. First bundle 5701 clearly illustrates first fiber 5710, second fiber 5720, and third fiber 5730. FIG. 57 also distinctly shows the second end 5721 of second fiber 5720, third end 5721 of third fiber 5730, and fourth end 5739 of a fiber that is otherwise not distinctly identifiable. Surface 5705 is the ends of all of the fibers in the first fiber bundle.

Second fiber bundle 5702 shows fifth fiber 5740 and fifth end 5741; sixth fiber 5750 and sixth end 5751; seventh fiber 5760 and seventh end 5761; and eighth end 5749 of a fiber that is otherwise not distinctly identifiable. Surface 5706 is the end of all of the fibers in second fiber bundle 5702.

Figure 58:
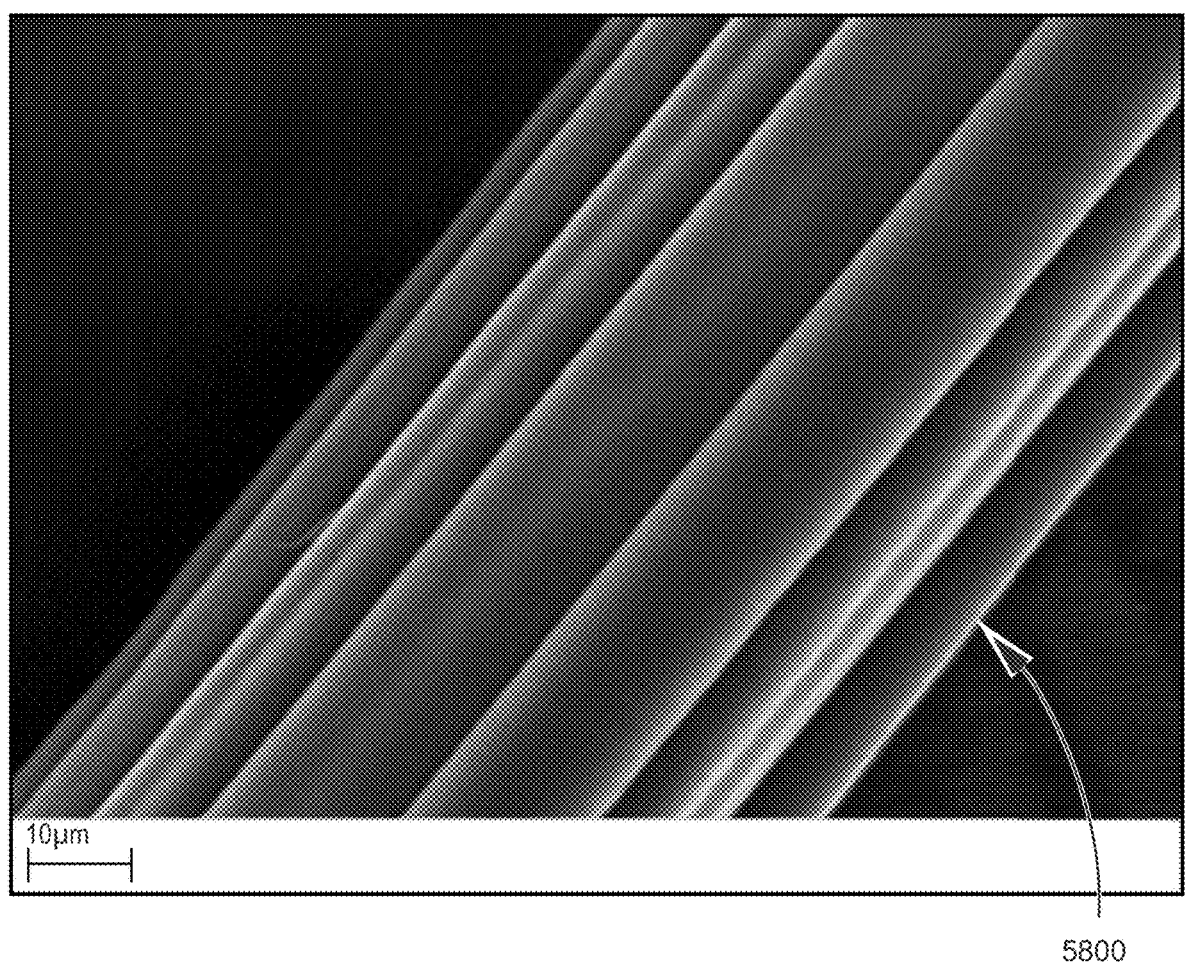
FIG. 58 is an SEM image of an embodiments of the disclosure.

FIG. 58 is an SEM image of an octa-fiber bundle.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

REFERENCES

All documents identified in this specification, including the following articles and patent properties, are incorporated by reference in their entireties.

PCT Application No. PCT/US2018/000119, attached hereto as Appendix A; and PCT Application No. PCT/US2018/57412, attached hereto as Appendix B;

Ahmad, Z. et al. (2015) 'Effect of 1-ethyl-3-(3-dimethylaminopropyl) carbodiimide and N-hydroxysuccinimide concentrations on the mechanical and biological characteristics of cross-linked collagen fibres for tendon repair', *Regenerative Biomaterials*, 2(2), pp. 77-85. doi: 10.1093/rb/rbv005.

Benjamin, M. (2010) *The structure of tendons and ligaments, Regenerative Medicine and Biomaterials for the Repair of Connective Tissues*. Woodhead Publishing. doi: 10.1533/9781845697792.2.351.

Benjamin, M., Kaiser, E. and Milz, S. (2008) 'Structure-function relationships in tendons: A review', *Journal of Anatomy*, 212, pp. 211-228. doi: 10.1111/j.1469-7580.2008.00864.x.

Bokor, D. J. et al. (2015) 'Preliminary investigation of a biological augmentation of rotator cuff repairs using a collagen implant: A 2-year MM follow-up', *Muscles, Ligaments and Tendons Journal*, 5(3), pp. 144-150. doi: 10.11138/mltj/2015.5.3.144.

Brown, B. N. et al. (2012) 'Macrophage phenotype as a predictor of constructive remodeling following the implantation of biologically derived surgical mesh materials', *Acta Biomaterialia*, 8(3), pp. 978-987. doi: 10.1016/j.actbio.2011.11.031.

Brown, B. N. and Badylak, S. F. (2013) 'Expanded applications, shifting paradigms and an improved understanding of host-biomaterial interactions', *Acta Biomaterialia*. Acta Materialia Inc., 9(2), pp. 4948-4955. doi: 10.1016/j.actbio.2012.10.025.

Caruso, A. B. and Dunn, M. G. (2004) 'Functional evaluation of collagen fiber scaffolds for ACL reconstruction: Cyclic loading in proteolytic enzyme solutions', *Journal of Biomedical Materials Research—Part A*, 69(1), pp. 164-171. doi: 10.1002/jbm.a.20136.

Chattopadhyay, S. and Raines, R. T. (2014) 'Review collagen-based biomaterials for wound healing', *Biopolymers*. doi: 10.1002/bip.22486.

Chen, J. et al. (2009) 'Scaffolds for tendon and ligament repair: Review of the efficacy of commercial products', *Expert Review of Medical Devices*, 6(1), pp. 61-73. doi: 10.1586/17434440.6.1.61.

Chu, C. C. (2013) 'Materials for absorbable and nonabsorbable surgical sutures', in *Biotextiles As Medical Implants*, pp. 275-334. doi: 10.1533/9780857095602.2.275.

Cornwell, K. G. et al. (2007) 'Crosslinking of discrete self-assembled collagen threads: Effects on mechanical strength and cell-matrix interactions', *Journal of Biomedical Materials Research Part A*, 80, pp. 362-371.

Cornwell, K. G., Downing, B. R. and Pins, G. D. (2004) 'Characterizing fibroblast migration on discrete collagen threads for applications in tissue regeneration', *Journal of Biomedical Materials Research—Part A*, 71, pp. 55-62. doi: 10.1002/jbm.a.30132.

Dai, J. et al. (2014) 'Acceleration of wound healing in acute full-thickness skin wounds using a collagen-binding peptide with an affinity for MSCs', *Burns & Trauma*, 2(4), p. 181. doi: 10.4103/2321-3868.143623.

Delgado, L. M. et al. (2015) 'To Cross-Link or Not to Cross-Link? Cross-Linking Associated Foreign Body Response of Collagen-Based Devices', *Tissue Engineering Part B: Reviews*, 21(3), pp. 298-313. doi: 10.1089/ten.teb.2014.0290.

Dunn, M. G., Avasarala, P. N. and Zawadsky, J. P. (1993) 'Optimization of extruded collagen fibers for ACL reconstruction', *Journal of Biomedical Materials Research*, 27(12), pp. 1545-52. doi: 10.1002/jbm.820271211.

Elder, S. et al. (2017) 'Suitability of EGCG as a Means of Stabilizing a Porcine Osteochondral Xenograft.', *Journal of functional biomaterials*, 8(43). doi: 10.3390/jfb8040043.

Enea, D. et al. (2011) 'Extruded collagen fibres for tissue engineering applications: Effect of crosslinking method on mechanical and biological properties', *Journal of Materials Science: Materials in Medicine*, 22(6), pp. 1569-1578. doi: 10.1007/s10856-011-4336-1.

Enea, D. et al. (2013) 'Collagen fibre implant for tendon and ligament biological augmentation. In vivo study in an ovine model', *Knee Surgery, Sports Traumatology, Arthroscopy*, 21(8), pp. 1783-1793. doi: 10.1007/s00167-012-2102-7.

Fathima, N. N. et al. (2004) 'Interaction of aldehydes with collagen: Effect on thermal, enzymatic and conformational stability', *International Journal of Biological Macromolecules*, 34(4), pp. 241-247. doi: 10.1016/j.ijbiomac.2004.05.004.

Gallagher, A. J. et al. (2012) 'Dynamic tensile properties of human skin', in *2012 IRCOBI Conference Proceedings—International Research Council on the Biomechanics of Injury*, pp. 494-502.

Gentleman, E. et al. (2003) 'Mechanical characterization of collagen fibers and scaffolds for tissue engineering', *Biomaterials*, 24(21), pp. 3805-3813. doi: 10.1016/S0142-9612(03)00206-0.

Gigante, A. et al. (2009) 'Collagen I membranes for tendon repair: Effect of collagen fiber orientation on cell behavior', *Journal of Orthopaedic Research*, 27, pp. 826-832. doi: 10.1002/jor.20812.

Gordon, S. and Taylor, P. R. (2005) 'Monocyte and macrophage heterogeneity', *Nature Reviews Immunology*, 5(12), pp. 953-964. doi: 10.1038/nri1733.

Gough, J. E., Scotchford, C. A. and Downes, S. (2002) 'Cytotoxicity of glutaraldehyde crosslinked collagen/poly (vinyl alcohol) films is by the mechanism of apoptosis', *Journal of Biomedical Materials Research*, 61(1), pp. 121-130. doi: 10.1002/jbm.10145.

Haugh, M. G., Jaasma, M. J. and O'Brien, F. J. (2009) 'The effect of dehydrothermal treatment on the mechanical and structural properties of collagen-GAG scaffolds', *Journal of Biomedical Materials Research—Part A*, 89(2), pp. 363-369. doi: 10.1002/jbm.a.31955.

Haynl, Christian, Hofmann, Eddie, Pawar, Kiran, Förster, Stephan, and Thomas Scheibel 'Microfluidics-produced collagen fibers show extraordinary mechanical properties,' *NanoLetters*

Hogan, M. V. et al. (2015) 'Tissue engineering of ligaments for reconstructive surgery', *Arthroscopy—Journal of Arthroscopic and Related Surgery*. Arthroscopy Association of North America, 31(5), pp. 971-979. doi: 10.1016/j.arthro.2014.11.026.

Van Kampen, C. et al. (2013) 'Tissue-engineered augmentation of a rotator cuff tendon using a reconstituted collagen scaffold: A histological evaluation in sheep', *Muscles, Ligaments and Tendons Journal*, 3(229-235). doi: 10.11138/mltj/2013.3.3.229.

Kasner, E. et al. (2009) 'Macrophage phenotype and remodeling outcomes in response to biologic scaffolds with and without a cellular component', *Biomaterials*, 30(8), pp. 1482-1491. doi: 10.1016/j.biomaterials.2008.11.040.Macrophage.

Kato, Y. P. et al. (1989) 'Mechanical properties of collagen fibres: a comparison of reconstituted and rat tail tendon fibres', *Biomaterials*, 10, pp. 38-42. doi: 10.1016/0142-9612(89)90007-0.

Kiapour, A. M. et al. (2015) 'Validation of Porcine Knee as a Sex-specific Model to Study Human Anterior Cruciate Ligament Disorders', *Clinical Orthopaedics and Related Research*, 473(2), pp. 639-650. doi: 10.1007/s11999-014-3974-2.

Koob, T. J. et al. (2001) 'Biocompatibility of NGDA-polymerized collagen fibers. II. Attachment, proliferation, and migration of tendon fibroblasts in vitro', *Journal of Biomedical Materials Research*, 56, pp. 40-48. doi: 10.1002/1097-4636(200107)56:1<40::AID-JBM1066>3.0.00; 24.

Kudur, M. H. et al. (2009) 'Sutures and suturing techniques in skin closure', *Indian Journal of Dermatology, Venereology and Leprology*, 75(4), pp. 425-434. doi: 10.4103/0378-6323.53155.

Lee, C. H., Singla, A. and Lee, Y. (2001) 'Biomedical applications of collagen', *International Journal of Pharmaceutics*, 221, pp. 1-21. doi: 10.1016/S0378-5173(01)00691-3.

Leiter, J. R. S. et al. (2014) 'Long-term follow-up of ACL reconstruction with hamstring autograft', *Knee Surgery, Sports Traumatology, Arthroscopy*, 22(5), pp. 1061-1069. doi: 10.1007/s00167-013-2466-3.

Liu, S. H. et al. (1995) 'Collagen in tendon, ligament, and bone healing: A current review', *Clinical Orthopaedics and Related Research*, (318), pp. 265-278.

Maghdouri-White, Y. et al. (2019) 'Biomanufacturing and Translational Research of an Aligned Collagen-Based Electrospun Tissue ENgineered Device (TEND) for Tendon Regeneration', manuscript submitted.

Matsusue, Y. et al. (1995) 'Tissue reaction of bioabsorbable ultra high strength poly (L-lactide) rod: A long-term study in rabbits', *Clinical Orthopaedics and Related Research*, 317, pp. 246-253.

Meena, C., Mengi, S. A. and Deshpande, S. G. (1999) 'Biomedical and industrial applications of collagen', *Proceedings of the Indian Academy of Sciences: Chemical Sciences*, 111(2), pp. 319-329. doi: 10.1007/BF02871912.

Meyer, M. (2019) 'Processing of collagen based biomaterials and the resulting materials properties', *BioMedical Engineering Online*. BioMed Central, 18(1), pp. 1-74. doi: 10.1186/s12938-019-0647-0.

Mills, C. D. et al. (2000) 'M-1/M-2 Macrophages and the Th1/Th2 Paradigm', *The Journal of Immunology*, 164 (12), pp. 6166-6173. doi: 10.4049/jimmunol.164.12.6166.

Ming-Che, W., Pins, G. D., Silver, F. H., 'Collagen fibres with improved strength for the repair of soft tissue injuries.' *Biomaterials* 15, 507-512 (1994).

Mosser, D. M. (2003) 'The many faces of macrophage activation', *Journal of Leukocyte Biology*, 73(2), pp. 209-212. doi: 10.1189/jlb.0602325.

Noyes, F. and Grood, E. (1976) 'The strength of the anterior cruciate ligament in humans and Rhesus monkeys', *The Journal of Bone & Joint Surgery*, 58(8), pp. 1074-1082. doi: 10.2106/00004623-197658080-00006.

Paul, R. G. and Bailey, A. J. (2003) 'Chemical stabilisation of collagen as a biomimetic.', *The Scientific World Journal*, 3, pp. 138-155. doi: 10.1100/tsw.2003.13.

Perrone, G. S. et al. (2017) 'Bench-to-bedside: Bridge-enhanced anterior cruciate ligament repair', *Journal of Orthopaedic Research*. doi: 10.1002/jor.23632.

Peters, A. E. et al. (2018) 'Tissue material properties and computational modelling of the human tibiofemoral joint: a critical review', *Peer J*, 6, p. e4298. doi: 10.7717/peerj.4298.

Porcheray, F. et al. (2005) 'Macrophage activation switching: An asset for the resolution of inflammation', *Clinical and Experimental Immunology*, 142, pp. 481-489. doi: 10.1111/j.1365-2249.2005.02934.x.

Rangaraj, A., Harding, K. and Leaper, D. (2011) 'Role of collagen in wound management', *Wounds UK*, 7(2), pp. 54-63.

Ratcliffe, A. et al. (2015) 'Scaffolds for Tendon and Ligament Repair and Regeneration', *Annals of Biomedical Engineering*, 43(3), pp. 819-831. doi: 10.1007/s10439-015-1263-1.

Ratner, B. D. (2011) 'The biocompatibility manifesto: Biocompatibility for the twenty-first century', *Journal of Cardiovascular Translational Research*, 4, pp. 523-527. doi: 10.1007/s12265-011-9287-x.

Reddy, N., Reddy, R. and Jiang, Q. (2015) 'Crosslinking biopolymers for biomedical applications', *Trends in Biotechnology*. Elsevier Ltd, 33(6), pp. 362-369. doi: 10.1016/j.tibtech.2015.03.008.

Sanchez-Ruiz, J. M. (1995) 'Differential scanning calorimetry of proteins.', in *Proteins: Structure, Function, and Engineering. Subcellular Biochemistry*, pp. 133-176. doi: 10.1007/978-1-4899-1727-0_6.

Schlegel, T. F. et al. (2018) 'Radiologic and clinical evaluation of a bioabsorbable collagen implant to treat partial-thickness tears: a prospective multicenter study', *Journal of Shoulder and Elbow Surgery*, 27(2), pp. 242-251. doi: 10.1016/j.jse.2017.08.023.

Seon, J. K., Song, E. K. and Park, S. J. (2006) 'Osteoarthritis after anterior cruciate ligament reconstruction using a patellar tendon autograft', *International Orthopaedics*, 30(2), pp. 94-98. doi: 10.1007/s00264-005-0036-0.

Shaerf, D. A. (2014) 'Anterior cruciate ligament reconstruction best practice: A review of graft choice', *World Journal of Orthopedics*, 5(1), p. 23. doi: 10.5312/wjo.v5.i1.23.

Shepherd, D. V. et al. (2015) 'The process of EDC-NHS cross-linking of reconstituted collagen fibres increases collagen fibrillar order and alignment', *APL Materials*, 3(1), pp. 1-13. doi: 10.1063/1.4900887.

Sherman, O. H. and Banffy, M. B. (2004) 'Anterior cruciate ligament reconstruction: Which graft is best?', *Arthroscopy—Journal of Arthroscopic and Related Surgery*, 20(9), pp. 974-980. doi: 10.1016/S0749-8063(04)00842-4.

Showery, J. E. et al. (2016) 'The Rising Incidence of Degenerative and Posttraumatic Osteoarthritis of the Knee in the United States Military', *Journal of Arthroplasty*, 31(10), pp. 2108-2114. doi: 10.1016/j.arth.2016.03.026.

van Sliedregt, A. et al. (1994) 'Evaluation of polylactide monomers in an in vitro biocompatibility assay', *Biomaterials*, 15(4), pp. 251-256. doi: 10.1016/0142-9612(94)90047-7.

Smith, T. O. et al. (2014) 'Is reconstruction the best management strategy for anterior cruciate ligament rupture? A systematic review and meta-analysis comparing anterior cruciate ligament reconstruction versus non-operative treatment', *Knee*, 21(2), pp. 462-470. doi: 10.1016/j.knee.2013.10.009.

Stout, R. D. et al. (2005) 'Macrophages Sequentially Change Their Functional Phenotype in Response to Changes in Microenvironmental Influences', *The Journal of Immunology*, 175, pp. 342-349. doi: 10.4049/jimmunol.175.1.342.

Taylor, M. S. et al. (1994) 'Six bioabsorbable polymers: In vitro acute toxicity of accumulated degradation products', *Journal of applied biomaterials*, 5(2), pp. 151-157. doi: 10.1002/jab.770050208.

Tsugawa, A. J. and Verstraete, F. J. M. (2012) 'Suture materials and biomaterials', in *Oral and Maxillofacial Surgery in Dogs and Cats*, pp. 69-78. doi: 10.1016/B978-0-7020-4618-6.00007-5.

Umashankar, P., Kumari, T. and Mohanan, P. (2012) 'Glutaraldehyde treatment elicits toxic response compared to decellularization in bovine pericardium', *Toxicology International*, 19, pp. 51-58. doi: 10.4103/0971-6580.94513.

Vavken, P. et al. (2012) 'Biomechanical outcomes after bioenhanced anterior cruciate ligament repair and anterior cruciate ligament reconstruction are equal in a porcine model', *Arthroscopy—Journal of Arthroscopic and Related Surgery*, 28(5), pp. 672-680. doi: 10.1016/j.arthro.2011.10.008.

Vijayaraghavan, R. et al. (2010) 'Biocompatibility of choline salts as crosslinking agents for collagen based biomaterials', *Chemical Communications*, 46(2), pp. 294-296. doi: 10.1039/b910601d.

Vunjak-Novakovic, G. et al. (2004) 'Tissue Engineering of Ligaments', *Annual Review of Biomedical Engineering*. Annual Reviews, 6(1), pp. 131-156. doi: 10.1146/annurev.bioeng.6.040803.140037.

Wang, J. H.-C., Guo, Q. and Li, B. (2012) 'Tendon Biomechanics and Mechanobiology—a mini-review of basic concepts', *Journal of Hand Therapy*, 25(2), pp. 133-141. doi: 10.1016/j.jht.2011.07.004.Tendon.

Wang, L. and Stegemann, J. P. (2011) 'Glyoxal crosslinking of cell-seeded chitosan/collagen hydrogels for bone regeneration', *Acta Biomaterialia*, 7(6), pp. 2410-2417. doi: 10.1016/j.actbio.2011.02.029.

Watts, G. (1975) 'SUTURES FOR SKIN CLOSURE', *The Lancet*, 305(7906), p. 581.

Wiegnad, N., Patczai, B. and Lörinczy, D. (2017) 'The Role of Differential Scanning calorimetry in the Diagnostics of Musculoskeletal Diseases', *EC Orthopaedics*, 4, pp. 164-177.

Woo, S. L. Y. et al. (1999) 'Tissue engineering of ligament and tendon healing', in *Clinical Orthopaedics and Related Research*. doi: 10.1097/00003086-199910001-00030.

Wren, T. A. L. et al. (2001) 'Mechanical properties of the human achilles tendon', *Clinical Biomechanics*, 16, pp. 245-251. doi: 10.1016/S0268-0033(00)00089-9.

Yaari, Amit, Schilt, Yaelle, Tamburu, Carmen, Raviv, Uri, and Shoseyov, Oded, 'Wet Spinning and Drawing of Human Recombinant Collagen', *ACS Biomaterials*

Yang, G., Rothrauff, B. B. and Tuan, R. S. (2013) 'Tendon and ligament regeneration and repair: Clinical relevance and developmental paradigm', *Birth Defects Research Part C—Embryo Today: Reviews*, pp. 203-222. doi: 10.1002/bdrc.21041.

Yannas, I. V. and Tobolsky, A. V (1967) 'Cross-linking of Gelatine by Dehydration', *Nature*, 215(5100), pp. 509-510. doi: 10.1038/215509b0.

Zeugolis, D. I., Paul, G. R. and Attenburrow, G. (2009) 'Cross-linking of extruded collagen fibers-A biomimetic three-dimensional scaffold for tissue engineering applications', *Journal of Biomedical Materials Research—Part A*, 89(4), pp. 895-908. doi: 10.1002/jbm.a.32031

We claim:

1. An implantable biopolymer scaffold for supporting repair of a soft tissue comprising a plurality of extruded collagen fibers;
   wherein the fibers have sub-fibers; and
   wherein the sub-fibers are cross-linked with glyoxal.

2. The implantable biopolymer scaffold of claim 1, wherein the extruded collagen fibers exhibit an ordered, longitudinally oriented structure.

3. The implantable biopolymer scaffold of claim 2,
   wherein the extruded collagen fibers have one or more of the following characteristics:
   an ultimate tensile strength of between about 1 MPa to about 1,700 MPa;
   a modulus of elasticity of between about 10 MPa to about 20,000 MPa;
   a strain at break of between about 2 percent and about 45 percent elongation;
   an average fiber diameter between about 10 μm and about 90 μm;
   maintains its strength after soaking in Dulbecco's Phosphate Buffered Solution ("DPBS") at room temperature for at least about 1 hour;
   retains fifty percent of its initial load-bearing capacity for three months in culture;
   and promotes an elevated pro-regenerative M2 macrophage response in vivo.

4. The implantable biopolymer scaffold of claim 1, wherein the extruded collagen fibers are telocollagen having a degree of cross linking of at least about 85 percent or atelocollagen having a degree of cross linking of at least about 65 percent.

5. The implantable biopolymer scaffold of claim 1, wherein the collagen is type I collagen.

6. The implantable biopolymer scaffold of claim 5, wherein the collagen is selected from the group consisting of clinical grade collagen, atelocollagen, telocollagen, recombinant collagen, and blends thereof.

7. The implantable biopolymer scaffold of claim 1, wherein the extruded collagen fibers have a cross section selected from the group consisting of substantially circular, ovoid, square, rectangular, ribbonlike, triangular, or irregular shapes.

8. The implantable biopolymer scaffold of claim 1, wherein the extruded collagen fibers further comprise a bio-acceptable polymer.

9. The implantable biopolymer scaffold of claim 1, wherein the extruded collagen fibers are associated in a form factor that is bundled, braided, interwoven, or twisted.

10. The implantable biopolymer scaffold of claim 9, wherein the form factor is a bundle; and wherein the bundle comprises between 2 and about 10,000 extruded collagen fibers.

11. The implantable biopolymer scaffold of claim 10, wherein the bundle comprises between 2 and about 150 extruded collagen fibers.

12. The implantable biopolymer scaffold of claim 1, wherein the implantable biopolymer scaffold has a form factor selected from the group consisting of a suture, a construct, a platform, a support, patch, single sheet, plurality of sheets, or an internal brace.

13. The implantable biopolymer scaffold of claim 12, wherein the form factor is a suture;
    wherein the suture is resorbable; and
    wherein the suture exhibits cellular infiltration after implantation in a subject.

14. The implantable biopolymer scaffold of claim 13, wherein the suture comprises about 2 to 12 extruded collagen fibers.

15. The implantable biopolymer scaffold of claim 13, wherein the suture is coated.

16. The implantable biopolymer scaffold of claim 1, further comprising adhered tenocytes;
    wherein the tenocytes retain at least about 75% cell viability and at least about 95% cell survival after about seven days incubation under conventional mammalian cell culture conditions of temperature, pH, and humidity.

17. An implantable biopolymer scaffold for supporting repair of a soft tissue injury comprising a plurality of high strength extruded collagen fibers;
    wherein sub-fibers of the high strength extruded fibers are cross-linked with glyoxal;
    wherein the fibers exhibit an ordered, longitudinally oriented structure; and
    wherein the extruded collagen fibers have one or more of the following characteristics:
        an ultimate tensile strength of between about 1 MPa to about 800 MPa;
        a modulus of elasticity of between about 10 MPa to about 7,500 MPa; and
        an average fiber diameter of between about 10 µm and about 70 µm.

18. The implantable biopolymer scaffold of claim 17, wherein the high strength extruded collagen fibers have one or more of the following characteristics:
    an ultimate tensile strength of between about 20 MPa to about 170 MPa;
    a modulus of elasticity of between about 200 MPa to about 3,500 MPa; and
    an average fiber diameter between about 16 µm and about 30 µm after soaking for about 1 hour in phosphate-buffered saline solution; and
    wherein the scaffold has a form factor configured to replace a human body part after implantation into a subject.

19. The implantable biopolymer scaffold of claim 17 wherein the high strength extruded collagen fibers have strain at break of between about 4 percent and about 12 percent elongation.

20. The implantable biopolymer scaffold of claim 17, wherein the high strength extruded collagen fibers maintain a strength greater than about 60 MPa after 6 months in DBPS at room temperature.

21. The implantable biopolymer scaffold of claim 12, wherein the form factor is an internal brace.

22. The implantable biopolymer scaffold of claim 21, wherein the soft tissue comprises a ligament or a tendon; and
    wherein the implantable biopolymer scaffold is capable of attaching the ligament or tendon to bone.

23. The implantable biopolymer scaffold of claim 12, wherein the form factor is an interwoven sheet-like support or patch.

24. The implantable biopolymer scaffold of claim 21, wherein the scaffold comprises a plurality of layers.

25. An implantable biopolymer scaffold for supporting repair of a soft tissue comprising a plurality of high strength extruded biopolymer fibers, wherein the high strength extruded biopolymer fiber has one or more of the following characteristics:
    an ultimate tensile strength of between about 20 MPa to about 170 MPa;
    a modulus of elasticity of between about 200 MPa to about 3,500 MPa;
    a strain at break of between about 4 percent and about 12 percent elongation;
    an average fiber diameter between about 16 µm and less than about 200 µm after drying;
    maintains its strength after soaking in biological fluid for about 1 hour; and
    promotes an elevated pro-regenerative M2 macrophage response in vivo; and
    wherein the high strength extruded collagen fibers are telocollagen having a degree of cross linking of at least about 85 percent or atelocollagen having a degree of cross linking of at least about 65 percent.

26. The implantable biopolymer scaffold of claim 25, wherein the high strength extruded biopolymer fibers are twisted.

27. The implantable biopolymer scaffold of claim 25, wherein
    the scaffold includes pores, the pores being configured to allow cells from the soft tissue to grow thereinto such that the cells are aligned with the fibers in the scaffold.

28. The implantable biopolymer scaffold of claim 25, wherein the scaffold is configured to provide support for a human ligament selected from the group consisting of: the ACL, the MCL, the PCL, and the UCL.

29. The implantable biopolymer scaffold of claim 25, comprising between 2 and about 10,000 high strength biopolymer fibers.

30. The implantable biopolymer scaffold of claim 25, wherein the high strength biopolymer fiber maintains a strength greater than about 60 MPa after implantation into a subject.

* * * * *